US012421555B2

(12) United States Patent
Abkevich et al.

(10) Patent No.: US 12,421,555 B2
(45) Date of Patent: *Sep. 23, 2025

(54) METHODS AND MATERIALS FOR ASSESSING HOMOLOGOUS RECOMBINATION DEFICIENCY

(71) Applicant: Myriad Genetics, Inc., Salt Lake City, UT (US)

(72) Inventors: Victor Abkevich, Salt Lake City, UT (US); Kirsten Timms, Salt Lake City, UT (US); Alexander Gutin, Salt Lake City, UT (US); Julia Reid, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 1379 days.

This patent is subject to a terminal disclaimer.

(21) Appl. No.: 16/221,165

(22) Filed: Dec. 14, 2018

(65) Prior Publication Data

US 2019/0185939 A1 Jun. 20, 2019

Related U.S. Application Data

(63) Continuation of application No. 15/433,249, filed on Feb. 15, 2017, now Pat. No. 10,400,287, which is a continuation of application No. PCT/US2015/045561, filed on Aug. 17, 2015, which is a continuation of application No. 14/507,412, filed on Oct. 6, 2014, now abandoned.

(60) Provisional application No. 62/037,764, filed on Aug. 15, 2014.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 3,590,028 | A | 6/1971 | Arcamone |
| 3,892,790 | A | 7/1975 | Tobe |
| 3,904,663 | A | 9/1975 | Tobe |
| 4,138,480 | A | 2/1979 | Gosalvez |
| 4,946,954 | A | 8/1990 | Talebian |
| 4,950,738 | A | 8/1990 | King |
| 4,996,337 | A | 2/1991 | Bitha |
| 5,091,521 | A | 2/1992 | Kolar |
| 5,177,075 | A | 1/1993 | Suto |
| 5,214,821 | A | 6/1993 | Burrow |
| 5,295,944 | A | 3/1994 | Teicher |
| 5,434,256 | A | 7/1995 | Khokhar |
| 5,445,934 | A | 8/1995 | Fodor |
| 5,510,270 | A | 4/1996 | Fodor |
| 5,527,905 | A | 6/1996 | Sugimura |
| 5,539,083 | A | 7/1996 | Cook |
| 5,556,752 | A | 9/1996 | Lockhart |
| 5,578,832 | A | 11/1996 | Trulson |
| 5,633,016 | A | 5/1997 | Johnson |
| 5,633,243 | A | 5/1997 | Sugimura |
| 5,744,305 | A | 4/1998 | Fodor |
| RE36,397 | E | 11/1999 | Zhang et al. |
| 6,040,138 | A | 3/2000 | Lockhart |
| 6,087,340 | A | 7/2000 | Gatti |
| 6,210,891 | B1 | 4/2001 | Nyren |
| 6,214,821 | B1 | 4/2001 | Daoud |
| 6,258,568 | B1 | 7/2001 | Nyren |
| 6,274,320 | B1 | 8/2001 | Rothberg |
| 6,403,563 | B1 | 6/2002 | Geroni |
| 6,455,258 | B2 | 9/2002 | Bastian |
| 6,465,177 | B1 | 10/2002 | Hoon |
| 6,534,293 | B1 | 3/2003 | Barany |
| 7,351,701 | B2 | 4/2008 | Helleday |
| 7,485,707 | B2 | 2/2009 | Matvienko |
| 7,732,491 | B2 | 6/2010 | Sherman |
| 7,754,684 | B2 | 7/2010 | Stewart |
| 7,759,488 | B2 | 7/2010 | Xiao |
| 7,759,510 | B2 | 7/2010 | Kay |

(Continued)

FOREIGN PATENT DOCUMENTS

| EP | 0430402 | 6/1991 |
| EP | 1260520 | 11/2002 |

(Continued)

OTHER PUBLICATIONS

Popova et al. Cancer Research 72(21); 5454-62 Nov. 1, 2012 (Year: 2012).*
Gnirke et al., "Solution Hybrid Selection with Ultra-long Oligonucleotides for Massively Parallel Targeted Sequencing" Nat Biotechnol., 2009.
Halper-Stromberg, E. et al. (2011) Performance assessment of copy No. microarray platforms using a spike-in experiment. Bioinformatics 27(8): 1052-60 (Apr. 2011).
Hedges et al., "Comparison of Three Targeted Enrichment Strategies on the SOLiD Sequencing Platform" PLoS One, 2011.
Isakoff, S.J. et al. (2014), Identification of biomarkers to predict response to single-agent platinum chemotherapy in metastatic triple-negative breast cancer (mTNBC): Correlative studies from TBCRC009.
Jelovac, D. and Armstrong, D.K., "Recent Progress in the Diagnosis and Treatment of Ovarian Cancer", CA Cancer J Clin, 61/3, pp. 183-203, https://doi.org/10.3322/caac.20113, Apr. 26, 2011 (Apr. 26, 2011).

(Continued)

*Primary Examiner* — Jeffrey S Lundgren
*Assistant Examiner* — Michael J Schmitt
(74) *Attorney, Agent, or Firm* — Foley & Lardner LLP

(57) ABSTRACT

This document provides methods and materials involved in assessing samples (e.g., cancer cells) for the presence of homologous recombination deficiency (HRD) or an HRD signature. For example, methods and materials for determining whether or not a cell (e.g., a cancer cell) contains an HRD signature are provided. Materials and methods for identifying cells (e.g., cancer cells) having a deficiency in homology directed repair (HDR) as well as materials and methods for identifying cancer patients likely to respond to a particular cancer treatment regimen also are provided.

10 Claims, 26 Drawing Sheets

(56) References Cited

U.S. PATENT DOCUMENTS

| | | | |
|---|---|---|---|
| 7,858,331 | B2 | 12/2010 | D Andrea |
| 7,860,840 | B2 | 12/2010 | Johnson |
| 7,868,040 | B2 | 1/2011 | Wilson |
| 7,915,280 | B2 | 3/2011 | Ferraris |
| 9,279,156 | B2 | 3/2016 | Gutin |
| 9,574,229 | B2 | 2/2017 | Gutin |
| 2003/0049613 | A1 | 3/2003 | Perucho |
| 2005/0112604 | A1 | 5/2005 | Fujimoto |
| 2006/0088870 | A1 | 4/2006 | Finkelstein |
| 2007/0004621 | A1 | 1/2007 | Shridhar |
| 2007/0070349 | A1 | 3/2007 | Harris |
| 2008/0108057 | A1 | 5/2008 | Griffith |
| 2008/0262062 | A1 | 10/2008 | Ossovskaya |
| 2009/0081237 | A1 | 3/2009 | D Andrea |
| 2009/0246789 | A1 | 10/2009 | Buckhaults |
| 2010/0130527 | A1 | 5/2010 | Lehrer |
| 2010/0145894 | A1 | 6/2010 | Semizarov |
| 2010/0159466 | A1 | 6/2010 | Eng |
| 2012/0015050 | A1 | 1/2012 | Abkevich |
| 2013/0281312 | A1 | 10/2013 | Richardson |
| 2014/0363521 | A1 | 12/2014 | Abkevich |
| 2015/0080260 | A1 | 3/2015 | Abkevich |

FOREIGN PATENT DOCUMENTS

| | | | |
|---|---|---|---|
| EP | 2981624 | | 2/2016 |
| EP | 2981624 | A2 | 2/2016 |
| KR | 100925337 | B1 | 11/2009 |
| WO | 9520952 | | 8/1995 |
| WO | 9841531 | | 9/1998 |
| WO | 9954498 | | 10/1999 |
| WO | 0024933 | | 5/2000 |
| WO | 03074723 | A2 | 9/2003 |
| WO | 2004042032 | | 5/2004 |
| WO | 2004075833 | | 9/2004 |
| WO | 2006098978 | | 9/2006 |
| WO | 2006110855 | | 10/2006 |
| WO | 2006116341 | | 11/2006 |
| WO | 2006128195 | | 11/2006 |
| WO | 2007035893 | | 3/2007 |
| WO | 2009033178 | | 3/2009 |
| WO | 2009073869 | | 6/2009 |
| WO | 2009148528 | | 12/2009 |
| WO | 2010028288 | | 3/2010 |
| WO | 2010051318 | | 5/2010 |
| WO | 2011048495 | | 4/2011 |
| WO | 2011106541 | | 9/2011 |
| WO | 2011160063 | | 12/2011 |
| WO | 2012019000 | | 2/2012 |
| WO | 2012027224 | | 3/2012 |
| WO | 2012092426 | A1 | 7/2012 |
| WO | 2013096843 | | 6/2013 |
| WO | 2013096843 | A1 | 6/2013 |
| WO | 2013130347 | | 9/2013 |
| WO | WO-2013130347 | A1 * 9/2013 ........... C12Q 1/6886 |
| WO | 2013182645 | | 12/2013 |
| WO | 2014165785 | | 10/2014 |
| WO | 2015086473 | A1 | 6/2015 |
| WO | 2015108986 | A1 | 7/2015 |

OTHER PUBLICATIONS

Ji, H. & Welch, K. (2009) Molecular inversion probe assay for allelic quantitation. Methods Mol Biol. 556: 67-87 (2010).
Kissel et al., "Translation of an STR-based biomarker into a clinically compatible SN P-based platform for loss of heterozygosity" Cancer Biomark, 2009.
Li, X. et al. (2007) Direct Inference of SNP Heterozygosity Rates and Resolution of LOH Detection. PLoS Computational Biology 3(11): e244 (2007).
Lieberfarb et al., "Genome-wide loss of heterozygosity analysis from laser capture microdissected prostate cancer using single nucleotide polymorphic allele (SNP) arrays and a novel bioinformatics platform dChipSNP", Cancer Res. Aug. 15, 2003;63(16):4781-5.
Mayer, E.L. et al. (2014), TBCRC030: A randomized, phase II study of preoperative cisplatin versus paclitaxel in patients (pts) with BRCA1/2-proficient triple-negative breast cancer (TNBC)—Evaluating the homologous recombination deficiency (HRD) biomarker. Journal of Clinical Oncology 32, No. 15_suppl; published on May 2, 2014.
MLO Staff, Myriad presents data on BRXAnalysis CDx and HRD at 2014 ASCO meeting, [online], Jun. 2, 2014, <URL:https://www.mlo-online.com/myriad-presents-data-on-bracanalysis-cdx-and-hrd-at-2014-asco-meeting.php>.
Myriad Genetics, Inc., Myriad's HRD Test Significantly Predicts Response to Cisplatin Treatment in Patients With Triple Negative Breast Cancer in Second Research Study, [online], Dec. 14, 2013, <URL: http://investor.myriad.com/static-files/81065ca7-d234-4ece-b0b3-acde2d4c7ed7>.
Press release of Myriad Genetics, Inc. of Dec. 14, 2013, Myriad's HRD Test Significantly Predicts Response to Cisplatin Treatment in Patients With Triple Negative Breast Cancer in Second Research Study.
Press release of Myriad Genetics, Inc. of May 30, 2014 "Myriad Presents Data on BRACAnalysis CDx™ and HRD™ at 2014 ASCO Meeting".
Ross and Cronin, Whole Cancer Genome Sequencing by Next-Generation Methods; Am J Clin Pathol 136:527-539 (2011).
Van Puijenbroek et al., Mass Spectrometry-Based Loss of Heterozygosity Analysis of Single-Nucleotide Polymorphism Loci in Paraffin Embedded Tumors Using the MassEXTEND Assay J. Mol. Diag 7(5):623-630 (2005).
Wang, Y. et al. (2005) Allele quantification using molecular inversion probes (MIP). Nucleic Acids Research 33 (21): e 183 (2005).
Wang, Y. et al. (2009) High quality copy number and genotype data from FFPE samples using Molecular Inversion Probe (MIP) microarrays. BMC Medical Genomics, 2(8): 1-13.
Watkins, J.A. et al (2014), Genomic scars as biomarkers of homologous recombination deficiency and drug response in breast and ovarian cancers. Breast Cancer Research 16:211; published on Jun. 3, 2014.
Abkevich et al. "Patterns of genomic loss of heterozygosity predict homologous recombination repair defects in epithelial ovarian cancer", British Journal of Cancer, vol. 107, No. 10, Oct. 9, 2012, pp. 1776-1782.
Abkevich et al. "Supplemental Material: Table S1: Validation of copy number determinations by Real Time PCR SNP ID Adjacent Gene Sample Copy Number by Real-Time PCR Copy Number by CCNT SNP A",-1712744 CDKN2A HF505 0.010 0.47 HF1382 0.14 0, Oct. 1, 2006, pp. 5-1713144, XP055085899, Retrieved from the Internet: URL: http://cancerres.aacrjournals.org/content/suppl/2006/10/04/66.19.9428.DC2/Supplementary-Tables-1-5.pdf [retrieved on Oct. 29, 2013].
Al-Mulla et al., "Metastatic recurrence of early-stage colorectal cancer is linked to loss of heterozygosity on Chromosomes 4 and 14q" Journal of Clinical Pathology, vol. 59, No. 6, pp. 624-630 (2006).
Anonymous, "Myriad's HRD Test Significantly Predicts Response to Cisplatin Treatment in Patients With Triple Negative Breast Cancer in Second Research Study", (Dec. 14, 2013), Myriad, URL: http://files.shareholder.com/downloads/MYGN/3039924177x0x713818/74F0EC3E-B337-4724-A51B-63BA3BD75A08/MYGN_News_2013_12_14_General.pdf, (Oct. 19, 2016), XP055312045.
Argos et al. "Genomewide scan for loss of heterozygosity and chromosomal amplification in breast carcinoma using single-nucleotide polymorphism arrays", Cancer Genetics and Cytogenetics, vol. 182, No. 2, Apr. 15, 2008, pp. 69-74.
Arlt et al., "BRCA1 Is Required for Common-Fragile-Site Stability via Its G2/M Checkpoint Function," Molecular and Cellular Biology, Aug. 2004, 24(15): 6701-6709.
Ashworth, "A Synthetic Lethal Therapeutic Approach: Poly(ADP) Ribose Polymerase Inhibitors for the Treatment of Cancers Deficient in DNA Double-Strand Break Repair," Journal of Clinical Oncology, Aug. 2008, 26(22): 3785-3790.

(56) References Cited

OTHER PUBLICATIONS

Audeh et al., "Novel Treatment Strategies in Triple-Negative Breast Cancer: Specific Role of Poly(adenosine Diphosphate-Ribose) Polymerase Inhibition", Pharmacogenomics and Personalized Medicine, vol. 7, 2014, pp. 307-316.
Bamford et al., "The COSMIC (Catalogue of Somatic Mutations in Cancer) database and website," British Journal of Cancer, 2004, 91: 355-358.
Beder L B et al.: "Genome-wide analyses on loss of heterozygosity in head and neck squamous cell carcinomas", Laboratory Investigation, vol. 83, No. 1, 2003, pp. 99-105, XP002703165.
Bell et al., "Integrated genomic analyses of ovarian carcinoma," Nature, Jun. 2011, 474: 609-615.
Bengtsson et al., "A single-array preprocessing method for estimating full-resolution raw copy numbers from all Affymetrix genotyping arrays including GenomeWideSNP 5 & 6," Bioinformatics, 2009, 25: 2149-2156.
Bengtsson et al., BMC Bioinformatics 11:245-262 (2010). "TumorBoost: Normalization of allele-specific tumor copy numbers from a single pair of tumor-normal genotyping microarrays."
Bernardini et al., "The use of cytogenetics in understanding ovarian cancer," Biomedicine and Pharmacotherapy, 2004, 58: 17-23.
Beroukhim et al. "Inferring Loss-of-Heterozygosity from Unpaired Tumors Using High-Density Oligonucleotide SNP Arrays", Bioinformatics, vol. 19, No. 5, Jan. 1, 2006 (Jan. 1, 2006), p. 2397.
Beroukhim et al., "Assessing the significance of chromosomal aberrations in cancer: methodology and application to glioma," Proc. Natl. Acad. Sci. U.S.A., 104(50):20007-12, Dec. 2007.
Birkbak et al. "Telomeric allelic imbalance indicates defective DNA repair and sensitivity to DNA-damaging agents"; Cancer Discov; 2012; 2(4): 366-375; doi: 10.1158/2159-8290.CD-11-0206.
Birkbak et al., "Abstract 4823: Copy number gain and increased expression of BLM and FANCI is associated with sensitivity to genotoxic chemotherapy in triple negative breast and serous ovarian cancer," Cancer Res., 72(8): 1, Apr. 15, 2012, 1 page.
Birkbak et al., "Paradoxical relationship between chromosomal instability and survival outcome in cancer," Cancer Res, May 2011, 71(10): 3447-3452.
Bouwman et al., "53BP1 loss rescues BRCA1 deficiency and is associated with triple-negative and BRCA-mutated breast cancers," Nature Structural & Molecular Biology, Jun. 2010, 17(6): 688-696.
Bryant et al; Specific killing of BRCA2-deficient tumours with inhibitors of poly(ADP-ribose) polymerase; Nature; 2005; 434(7035):913-917.
Buch H N et al.: "Prediction of recurrence of nonfunctioning pituitary tumours by loss of heterozygosity analysis", Clinical Endocrinology, vol. 61, 2004, p. 19-22, XP002703163.
Bunting et al., "53BP1 inhibits homologous recombination in Brca1-deficient cells by blocking resection of DNA breaks," Cell, Apr. 2010, 141(2): 243-254.
Burger et al., "Drug transporters of platinum-based anticancer agents and their clinical significance," Drug Resistance Updates, 2011, 14: 22-34.
Byrski et al., "Response to neoadjuvant therapy with cisplatin in BRCA1-positive breast cancer patients," Breast Cancer Res Treat, 2009, 115: 359-363.
Calvert et al. "245 Invited PARP inhibitors in cancer treatment", European Journal of Cancer. Supplement, Pergamon, Oxford, GB, vol. 6, No. 12, Oct. 1, 2008, p. 80.
Campbell et al., "A genetic variant that disrupts MET transcription is associated with autism," PNAS, Nov. 2006, 103: 16834-16839.
Carr et al., "High-resolution analysis of allelic imbalance in neuroblastoma cell lines by single nucleotide polymorphism arrays," Cancer Genetics and Cytogenetics, 2007, 172: 127-138.
Cass et al., "Improved Survival in Women with BRCA-Associated Ovarian Carcinoma," Cancer, May 2003, 97(9): 2187-2195.
Cerbinskaite et al; Defective homologous recombination in human cancers; Cancer Treat Rev; 2012; Epub 2011; 38(2): 89-100.
Cha and Kelckner, "ATR Homolog Mec1 Promotes Fork Progression, Thus Averting Breaks in Replication Slow Zones," Science, Jul. 2002, 297: 602-606.
Chang et al., "Assessment of Plasma DNA Levels, Allelic Imbalance, and CA 125 as Diagnostic Tests for Cancer," Journal of the National Cancer Institute, Nov. 2002, 94(22): 1697-1703.
Cheung T H et al.: "Clinicopathologic significance of loss of heterozygosity on chromosome 1 in cervical cancer" Gynecologic Oncology, Academic Press, London, GB, vol. 96, No. 2, Feb. 1, 2005, pp. 510-515, XP027205508, ISSN: 0090-8258 [retrieved on Jan. 18, 2005].
Choi et al., "Genetic Classification of Colorectal Cancer Based on Chromosomal Loss and Microsatellite Instability Predicts Survival," Clinical Cancer Research, Jul. 2002, 8:2311-2322.
Dann et al; BRCA1/2 mutations and expression: response to platinum chemotherapy in patients with advanced stage epithelial ovarian cancer; Gynecol Oncol; 2012;125(3):677-682.
De Preter et al., "Application of laser capture microdissection in genetic analysis of neuroblastoma and neuroblastoma precursor cells," Cancer Letters, 2003, 197: 53-61.
De Soto et al., "The Inhibition and Treatment of Breast Cancer with Poly (ADP-ribose) Polymerase (PARP-1) Inhibitors," Int. J. Biol. Sci., 2006, 179-185.
Duncavage et al., "Hybrid Capture and Next-Generation Sequencing Identify Viral Integration Sites From Formalin-Fixed, Paraffin-Embedded Tissue", The Journal of Molecular Diagnostics, 2011, vol. 13, No. 3, pp. 325-333.
Edwards et al; Resistance to therapy caused by intragenic deletion in BRCA2; Nature; 2008; 451(7182):1111-1115.
Etemadmoghadam et al., "Integrated Genome-Wide DNA Copy Number and Expression Analysis Identifies Distinct Mechanisms of Primary Chemoresistance in Ovarian Carcinomas," Clin Cancer Res, 2009, 15: 1417-1427.
Fang Min et al., "Genomic Differences Between Estrogen Receptor (ER)-Positive and ER-Negative Human Breast Carcinoma Identified by Single Nucleotide Polymorphism Array Comparative Genome Hybridization Analysis", Cancer, (May 2011), vol. 117, No. 10, pp. 2024-2034, XP002741861.
Farmer et al; Targeting DNA repair defect in BRCA mutant cells as a therapeutic strategy; Nature; 2005; 434 (7035):917-921.
Feltmate C M et al.: "Whole-genome allelotyping identified distinct loss-of-heterozygosity patterns in mucinous ovarian and appendiceal carcinomas", Clinical Cancer Research, vol. 11, No. 21, Nov. 1, 2005, pp. 7651-7657XP002703164.
Ferreira et al: "Array CGH and gene-expression profiling reveals distinct genomic instability patterns associated with DNA repair and cell-cycle checkpoint pathways in Ewing's sarcoma", Oncogene, vol. 27, No. 14, Mar. 27, 2008, pp. 2084-2090, XP55010742, ISSN: 0950-9232DOI: 10.1038/sj.onc.1210845.
Filopanti, M. et al., "Loss of heterozygosity at the SS receptor type 5 locus in human GH- and TSH-secreting pituitary adenomas", J. Endocrinol. Invest., (Nov. 2004), vol. 27, No. 10, pp. 937-942, XP008120366.
Fontanillas et al., "Key considerations for measuring allelic expression on a genomic scale using high-throughput sequencing", Molecular Ecology, vol. 19, No. 1, Mar. 1, 2010, pp. 212-227.
Franko, J. et al., "Loss of heterozygosity predicts poor survival after resection of pancreatic adenocarcinoma," J. Gastrointest. Surg., Oct. 2008, vol. 12, No. 10, pp. 1664-1723.
Friedenson; BRCA1 and BRCA2 pathways and the risk of cancers other than breast or ovarian; MedGenMed; 2005; 7(2):60, 25 pages.
Gelmon et al; Olaparib in patients with recurrent high-grade serous or poorly differentiated ovarian carcinoma or triple-negative breast cancer: a phase 2, multicentre, open-label, non-randomised study; Lancet Oncol; 2011;12(9):852-861.
Goransson et al; Quantification of normal cell fraction and copy No. neutral LOH in clinical lung cancer samples using SNP array data; PLoS One; 2009; 4(6):e6057; doi: 10.1371/journal.pone. 0006057,10 pages.
Gorringe et al., "Are There Any More Ovarian Tumor Suppressor Genes? A New Perspective Using Ultra High-Resolution Copy Number and Loss of Heterozygosity Analysis," Genes, Chromosones & Cancer, 2009,48: 931-942.

(56) References Cited

OTHER PUBLICATIONS

Graziani et al. "PARP-1 inhibition to treat cancer, ischemia, inflammation", Pharmacological Research, Academic Press, London, GB, vol. 52, No. 1, Jul. 1, 2005, pp. 1-4, XP004902631, ISSN: 1043-6618DOI: 10.1016/J.PHRS.2005.02.007.

Gudmundsdottir and Ashworth, "The roles of BRCA1 and BRCA2 and associated proteins in the maintenance of genomic stability," Oncogene, 2006, 25: 5864-5874.

Gunnarsson et al., "Large but not small copy-number alterations correlate to high-risk genomic aberrations and survival in chornic lymphocytic leukemia: a high-resolution genomic screening of newly diagnosed patients," Leukemia, 2010, 24: 211-215.

Haluska et al., "HomologJus recombination deficiency (HRD) score and niraparib efficacy in high grade ovarian cancer", European Journal of Cancer, 2014, vol. 50 Supplement, pp. 72-73.

Hampton et al., "Simultaneous assessment of loss of heterozygosity at multiple microsatellite loci using semi-automated fluorescence-based detection: subregional mapping of chromosome 4 in cervical carcinoma", Proc. Natl. Acad. Sci. U. S. A., (Jun. 25, 1996), vol. 93, No. 13, pp. 6704-6709, XP055085426.

Hansen et al., "Clinical significance of homologous recombination deficiency score testing in endometrial cancer patients", 2016, ASCO presentation.

Hastings et al., "A Microhomology-Mediated Break-Induced Replication Model for the Origin of Human Copy Number Variation," PLoS Genetics, Jan. 2009, 5(1): 1-9, e1000327.

Hastings et al., "Mechanisms of change in gene copy number," Nat Rev Genet, Aug. 2009, 10(8): 551-564.

Heap et al., "Genome-wide analysis of allelic expression imbalance in human primary cells by high-throughput transcriptome resequencing", Human Molecular Genetics, vol. 19, No. 1, Jan. 1, 2010, pp. 122-134.

Heinsohn, S. et al., "Determination of the prognostic value of loss of heterzygosity at the retinoblastoma gene in osteosarcoma," Int. J. Oncol., May 2007, vol. 30, No. 5, pp. 1205-1214.

Heiser et al., "Subtype and pathway specific responses to anticancer compounds in breast cancer," PNAS, Feb. 2012, 109(8): 2724-2729.

Hendricks et al. "'Recombomice': The past, present, and future of recombination-detection in mice" DNA Repair, vol. 3 No. 10, Oct. 5, 2004, pp. 1255-1261.

Hennessy, Bryan T. J. et al., "Somatic mutations in BRCA1 and BRCA2 could expand the number of patients that benefit from poly (ADP ribose) polymerase inhibitors in ovarian cancer", Journal of Clinical Oncology, (Jul. 6, 2010), vol. 28, No. 22, pp. 3570-3576, XP055070076.

Hodgson et al., "Candidate Biomarkers of PARP Inhibitor Sensitivity in Ovarian Cancer Beyond the BRCA Genes", Br J Cancer . Nov. 2018;119(11):1401-1409.

Holstege et al; BRCA1-mutated and basal-like breast cancers have similar aCGH profiles and a high incidence of protein truncating TP53 mutations; BMC Cancer; 2010; 10:654, 15 pages.

Horiuchi, Akiko, Acta Obstetrica et Gynaecologica Japonica, 2008, vol. 60, No. 11, pp. 1844-1854.

Iafrate et al., "Detection of large-scale variation in the human genome," Nature Genetics, Sep. 2004,36(9): 949-951.

Isakoff et al., "TBCRC009: A Multicenter Phase II Clinical Trial of Platinum Monotherapy With Biomarker Assessment in Metastatic Triple-Negative Breast Cancer," J Clin Oncol, 2015, 1-8.

Jacobs et al., "Genome-wide, High-Resolution Detection of Copy Number, Loss of Heterozygosity, and Genotypes From Formalin-Fixed, Paraffin-Embedded Tumor Tissue Using Microarrays", Cancer Research, 2007, vol. 67, No. 6, pp. 2544-2551.

Janne et al. "High-resolution single-nucleotide polymorphism array and clustering analysis of loss of heterozygosity in human lung cancer cell lines", Oncogene, vol. 23, No. 15, Mar. 29, 2004 (Mar. 29, 2004), pp. 2716-2726.

Johansson et al., "Targeted resequencing of candidate genes using selector probes," Nucleic Acids Research, 2011, 39: 1-13.

Johansson, P. et al., "Abstract 4833: A genomic portrait of tumor progression using next-generation sequencing", Cancer Res., Apr. 15, 2011, vol. 71, p. 4833.

Joosse et al., "Prediction of BRCA1-association in hereditary non-BRCAI/2 breast carcinomas with array-CGH," Breast Cancer Res Treat, 2009, 116:479-489.

Juul et al, Cancer Research, 69(24): 509S-510S (2009). "A Genomic Profile Derived Summary Measure of Chromosomal Breakpoints Predicts Response to Treatment with the DNA-Damaging Agent Cisplatin."

Juul et al., "Amount Of Allelic Imbalance Predicts Response To Cisplatin In Breast And Ovarian Cancer," Annals of Oncology, May 2010, 21: 1 page abstract.

Kaklamani et al., "Phase II neoadjuvant clinical trial of carboplatin and eribulin in women with triple negative early-stage breast cancer (NCT01372579)," Breast Cancer Res Treat, 2015, 151:629-638.

Kalb et al., "Fanconi Anemia: Causes and Consequences of Genetic Instability," Genome Dyn. Basel, Karger, 2006, 1: 218-242.

Kamat et al., "Chemotherapy induced microsatellite instability and loss of heterozygosity in chromosomes 2, 5, 10, and 17 in solid tumor patients," Cancer Cell International, 2014, 14: 118.

Kerangueven et al., "Genome-wide Search for Loss of Heterozygosity Shows Extensive Genetic Diversity of Human Breast Carcinomas", Cancer Research, 57(24):5469-5475 (1997).

Kiialainen et al., "Performance of Microarray and Liquid Based Capture Methods for Target Enrichment for Massively Parallel Sequencing and SNP Discovery," PLoS ONE, Feb. 2011, 6:e16486.

Ko et al., "Frequent loss of heterozygosity on multiple chromosomes in Chinese esophageal squamous cell carcinomas" Cancer Letters, vol. 170, No. 2, pp. 131-138 (2001).

Kolomietz et al., "The Role of Alu Repeat Clusters as Mediators of Recurrent Chromosomal Aberrations in Tumors," Genes, Chromosomes & Cancer, 2002, 35: 97-112.

Kudoh et al., "Gains of 1q21-q22 and 13qI2-qI4 Are Potential Indicators for Resistance to Cisplatin-based Chemotherapy in Ovarian Cancer Patients," Clinical Cancer Research, Sep. 1999, 5:2526-2531.

Kujawski et al., "Genomic complexity identifies patients with aggressive chronic lymphocytic leukemia," Blood, Sep. 2008, 112(5): 1993-2003.

Lakhani et al., "Prediction of BRCA1 Status in Patients with Breast Cancer Using Estrogen Receptor and Basal Phenotype," Clin Cancer Res, Jul. 2005, 11(14): 5175-5180.

Ledermann et al., "Olaparib Maintenance Therapy in Platinum-Sensitive Relapsed Ovarian Cancer," N Engl J Med, 2012, 366: 1382-92.

Lemeta et al., "Loss of Heterozygosity at 6q is Frequent and Concurrent with 3p Loss in Sporadic and Familial Capillary Hemangioblastomas," J. Neuropathol. Exp. Neurol., Oct. 2004, vol. 63, No. 10, pp. 1072-1079.

Leunen et al., "Recurrent Copy Number Alterations in BRCA1-Mutated Ovarian Tumors Alter Biological Pathways," Human Mutation, 2009, 30(12): 1693-702.

Lheureux et al., "Long-term responders of olaparib maintenance in high-grade serous ovarian cancer: Clinical and molecular characterization," Clin Cancer Res. Aug. 1, 2017;23(15):4086-4094. doi: 10.1158/1078-0432.CCR-16-2615. Epub Feb. 21, 2017.

Li et al., "Amplification of LAPTM4B and YWHAZ contributes to chemotherapy resistance and recurrence of breast cancer," Nature Medicine, Feb. 2010, 16(2): 214-219.

Li et al., "Jetset: selecting the optimal microarray probe set to represent a gene," Bioinformatics, 2011, 12: 474.

Li et al., "Major copy proportion analysis of tumor samples using SNP arrays," BMC Bioinformatics, 2008, 9:204, pp. 1-16.

Lin et al. "Integrated analysis of copy number alterations and loss of heterozygosity in human pancreatic cancer using a high-resolution, single nucleotide polymorphism array", Oncology, vol. 75, No. 1-2, Sep. 1, 2008, pp. 102-112.

Loveday et al; Germline mutations in RAD51D confer susceptibility to ovarian cancer; Nat Genet; 2011; 43(9):879-882.

Luo et al., "Cancer predisposition caused by elevated mototic recombination in Bloom mice," Nature Genetics, Dec. 2000, 26: 424-429.

(56) References Cited

OTHER PUBLICATIONS

Maeck et al. "Genetics instability in myelodysplastic syndrome: Detection of microsatellite instability and loss of heterozygosity in bone marrow samples with karyotype alterations" British Journal of Haematology, vol. 109, No. 4, Jun. 2000, pp. 842-846.
Marsit et al; Inactivation of the Fanconi anemia/BRCA pathway in lung and oral cancers: implications for treatment and survival; Oncogene; 2004; 23(4): 1000-1004.
Mateo et al., "Appraising iniparib, the PARP inhibitor that never was—what must we learn?," Nature, Dec. 2013, 10: 688-696.
Matsumoto et al., "Allelic imbalance at 1P36 may predict prognosis of chemoradiation therapy for bladder preservation in patients with invasive bladder cancer", British Journal of Cancer, vol. 91, No. 6, pp. 1025-1031 (2004).
McVean, "What drives recombination hotspots to repeat DNA in humans?," Phil. Trans. R. Soc. B, 2010,365:1213-1218.
Meadows et al. "Genome-wide analysis of loss of heterozygosity and copy number amplification in uterine leiomyomas using the 100K single nucleotide polymorphism array", Experimental and Molecular Pathology, vol. 91, No. 1, Apr. 8, 2011, pp. 434-439, XP028239924, ISSN: 0014-4800, DOI: 10.1016/J.YEXMP.2011.03.007 [retrieved on Apr. 8, 2011].
Medri et al., "Prognostic Relevance of Mitotic Activity in Patients With Node-Negative Breast Cancer", Modern Pathology, 2003, 16(11):1067-1075.
Mei et al., "Genome-wide Detection of Allelic Imbalance Using Human SNPs and High-density DNA Arrays," Genome Research, 2000, 10: 1126-1137.
Meindl, Alfons et al., "Germline mutations in breast and ovarian cancer pedigrees establish RAD51C as a human cancer susceptibility gene," Nature Genetics, May 2010,42(5):410-416.
Mendes-Pereira et al; Synthetic lethal targeting of PTEN mutant cells with PARP inhibitors; EMBO Mol Med; 2009; 1 (6-7): 315-322.
Mills et al., Homologous Recombination Deficiency (HRD) Score Shows Superior Association with Outcome Compared to its Individual Score Components (LOH, TAI, and LST Scores) in Platinum Treated Serous Ovarian Cancer, Annual Meeting on Women's Cancer, 2016, pp. 1-19.
Mukhopadhyay et al., "Clinicopathological Features of Homologous Recombination-Deficient Epithelial Ovarian Dancers: Sensitivity to PARP Inhibitors, Platinum, and Survival," Cancer Research, 2012, 5675-5682.
Murayama-Hosokawa, S. et al., "Genome-wide single-nucleotide polymorphism arrays in endometrial carcinomas associate extensive chromosomal instability with poor prognosis and unveil frequent chromosomal imbalances involved in the PI3-kinase pathway," Oncogene, Apr. 1, 2010, vol. 29, No. 13, pp. 1897-1908.
Nannya et al; A robust algorithm for copy number detection using high-density oligonucleotide single nucleotide polymorphism genotyping arrays; Cancer Res; 2005; 65(14):6071-6079.
Narayan et al; "Frequent promoter of methylation of CDH1, DAPK, RARB, and HIC1 genes in carcinoma of cervix uteri: its relationship to clinical outcome"; Mol Cancer; 2003; 2:24, 12 pages.
Norquist et al; Secondary somatic mutations restoring BRCA1/2 predict chemotherapy resistance in hereditary ovarian carcinomas; J Clin Oncol;2011; 29(22): 3008-3015.
Novak et al., "A high-resolution allelotype of B-cell chronic lymphocytic leukemia (B-CLL)," Blood, Sep. 2002, 100(5): 1787-1794.
O'Brien et al., "Converting cancer mutations into therapeutic opportunities," EMBO Mol. Med. 1:297-299 (2009).
O'Shaugnessy et al; Iniparib plus chemotherapy in metastatic triple-negative breast cancer; N Engl J Med; 2011; 364 (3):205-214.
Ogston et al., "A new histological grading system to assess response of breast cancers to primary chemotherapy: prognostic significance and survial," The Breast, 2003, 12: 320-327.
Osborne and Hamshere, "A Genome-wide Map Showing Common Regions of Loss of Heterozygosity/Allelic Imbalance in Breast Cancer," Cancer Res, 2000, 60: 3706-3712.
Ott et al., Clinical Cancer Research, The American Association for Cancer Research, US, 9(6):2307-2315 (2003). "Chromosomal instability rather than p53 mutation is associated: with response to neoadjuvant cisplatin-based chemotherapy in gastric carcinoma".
Patel et al., "Failure of Iniparib to Inhibit Poly(ADP-Ribose) Polymerase in Vitro," Clin Cancer Res, Mar. 2012, 1655-1662.
Patocs, A. et al., "Breast-cancer stromal cells with TP53 mutations and nodal metastases", N. Engl. J. Med., 2007, vol. 357, pp. 2543-2551.
Peng et al., "Genome-wide transcriptome profiling of homologous recombination DNA repair," Nature Communications 2014, 1-11.
Penning et al. "Discovery and SAR of 2-(1-propylpiperidin-4-y1)-1H-benzimidazole-4-carboxamide: A potent inhibitor of poly(ADP-ribose) polymerase (PARP) for the treatment of cancer", Bioorganic & Medicinal Chemistry, Pergamon, GB, vol. 16, No. 14, Jul. 15, 2008, pp. 6965-6975.
Pfeifer et al. "Genome-wide analysis of DNA copy number changes and LOH in CLL using high-density SNP arrays", Blood, vol. 109, No. 3, Oct. 5, 2006 (Oct. 5, 2006), pp. 1202-1210.
Popova et al. "Genome Alteration Print (GAP): a tool to visualize and mine complex cancer genomic profiles obtained by SNP arrays", Genome Biology, Biomed Central Ltd., London, GB, vol. 10, No. 11, Nov. 11, 2009, p. R128.
Popva et al., "Ploidy and Large-Scale Genomic Instability Consistently Identify Basal-like Breast Carcinomas with BRCAI/2 Inactivation," Cancer Research, Nov. 1, 2012, 72(21); 5454-62.
Puliti et al., Mutat Res. 686(1-2):74-83 (2010). "Low-copy repeats on chromosome 22q11.2 show replication timing switches, DNA flexibility peaks and stress inducible asynchrony, sharing instability features with fragile sites."
Rakha et al., "Basal-Like Breast Cancer: A Critical Review," Journal of Clinical Oncology, May 2008, 26(15): 2568-2581.
Ramirez, C. et al., "Loss of 1p, 19q, and 10q heterozygosity prospectively predicts prognosis of oligodendroglial tumors-towards individualized tumor treatment?" Neuro. Oncol., May 2010, vol. 12, No. 5, pp. 490-499.
Richard et al., "Comparative Genomics and Molecular Dynamics of DNA Repeats in Eukaryotes," Microbiology and Molecular Biology Reviews, Dec. 2008, 686-727.
Richardson et al., "X chromosomal abnormalities in basal-like human breast cancer," Cancer Cell, Feb. 2006, 9:121-132.
Roscillli et al., Annual Meeting of the American Association for Cancer Research, Apr. 17-21, 2010, No. 685, 5 pages.
Ross et al., "Comprehensive next-generation sequencing for clinically actionable mutations from formalin-fixed cancer tissues," Journal of Clinical Oncology, 2011, 15 Supp: 1-3, abstract.
Ryan et al, 2009 ASCO Annual Meeting, http://meetinglibrary.asco.org/content/34135-65, (2009). "Neoadjuvant cisplatin and bevacizumab in triple negative breast cancer (TNBC): Safety and efficacy."
Sakai et al; Functional resoration of BRCA2 protein by secondary BRCA2 mutations in BRCA2-mutated ovarian carcinoma; Cancer Res; 2009; 69(16):6381-6386.
Sakai et al; Secondary mutations as a mechanism of cisplatin resistance in BRCA2-mutated cancers; Nature; 2008; 451(7182):1116-1120.
Samouelian et al., "Chemosensitivity and radiosensitivity profiles of four new human epithelial ovarian cancer cell lines exhibiting genetic alterations in BRCA2 TGFB-RII KRAS2 TP53 and/or CDNK2A," Cancer Chemother Pharmacol, 2004, 54: 497-504.
Sandhu et al., "The poly(ADP-ribose) polymerase inhibitor niraparib (MK4827) in BRCA mutation carriers and patients with sporadic cancer: a phase 1 dose-escalation trial," Lancet Oncology, 14(9):882-92, Aug. 2013.
Santana-Davila et al. , "Treatment Options for Patients With Triple-Negative Breast Cancer", Journal of Hematology & Oncology, 3:42 (Oct. 27, 2010).
Schouten et al., "Challengers in the Use of DNA Repair Deficiency As a Biomarker in Breast Cancer," Journal of Clinical Oncology, 2015, 33(17): 1867-1869.
Schwartz et al., "Homologous recombination and nonhomologous end-joining repair pathways regulate fragile site stability," Genes & Development, 2005, 19: 2715-2726.

(56) References Cited

OTHER PUBLICATIONS

Schweiger et al., "Genome-Wide Massively Parallel Sequencing of Formaldehyde Fixed-Paraffin Embedded (FFPE) Tumor Tissues for Copy-Number- and Mutation-Analysis," PLoS ONE, 2009, 4: e5548.
Sebat et al., "Large-Scale Copy Number Polymorphism in the Human Genome," Science, Jul. 2004, 305:525-528.
Shanda et al., "Homologous Recombination Deficiency (HRD) in Patients with Pancreatic Cancer and Response to Chemotherapy", 2017, ASCO presentation.
Silva et al., "Loss of heterozygosity in BRCA1 and BRCA2 markers and high-grade malignancy in breast cancer", Breast Cancer Res. Treat, (Jan. 1999), vol. 53, No. 1, pp. 9-17, XP055076352.
Silver et al. "Efficacy of Neoadjuvant Cisplatin in Triple-Negative Breast Cancer", J. Clin. Oncol. vol. 28, 2010, pp. 1145-1153.
Silver et al., "Further evidence for BRCA1 communication with the inactive X chromosome," Cell, Mar. 2007, 128(5): 991-1002.
Smid et al. "Patterns and incidence of chromosomal instability and their prognostic relevance in breast cancer subtypes", Breast Cancer Research and Treatment, Kluwer Academic Publishers, BO, vol. 128, No. 1, Jul. 15, 2010, pp. 23-30, XP019916000, ISSN: 1573-7217DOI: 10.1007/S10549-010-1026-5.
Sorlie et al., "Repeated observation of breast tumor subtypes in independent gene expression data sets," PNAS, Jul. 2003, 100(14): 8418-8423.
Soule et al., "Isolation and Characterization of a Spontaneously Immortalized Human Breast Epithelial Cell Line, MCF-10," Cancer Research, Sep. 15, 1990, 50: 6075-6086.
Stankiewicz et al., "Genome Architectre Catalyzes Nonrecurrent Chromosomal Rearrangements," Am. J. Hum. Genet., 2003, 72:1101-1116.
Stefansson et al; Genomic profiling of breast tumours in relation to BRCA abnormalities and phenotypes; Breast Cancer Res; 2009; 11(4):R47, 14 pages.
Stronach et al., "Biomarker Assessment of HR Deficiency, Tumor BRCA1/2 Mutations, and CCNE1 Copy Number in Ovarian Cancer: Associations with Clinical Outcome Following Platinum Monotherapy," Mol Cancer Res. Jul. 2018;16(7):1103-1111. doi: 10.1158/1541-7786.MCR-18-0034. Epub May 3, 2018.
Swisher et al., "Secondary BRCA1 mutations in BRCAI-mutated ovarian carcinomas with platinum resistance," Cancer Res., Apr. 2008, 68(8): 2581-2586.
Tai et al., "High-Throughput Loss-of-Heterozygosity Study of Chromosome 3p in Lung Cancer Using Single-Nucleotide Polymorphism Markers", Cancer Research, vol. 66, No. 8, Apr. 15, 2006, pp. 4133-4138.
Takahashi, Clinical Cancer Research, 13(1): 111-120 (2007). "Clonal and Parallel Evolution of Primary Lung Cancers and Their Metastases Revealed by Molecular Dissection of Cancer Cells."
Tan et al; 'BRCAness' syndrome in ovarian cancer: a case-control study describing the clinical features and outcome of patients with epithelial ovarian cancer associated with BRCA1 and BRCA2 mutations; J Clin Oncol; 2008; 26 (34):5530-5536.
Tassone et al., "BRCAI expression modulates chemosensitivity of BRCAI-defective HCCI937 human breast cancer cells," British Journal of Cancer, 2003, 88: 1285-1291.
Teh et al.: "Genomewide Single Nucleotide Polymorphism Microarray Mapping in Basal Cell Carcinomas Unveils Uniparental Disomy as a Key Somatic Event", Cancer Research, vol. 65, No. 19, Oct. 1, 2005 (Oct. 1, 2005), pp. 8597-8603, XP002703167.
Telli et al., "Abstract PD09-04: Homologous Recombination Deficiency (HRD) score predicts pathologic response following neoadjuvant platinum-based therapy in triple-negative and BRCA1/2 mutation-associated breast cancer (BC)", Cancer Research, (Dec. 15, 2012), URL: http://cancerres.aacrjournals.org/content/72/24_Supplement/PD09-04, (Oct. 19, 2016), XP055312264.
Telli et al., "Phase II Study of Gemcitabine, Carboplatin, and Iniparib As Neoadjuvant Therapy for Triple-Negative and BRCA1/2 Mutation-Associated Breast Cancer With Assessment of a Tumor-Based Measure of Genomic Instability: PrECOG0105," J Clin Oncol, 2015, 1-7.

Timms et al., "Abstract P6-05-10: Association between BRCA 1/2 status and DNA-based assays for homologous recombination deficiency in breast cancer", Dec. 2013, Abstracts: Thirty-Sixth Annual CTRC-AACR San Antonio, Texas, Breast Cancer Symposium—Dec. 10-14, 2013, 2 pages.
Timms et al., "Association of BRCA 712 defects with genomic scores predictive of DNA damage repair deficiency among breast cancer subtypes," Breast Cancer Research, 2014, 16: 1-9.
Timms et al., "DNA repair deficiences in ovarian cancer: Genomic analysis of high grade serous ovarian tumors from the NOVA Study", 2015, ESMO presentation, 1 page.
Timms et al., "The Molecular Landscape of Genome Instability in Prostate Cancer", 2015, ESMO presentation, 1 page.
Tommasi et al., "655Val and 1170Pro ERBB2 SNPs in familial breast cancer risk and BRCA1 alterations," Cellular Oncology, 2007, 29: 241-248.
Tseng, R. C et al., Genomewide loss of heterozygosity and its clinical associations in non-small cell lung cancer, Int. J. Cancer, Nov. 1, 2005, vol. 117, No. 2, pp. 241-247.
Tuna et al. , "Association between Acquired Uniparental Diomy and Homozygous Mutations and HER2/ER/PR Status in Breast Cancer", PLoS One , 2010, vol. 5, No. 11, e15094.
Turner et al., "BRCA1 dysfunction in sporadic basal-like breast cancer," Oncogene, 2007, 26: 2126-2132.
Valeri A et al.: "High frequency of allelic losses in high-grade prostate cancer is associated with biochemical progression after radical prostatctomy", Urologic Oncology, Elsevier, New York, NY, US, vol. 23, No. 2, Mar. 1, 2005, pp. 87-92, XP027799195, ISSN: 1078-1439 [retrieved on Mar. 1, 2005].
Van Loo et al., "Allele-specific copy No. analysis of tumors," PNAS, 2010, 107(39): 16910-16915.
Varley et al., "Nested Patch PCR enables highly multiplexed mutation discovery in candidate genes," Genome Research, 2008, 18: 1844-1850.
Volchenboum et al. "Comparison of Primary Neuroblastoma Tumors and Derivative Early-Passage Cell Lines Using Genome-Wide Single Nucleotide Polymorphism Array Analysis", Cancer Research, vol. 69, No. 10, May 12, 2009, pp. 4143-4149.
Vollebergh et al., "Genomic instability in breast and ovarian cancers: Translation into clinical predictive biomarkers," Cell. Mol. Life Sciences CMLS, 69(2):223-245, Sep. 2011.
Vrieling, "Mitotic maneuvers in the light," Nature Genetics, 28:101-102, Jun. 1, 2001.
Walsh, C.S. et al., "Genome-Wide loss of Heterozygosity and Uniparental Disomy in BRCA1/2-Associated Ovarian Carcinomas", Clin Cancer Res, 14(23):7645 (Dec. 1, 2008).
Wang et al., "Analysis of molecular inversion probe performance for allele copy number determination," Genome Biol, 2007, 8(11):R246.
Wang et al., "Loss of heterozygosity and its correlation with expression profiles in subclasses of invasive breast cancers," Cancer Res, Jan. 2004, 64(1): 64-71.
Wilcox et al; High-resolution methylation analysis of the BRCA1 promoter in ovarian tumors; Cancer Genet Cytogenet; 2005; 159(2): 114-122.
Wilcoxen et al., "Homologous recombination deficiency (HRD) score enriches for niraparib sensitive high grade ovariar tumors," Supplemental Abstract, 2015, 1 page.
Wilcoxen et al., "Use of homologous recombination deficiency (HRD) score to enrich for niraparib sensitive high grade ovarian tumors," J Clin Oncol, 2015, Supplemental Abstract: 5532, 2 pages.
Xiao et al., "The XIST Noncoding RNA Functions Independently of BRCA1 in X Inactivation," Cell, Mar. 2007, 128:977-989.
Xu et al., "Centrosome amplification and a defective G2-M cell cycle checkpoint induce genetic instability in BRCA1 Exon 11 Isoform-deficient cells," Molecular Cell, 1999, 3:389-395.
Yang et al., "Reconstitution of caspase 3 sensitizes MCF-7 breast cancer cells to doxorubicin- and etoposide-induced apoptosis," Cancer Res, Jan. 2001, 61(1): 348-54.
Yaris et al., "Primary cerebral neuroblastoma: a case treated with adjuvant chemotherapy and radiotherapy," The Turkish Journal of Pediatrics, 2004; 46: 182-185.

(56) References Cited

OTHER PUBLICATIONS

Zhao et al., "Systematic detection of putative tumor suppressor genes through the combined use of exome and transcriptome sequencing", Genome Biol., 2010, vol. 11: R114, pp. 1-14.
Zuchner et al., "Linkage and association study of late-onset Alzheimer disease families linked to 9p21.3," Ann Hum Genet, Nov. 2008,72(Pt 6): 725.

* cited by examiner

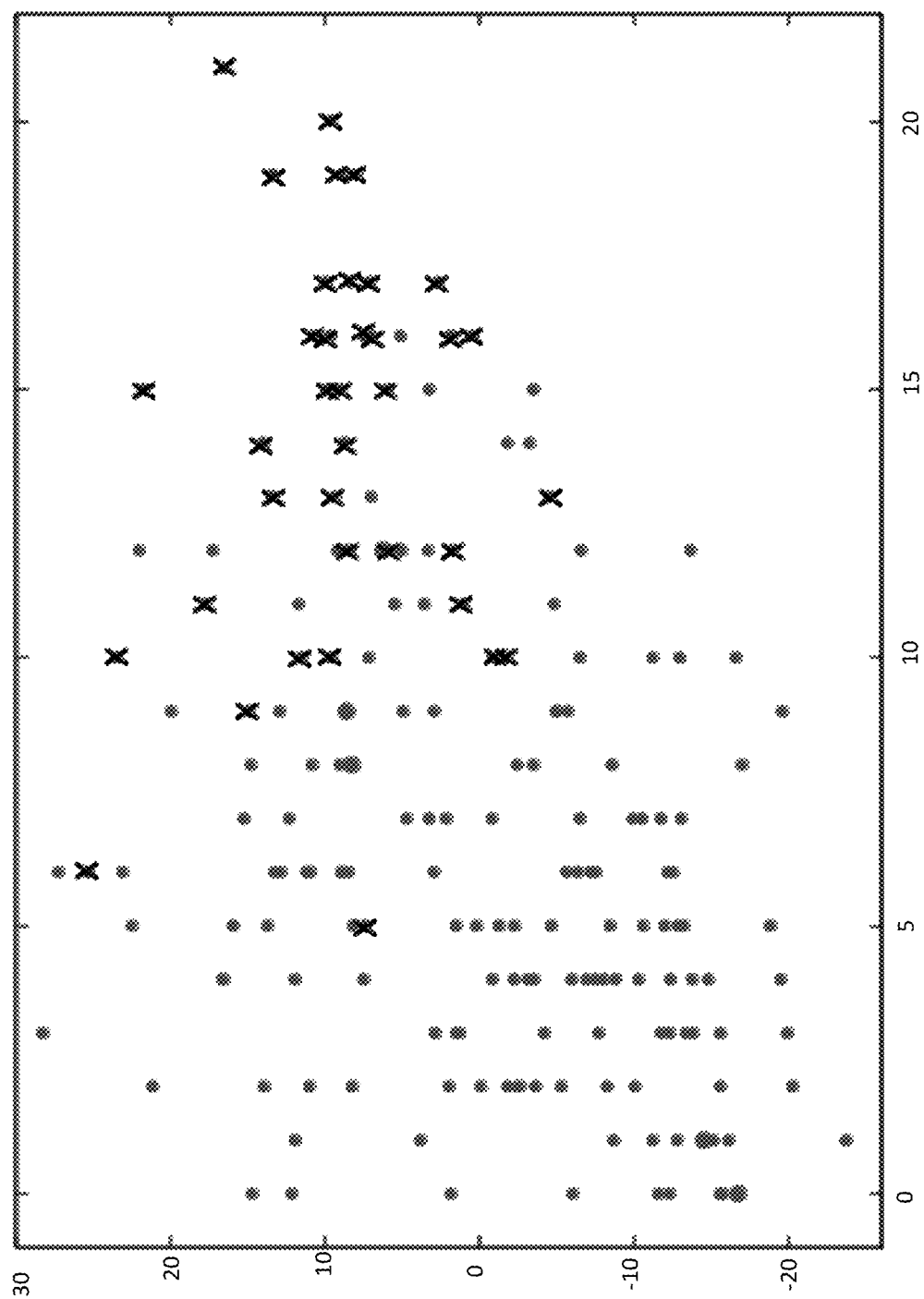

METHODS AND MATERIALS FOR ASSESSING HOMOLOGOUS RECOMBINATION DEFICIENCY

RELATED APPLICATIONS

This application is a continuation of and claims the priority benefit of U.S. utility application Ser. No. 15/433,249, filed Feb. 15, 2017, which claims benefit to International Application serial number PCT/US2015/045561 filed Aug. 17, 2015, which in turn claims the priority benefit of U.S. provisional application Ser. No. 62/037,764, filed Aug. 15, 2014 and U.S. utility application Ser. No. 14/507,412, filed Oct. 6, 2014, the entire contents of each of which are hereby incorporated by reference.

BACKGROUND

Cancer is a serious public health problem, with 562,340 people in the United States of America dying of cancer in 2009 alone. *American Cancer Society, Cancer Facts & Figures* 2009 (available at American Cancer Society website). One of the primary challenges in cancer treatment is discovering relevant, clinically useful characteristics of a patient's own cancer and then, based on these characteristics, administering a treatment plan best suited to the patient's cancer. While strides have been made in this field of personalized medicine, there is still a significant need for better molecular diagnostic tools to characterize patients' cancers.

SUMMARY

This document relates to methods and materials involved in assessing samples (e.g., cancer cells or nucleic acids derived therefrom) for homologous recombination deficiency (HRD) (e.g., an HRD signature) based on detection of particular chromosomal aberrations ("CA"). For example, this document provides methods and materials for detecting CA Regions to determine whether or not a cell (e.g., a cancer cell) has HRD (e.g., exhibits an HRD signature). This document also provides materials and methods for identifying cancer patients likely to respond to a particular cancer treatment regimen based on the presence, absence, or severity of HRD. Throughout this document, unless indicated otherwise, HRD and homology-dependent repair (HDR) deficiency are used synonymously.

In general, one aspect of this invention features a method for assessing HRD in a cancer cell or DNA (e.g., genomic DNA) derived therefrom. In some embodiments, the method comprises, or consists essentially of, (a) detecting, in a sample or DNA derived therefrom, CA Regions (as defined herein) in at least one pair of human chromosomes of sample or DNA derived therefrom (e.g., any pair of human chromosomes other than a human X/Y sex chromosome pair); and (b) determining the number, size (e.g., length), and/or character of said CA Regions. In some embodiments, CA Regions are analyzed in a number of chromosome pairs that are representative of the entire genome (e.g., enough chromosomes are analyzed such that the number and size of CA Regions are expected to be representative of the number and size of CA Regions across the genome).

Various aspects of the present invention involve using a combined analysis of two or more types of CA Regions to assess (e.g., detect) HRD in a sample. Three types of CA Regions useful in such methods include (1) chromosomal regions showing loss of heterozygosity ("LOH Regions", as defined herein), (2) chromosomal regions showing telomeric allelic imbalance ("TAI Regions", as defined herein), and (3) chromosomal regions showing large scale transition ("LST Regions", as defined herein). CA Regions of a certain size, chromosomal location or character (e.g., "Indicator CA Regions", as defined herein) can be particularly useful in the various aspects of the invention described herein.

Thus in one aspect the invention provides a method of assessing (e.g., detecting) HRD in a sample comprising (1) determining the total number of LOH Regions of a certain size or character (e.g., "Indicator LOH Regions", as defined herein) in the sample; (2) determining the total number of TAI Regions of a certain size or character (e.g., "Indicator TAI Regions", as defined herein) in the sample; and (3) assessing HRD in the sample based at least in part on the determinations made in (1) and (2). In another aspect the invention provides a method of assessing (e.g., detecting) HRD in a sample comprising (1) determining the total number of LOH Regions of a certain size or character (e.g., "Indicator LOH Regions", as defined herein) in the sample; (2) determining the total number of LST Regions of a certain size or character (e.g., "Indicator LST Regions", as defined herein) in the sample; and (3) assessing HRD in the sample based at least in part on the determinations made in (1) and (2). In another aspect the invention provides a method of assessing (e.g., detecting) HRD in a sample comprising (1) determining the total number of TAI Regions of a certain size or character (e.g., "Indicator TAI Regions", as defined herein) in the sample; (2) determining the total number of LST Regions of a certain size or character (e.g., "Indicator LST Regions", as defined herein) in the sample; and (3) assessing HRD in the sample based at least in part on the determinations made in (1) and (2). In another aspect the invention provides a method of assessing (e.g., detecting) HRD in a sample comprising (1) determining the total number of LOH Regions of a certain size or character (e.g., "Indicator LOH Regions", as defined herein) in the sample; (2) determining the total number of TAI Regions of a certain size or character (e.g., "Indicator TAI Regions", as defined herein) in the sample; (3) determining the total number of LST Regions of a certain size or character (e.g., "Indicator LST Regions", as defined herein) in the sample; and (4) assessing (e.g., detecting) HRD in the sample based at least in part on the determinations made in (1), (2) and (3).

In one aspect the invention provides a method of diagnosing the presence or absence of HRD in a patient sample, the method comprising (1) analyzing (e.g., assaying) one or more patient samples to determine (e.g., detect) the total number of LOH Regions of a certain size or character (e.g., "Indicator LOH Regions", as defined herein) in the sample; (2) analyzing (e.g., assaying) one or more patient samples to determine (e.g., detect) the total number of TAI Regions of a certain size or character (e.g., "Indicator TAI Regions", as defined herein) in the sample; and either (3)(a) diagnosing the presence of HRD in a patient sample where the number from (1) and/or the number from (2) exceeds some reference; or (3)(b) diagnosing the absence of HRD in a patient sample where neither the number from (1) nor the number from (2) exceeds some reference. In another aspect the invention provides a method of diagnosing the presence or absence of HRD in a patient sample, the method comprising (1) analyzing (e.g., assaying) one or more patient samples to determine (e.g., detect) the total number of LOH Regions of a certain size or character (e.g., "Indicator LOH Regions", as defined herein) in the sample; (2) analyzing (e.g., assaying) one or more patient samples to determine (e.g., detect) the total number of LST Regions of a certain size or character (e.g., "Indicator LST Regions", as defined herein) in the sample; and either (3)(a) diagnosing the presence of HRD in a patient sample where the number from (1) and/or the number from (2) exceeds some reference; or (3)(b) diagnosing the absence of HRD in a patient sample where neither the number from (1) nor the number from (2) exceeds some reference. In another aspect the invention provides a method of diagnosing the presence or absence of HRD in a patient sample, the method comprising (1) analyzing (e.g., assaying) one or more patient samples to determine (e.g., detect) the total number of TAI Regions of a certain size or character (e.g., "Indicator TAI Regions", as defined herein) in the sample; (2) analyzing (e.g., assaying) one or more patient samples to determine (e.g., detect) the total number of LST Regions of a certain size or character (e.g., "Indicator LST Regions", as defined herein) in the sample; and either (3)(a) diagnosing the presence of HRD in a patient sample where the number from (1) and/or the number from (2) exceeds some reference; or (3)(b) diagnosing the absence of HRD in a patient sample where neither the number from (1) nor the number from (2) exceeds some reference. In another aspect the invention provides a method of diagnosing the presence or absence of HRD in a patient sample, the method comprising (1) analyzing (e.g., assaying) one or more patient samples to determine (e.g., detect) the total number of LOH Regions of a certain size or character (e.g., "Indicator LOH Regions", as defined herein) in the sample; (2) analyzing (e.g., assaying) one or more patient samples to determine (e.g., detect) the total number of TAI Regions of a certain size or character (e.g., "Indicator TAI Regions", as defined herein) in the sample; (3) analyzing (e.g., assaying) one or more patient samples to determine (e.g., detect) the total number of LST Regions of a certain size or character (e.g., "Indicator LST Regions", as defined herein) in the sample; and either (3)(a) diagnosing the presence of HRD in a patient sample where the number from (1), the number from (2) and/or the number from (3) exceeds some reference; or (3)(b) diagnosing the absence of HRD in a patient sample where none of the numbers from (1), (2) or (3) exceeds some reference.

Various aspects of the present invention involve using an average (e.g., arithmetic mean) of three types of CA Regions to assess (e.g., detect) HRD in a sample. Three types of CA Region useful in such methods include (1) chromosomal regions showing loss of heterozygosity ("LOH Regions", as defined herein), (2) chromosomal regions showing telomeric allelic imbalance ("TAI Regions", as defined herein), and (3) chromosomal regions showing large scale transition ("LST Regions", as defined herein). CA Regions of a certain size or character (e.g., "Indicator CA Regions", as defined herein) can be particularly useful in the various aspects of the invention described herein. Thus in one aspect the invention provides a method of assessing (e.g., detecting) HRD in a sample comprising (1) determining the total number of LOH Regions of a certain size or character (e.g., "Indicator LOH Regions", as defined herein) in the sample; (2) determining the total number of TAI Regions of a certain size or character (e.g., "Indicator TAI Regions", as defined herein) in the sample; (3) determining the total number of LST Regions of a certain size or character (e.g., "Indicator LST Regions", as defined herein) in the sample; (4) calculating the average (e.g., arithmetic mean) of the determinations made in (1), (2), and (3); and (5) assessing HRD in the sample based at least in part on the calculated average (e.g., arithmetic mean) made in (4).

In some embodiments assessing (e.g., detecting) HRD is based on a score derived or calculated from (e.g., representing or corresponding to) the detected CA Regions ("CA Region Score", as defined herein). Scores are described in greater detail herein. In some embodiments HRD is detected if a CA Region Score for a sample exceeds some threshold (e.g., a reference or index CA Region Score), and optionally HRD is not detected if the CA Region Score for the sample does not exceed some threshold (e.g., a reference or index CA Region Score, which may in some embodiments be the same threshold for positive detection). Those skilled in the art will readily appreciate that scores can be devised in the opposite orientation within this disclosure (e.g., HRD is detected if the CA region Score is below a certain threshold and not detected if the score is above a certain threshold).

In some embodiments the CA Region Score is a combination of scores derived or calculated from (e.g., representing or corresponding to) two or more of (1) the detected LOH Regions ("LOH Region Score", as defined herein), (2) the detected TAI Regions ("TAI Region Score", as defined herein), and/or (3) the detected LST Regions ("LST Region Score", as defined herein). In some embodiments the LOH Region Score and TAI Region Score are combined as follows to yield a CA Region Score:

$$\text{CA Region Score} = A^*(\text{LOH Region Score}) + B^*(\text{TAI Region Score})$$

In some embodiments the LOH Region Score and TAI Region Score are combined as follows to yield a CA Region Score:

$$\text{CA Region Score} = 0.32^*(\text{LOH Region Score}) + 0.68^*(\text{TAI Region Score})$$

In some embodiments the LOH Region Score and LST Region Score are combined as follows to yield a CA Region Score:

$$\text{CA Region Score} = A^*(\text{LOH Region Score}) + B^*(\text{LST Region Score})$$

In some embodiments the TAI Region Score and LST Region Score are combined as follows to yield a CA Region Score:

$$\text{CA Region Score} = A^*(\text{TAI Region Score}) + B^*(\text{LST Region Score})$$

In some embodiments the LOH Region Score, TAI Region Score and LST Region Score are combined as follows to yield a CA Region Score:

$$\text{CA Region Score} = A^*(\text{LOH Region Score}) + B^*(\text{TAI Region Score}) + C^*(\text{LST Region Score})$$

In some embodiments the LOH Region Score, TAI Region Score and LST Region Score are combined as follows to yield a CA Region Score:

$$\text{CA Region Score} = 0.21^*(\text{LOH Region Score}) + 0.67^*(\text{TAI Region Score}) + 0.12^*(\text{LST Region Score})$$

In some embodiments the CA Region Score is a combination of scores derived or calculated from (e.g., representing or corresponding to) the average (e.g., arithmetic mean) of (1) the detected LOH Regions ("LOH Region Score", as defined herein), (2) the detected TAI Regions ("TAI Region Score", as defined herein), and/or (3) the detected LST Regions ("LST Region Score", as defined herein) to yield a CA Region Score:

$$\text{CA Region Score} = A^*(\text{LOH Region Score}) + B^*(\text{TAI Region Score}) + C^*(\text{LST Region Score})/3$$

In another aspect, the present invention provides a method of predicting the status of BRCA1 and BRCA2 genes in a sample. Such method is analogous to the methods described above and differs in that the determination of CA Regions, LOH Regions, TAI Regions, LST Regions, or scores incorporating these are used to assess (e.g., detect) BRCA1 and/or BRCA2 deficiency in the sample. In another aspect, this invention provides a method of predicting a cancer patient's response to a cancer treatment regimen comprising a DNA damaging agent, an anthracycline, a topoisomerase I inhibitor, radiation, and/or a PARP inhibitor. Such method is analogous to the methods described above and differs in that the determination of CA Regions, LOH Regions, TAI Regions, LST Regions, or scores incorporating these are used to predict the likelihood that the cancer patient will respond to the cancer treatment regimen. In some embodiments, the patients are treatment naïve patients. In another aspect, this invention provides a method of treating cancer. Such method is analogous to the methods described above and differs in that a particular treatment regimen is administered (recommended, prescribed, etc.) based at least in part on the determination of CA Regions, LOH Regions, TAI Regions, LST Regions, or scores incorporating these. In another aspect, this invention features the use of one or more drugs selected from the group consisting of DNA damaging agents, anthracyclines, topoisomerase I inhibitors, and PARP inhibitors, in the manufacture of a medicament useful for treating a cancer in a patient identified as having (or as having had) a cancer cell determined to have HRD (e.g., an HRD signature) as described herein. In another aspect, this document features a method for assessing a sample for the presence of a mutation within a gene from an HDR pathway. Such method is analogous to the methods described above and differs in that the determination of CA Regions, LOH Regions, TAI Regions, LST Regions, or scores incorporating these are used to detect (or not) the presence of a mutation within a gene from an HDR pathway.

In another aspect, the invention provides a method for assessing a patient. The method comprises, or consists essentially of, (a) determining whether the patient has (or had) cancer cells with more than a reference number of CA Regions (or, e.g., a CA Region Score exceeding a reference CA Region Score); and (b)(1) diagnosing the patient as having cancer cells with HRD if it is determined that the patient has (or had) cancer cells with more than a reference number of CA Regions (or, e.g., a CA Region Score exceeding a reference CA Region Score); or (b)(2) diagnosing the patient as not having cancer cells with HRD if it is determined that the patient does not have (or has not had) cancer cells with more than a reference number of CA Regions (or, e.g., the patient does not have (or has not had) cancer cells with a CA Region Score exceeding a reference CA Region Score).

In another aspect, this invention features the use of a plurality of oligonucleotides capable of hybridizing to a plurality of polymorphic regions of human genomic DNA, in the manufacture of a diagnostic kit useful for determining the total number or combined length of CA Regions in at least a chromosome pair (or DNA derived therefrom) in a sample obtained from a cancer patient, and for detecting (a) HRD or likelihood of HRD (e.g., an HRD signature) in the sample, (b) deficiency (or likelihood of deficiency) in a BRCA1 or BRCA2 gene in the sample, or (c) an increased likelihood that the cancer patient will respond to a cancer treatment regimen comprising a DNA damaging agent, an anthracycline, a topoisomerase I inhibitor, radiation, or a PARP inhibitor.

In another aspect, this invention features a system for detecting HRD (e.g., an HRD signature) in a sample. The system comprises, or consists essentially of, (a) a sample analyzer configured to produce a plurality of signals about genomic DNA of at least one pair of human chromosomes (or DNA derived therefrom) in the sample, and (b) a computer sub-system programmed to calculate, based on the plurality of signals, the number or combined length of CA Regions in the at least one pair of human chromosomes. The computer sub-system can be programmed to compare the number or combined length of CA Regions to a reference number to detect (a) HRD or likelihood of HRD (e.g., an HRD signature) in the sample, (b) deficiency (or likelihood of deficiency) in a BRCA1 or BRCA2 gene in the sample, or (c) an increased likelihood that the cancer patient will respond to a cancer treatment regimen comprising a DNA damaging agent, an anthracycline, a topoisomerase I inhibitor, radiation, or a PARP inhibitor. The system can comprise an output module configured to display (a), (b), or (c). The system can comprise an output module configured to display a recommendation for the use of the cancer treatment regimen.

In another aspect, the invention provides a computer program product embodied in a computer readable medium that, when executing on a computer, provides instructions for detecting the presence or absence of any CA Region along one or more of human chromosomes other than the human X and Y sex chromosomes (the CA Regions optionally being Indicator CA Regions); and determining the total number or combined length of the CA Regions in the one or more chromosome pairs. The computer program product can include other instructions.

In another aspect, the present invention provides a diagnostic kit. The kit comprises, or consists essentially of, at least 500 oligonucleotides capable of hybridizing to a plurality of polymorphic regions of human genomic DNA (or DNA derived therefrom); and a computer program product provided herein. The computer program product can be embodied in a computer readable medium that, when executing on a computer, provides instructions for detecting the presence or absence of any CA Region along one or more of human chromosomes other than the human X and Y sex chromosomes (the CA Regions optionally being Indicator CA Regions); and determining the total number or combined length of the CA Regions in the one or more chromosome pairs. The computer program product can include other instructions.

In some embodiments of any one or more of the aspects of the invention described in the preceding paragraphs, any one or more of the following can be applied as appropriate. The CA Regions can be determined in at least two, five, ten, or 21 pairs of human chromosomes. The cancer cell can be an ovarian, breast, lung or esophageal cancer cell. The reference can be 6, 7, 8, 9, 10, 11, 12, 13, 14, 15, 16, 17, 18 or 20 or greater. The at least one pair of human chromosomes can exclude human chromosome 17. The DNA damaging agent can be cisplatin, carboplatin, oxalaplatin, or picoplatin, the anthracycline can be epirubincin or doxorubicin, the topoisomerase I inhibitor can be campothecin, topotecan, or irinotecan, or the PARP inhibitor can be iniparib, olaparib or velapirib. The patient can be a treatment naïve patient.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the description and accompanying drawings below. The materials, methods, and examples are illustrative only and not intended to be limiting. Other features, objects, and advantages of the invention will be apparent from the description and drawings, and from the claims.

DESCRIPTION OF THE DRAWINGS

FIG. 7F shows TAI vs LST for patients as analyzed in Example 2 herein. X axis: TAI score; Y axis: LST score; red dots: intact samples; blue dots (with a super imposed "X"): BRCA1/2 deficient samples. The area under the dots is proportional to the number of samples with that combination of TAI and LST scores.

DETAILED DESCRIPTION

Figure 1:
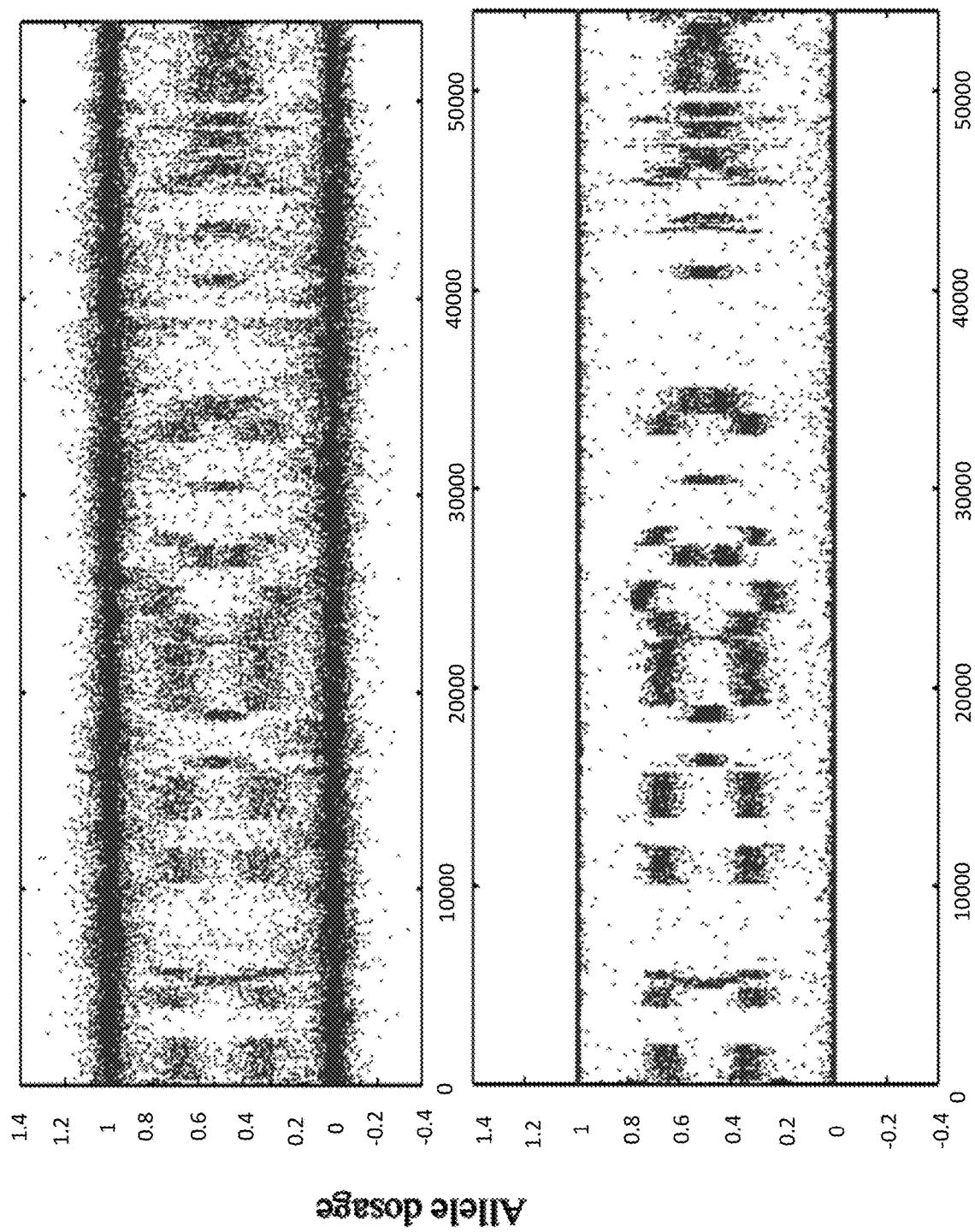
FIG. 1 shows graphs plotting allele dosages of breast cancer cells from a fresh frozen sample from a breast cancer patient along a chromosome as determined using a SNP array (above) and high-throughput sequencing (below).

In general, one aspect of this invention features a method for assessing HRD in a cancer cell or DNA (e.g., genomic DNA) derived therefrom. In some embodiments, the method comprises, or consists essentially of, (a) detecting, in a sample or DNA derived therefrom, CA Regions in at least one pair of human chromosomes or DNA derived therefrom; and (b) determining the number, size (e.g., length), and/or character of said CA Regions.

As used herein, "chromosomal aberration" or "CA" means a somatic change in a cell's chromosomal DNA that falls into at least one of three overlapping categories: LOH, TAI, or LST. Polymorphic loci within the human genome (e.g., single nucleotide polymorphisms (SNPs)) are generally heterozygous within an individual's germline since that individual typically receives one copy from the biological father and one copy from the biological mother. Somatically, however, this heterozygosity can change (via mutation) to homozygosity. This change from heterozygosity to homozygosity is called loss of heterozygosity (LOH). LOH may result from several mechanisms. For example, in some cases, a locus of one chromosome can be deleted in a somatic cell. The locus that remains present on the other chromosome (the other non-sex chromosome for males) is an LOH locus as there is only one copy (instead of two copies) of that locus present within the genome of the affected cells. This type of LOH event results in a copy number reduction. In other cases, a locus of one chromosome (e.g., one non-sex chromosome for males) in a somatic cell can be replaced with a copy of that locus from the other chromosome, thereby eliminating any heterozygosity that may have been present within the replaced locus. In such cases, the locus that remains present on each chromosome is an LOH locus and can be referred to as a copy neutral LOH locus. LOH and its use in determining HRD is described in detail in International Application no. PCT/US2011/040953 (published as WO/2011/160063), the entire contents of which are incorporated herein by reference.

A broader class of chromosomal aberration, which encompasses LOH, is allelic imbalance. Allelic imbalance occurs when the relative copy number (i.e., copy proportion) at a particular locus in somatic cells differs from the germline. For example, if the germline has one copy of allele A and one copy of allele B at a particular locus, and a somatic cell has two copies of A and one copy of B, there is allelic imbalance at the locus because the copy proportion of the somatic cell (2:1) differs from the germline (1:1). LOH is an example of allelic imbalance since the somatic cell has a copy proportion (1:0 or 2:0) that differs from the germline (1:1). But allelic imbalance encompasses more types of chromosomal aberration, e.g., 2:1 germline going to 1:1 somatic; 1:0 germline going to 1:1 somatic; 1:1 germline going to 2:1 somatic, etc. Analysis of regions of allelic imbalance encompassing the telomeres of chromosomes is particularly useful in the invention. Thus, a "telomeric allelic imbalance region" or "TAI Region" is defined as a region with allelic imbalance that (a) extends to one of the subtelomeres and (b) does not cross the centromere. TAI and its use in determining HRD is described in detail in U.S. patent application Ser. No. 13/818,425 (published as US20130281312A1) and Ser. No. 14/466,208 (published as US20150038340A1), the entire contents of each of which are incorporated herein by reference.

A class of chromosomal aberrations that is broader still, which encompasses LOH and TAI, is referred to herein as large scale transition ("LST"). LST refers to any somatic copy number transition (i.e., breakpoint) along the length of a chromosome where it is between two regions of at least some minimum length (e.g., at least 3, 4, 5, 6, 7, 8 9, 10, 11 12, 13, 14, 15, 16, 17, 18, 19 or 20 or more megabases) after filtering out regions shorter than some maximum length (e.g., 0.1, 0.2, 0.3, 0.4, 0.5, 0.6, 0.7, 0.8, 0.9, 1, 1.5, 2, 2.5, 3, 3.5, 4 or more megabases). For example, if after filtering out regions shorter than 3 megabases the somatic cell has a copy number of 1:1 for, e.g., at least 10 megabases and then a breakpoint transition to a region of, e.g., at least 10 megabases with copy number 2:2, this is an LST. An alternative way of defining the same phenomenon is as an LST Region, which is genomic region with stable copy number across at least some minimum length (e.g., at least 3, 4, 5, 6, 7, 8, 9, 10, 11 12, 13, 14, 15, 16, 17, 18, 19 or 20 megabases) bounded by breakpoints (i.e., transitions) where the copy number changes for another region also at least this minimum length. For example, if after filtering out regions shorter than 3 megabases the somatic cell has a region of at least 10 megabases with copy number of 1:1 bounded on one side by a breakpoint transition to a region of, e.g., at least 10 megabases with copy number 2:2, and bounded on the other side by a breakpoint transition to a region of, e.g., at least 10 megabases with copy number 1:2, then this is two LSTs. Notice that this is broader than allelic imbalance because such a copy number change would not be considered allelic imbalance (because the copy proportions 1:1 and 2:2 are the same, i.e., there has been no change in copy proportion). LST and its use in determining HRD is described in detail in U.S. patent application Ser. No. 14/402,254 (published as US20150140122A1), the entire contents of which are incorporated herein by reference.

Different cutoffs for LST score may be used for "near-diploid" and "near-tetraploid" tumors to separate BRCA1/2 intact and deficient samples. LST score sometimes increases with ploidy both within intact and deficient samples. As an alternative to using ploidy-specific cutoffs, some embodiments may employ a modified LST score adjusting it by ploidy: LSTm=LST−kP, where P is ploidy and k is a constant. Based on multivariate logistic regression analysis with deficiency as an outcome and LST and P as predictors, k=15.5 provided the best separation between intact and deficient samples (though one skilled in the art can envisage other values for k).

Chromosomal aberrations can extend across numerous loci to define a region of chromosomal aberration, referred to herein as a "CA Region." Such CA Regions can be any length (e.g., from a length less than about 1.5 Mb up to a length equal to the entire length of the chromosome). An abundance of large CA Regions ("Indicator CA Regions") indicate a deficiency in the homology-dependent repair (HDR) mechanism of a cell. The definition of a region of CA, and thus what constitutes an "Indicator" region, for each type of CA (e.g., LOH, TAI, LST) depends on the particular character of the CA. For example, an "LOH Region" means at least some minimum number of consecutive loci exhibiting LOH or some minimum stretch of genomic DNA having consecutive loci exhibiting LOH. A "TAI Region," on the other hand, means at least some minimum number of consecutive loci exhibiting allelic imbalance extending from the telomere into the rest of the chromosome (or some minimum stretch of genomic DNA extending from the telomere into the rest of the chromosome having consecutive loci exhibiting allelic imbalance). LST is already defined in terms of a region of genomic DNA of at least some minimum size, so "LST" and "LST Region" are used interchangeably in this document to refer to a minimum number of consecutive loci (or some minimum stretch of genomic DNA) having the same copy number bounded by a breakpoint or transition from that copy number to a different one.

In some embodiments a CA Region (whether an LOH Region, TAI region, or LST Region) is an Indicator CA Region (whether an Indicator LOH Region, Indicator TAI region, or Indicator LST Region) if it is at least 3, 4, 5, 6, 7, 8, 9, 10, 11, 12, 13, 14, 15, 16, 17, 18, 19, 20, 25, 30, 35, 40, 45, 50, 60, 70, 80, 90, or 100 megabases or more in length. In some embodiments, Indicator LOH Regions are LOH Regions that are longer than about 1.5, 5, 12, 13, 14, 15, 16, 17 or more (preferably 14, 15, 16 or more, more preferably 15 or more) megabases but shorter than the entire length of the respective chromosome within which the LOH Region is located. Alternatively or additionally, the total combined length of such Indicator LOH Regions may be determined. In some embodiments, Indicator TAI Regions are TAI Regions with allelic imbalance that (a) extend to one of the subtelomeres, (b) do not cross the centromere and (c) are longer than 1.5, 5, 12, 13, 14, 15, 16, 17 or more (preferably 10, 11, 12 or more, more preferably 11 or more) megabases. Alternatively or additionally, the total combined length of such Indicator TAI Regions may be determined. Because the concept of LST already involves regions of some minimum size (such minimum size being determined based on its ability to differentiate HRD from HDR intact samples), Indicator LST Regions as used herein are the same as LST Regions. Furthermore, an LST Region Score can be either derived from the number of regions showing LST as described above or the number of LST breakpoints. In some embodiments the minimum length of the region of stable copy number bounding the LST breakpoint is at least 3, 4, 5, 6, 7, 8, 9, 10, 11 12, 13, 14, 15, 16, 17, 18, 19 or 20 megabases (preferably 8, 9, 10, 11 or more megabases, more preferably 10 megabases) and the maximum region remaining unfiltered is less than 0.1, 0.2, 0.3, 0.4, 0.5, 0.6, 0.7, 0.8, 0.9, 1, 1.5, 2, 2.5, 3, 3.5, 4 or fewer megabases (preferably 2, 2.5, 3, 3.5, or 4 or fewer megabases, more preferably fewer than 3 megabases).

As used herein, a sample has an "HRD signature" if such sample has a number of Indicator CA Regions (as described herein) or a CA Region Score (as described herein) exceeding a reference as described herein, wherein a number or score exceeding such reference indicates homologous recombination deficiency.

Thus the invention generally involves detecting and quantifying Indicator CA Regions in a sample to determine whether cells in the sample (or cells from which DNA in the sample are derived) have an HRD signature. Often this comprises comparing the number of Indicator CA Regions (or a test value or score derived or calculated therefrom and corresponding to such number) to a reference, or index number (or score).

The various aspects of the present invention comprise using a combined analysis of two or more types of CA Regions (including two or more types of Indicator CA Regions) to assess (e.g., detect, diagnose) HRD in a sample. Thus, in one aspect the invention provides a method of assessing (e.g., detecting, diagnosing) HRD in a sample comprising (1) determining the total number (or combined length) of Indicator LOH Regions in the sample; (2) determining the total number (or combined length) of Indicator TAI Regions in the sample; and (3) determining the presence or absence of (e.g., detecting, diagnosing) HRD in the sample based at least in part on the determinations made in (1) and (2). In another aspect the invention provides a method of assessing (e.g., detecting, diagnosing) HRD in a sample comprising (1) determining the total number (or combined length) of Indicator LOH Regions in the sample; (2) determining the total number (or combined length) of Indicator LST Regions in the sample; and (3) determining the presence or absence of (e.g., detecting, diagnosing) HRD in the sample based at least in part on the determinations made in (1) and (2). In another aspect the invention provides a method of assessing (e.g., detecting, diagnosing) HRD in a sample comprising (1) determining the total number (or combined length) of Indicator TAI Regions in the sample; (2) determining the total number (or combined length) of Indicator LST Regions in the sample; and (3) determining the presence or absence of (e.g., detecting, diagnosing) HRD in the sample based at least in part on the determinations made in (1) and (2). In another aspect the invention provides a method of assessing (e.g., detecting, diagnosing) HRD in a sample comprising (1) determining the total number (or combined length) of Indicator LOH Regions in the sample; (2) determining the total number of Indicator TAI Regions in the sample; (3) determining the total number (or combined length) of Indicator LST Regions in the sample; and (4) determining the presence or absence of (e.g., detecting, diagnosing) HRD in the sample based at least in part on the determinations made in (1), (2) and (3).

The various aspects of the present invention comprise using a combined analysis of the averages of three different CA Regions to assess (e.g., detect, diagnose) HRD in a sample. Thus, in one aspect the invention provides a method of assessing (e.g., detecting, diagnosing) HRD in a sample comprising (1) determining the total number of LOH Regions of a certain size or character (e.g., "Indicator LOH Regions", as defined herein) in the sample; (2) determining the total number of TAI Regions of a certain size or character (e.g., "Indicator TAI Regions", as defined herein) in the sample; (3) determining the total number of LST Regions of a certain size or character (e.g., "Indicator LST Regions", as defined herein) in the sample; (4) calculating the average (e.g., arithmetic mean) of the determinations made in (1), (2), and (3); and (5) assessing HRD in the sample based at least in part on the calculated average (e.g., arithmetic mean) made in (4).

As used herein, "CA Region Score" means a test value or score derived or calculated from (e.g., representing or corresponding to) Indicator CA Regions detected in a sample (e.g., a score or test value derived or calculated from the number of Indicator CA Regions detected in a sample). Analogously, as used herein, "LOH Region Score" is a subset of CA Region Scores and means a test value or score derived or calculated from (e.g., representing or corresponding to) Indicator LOH Regions detected in a sample (e.g., a score or test value derived or calculated from the number of Indicator LOH Regions detected in a sample), and so on for TAI Region Score and LST Region Score. Such a score may in some embodiments be simply the number of Indicator CA Regions detected in a sample. In some embodiments the score is more complicated, factoring in the lengths of each Indicator CA Region or a subset of Indicator CA Regions detected.

As discussed above, the invention will generally involve combining the analysis of two or more types of CA Region Scores (which may include the number of such regions). Thus, in one aspect the invention provides a method of assessing (e.g., detecting, diagnosing) HRD in a sample comprising (1) determining an LOH Region Score for the sample; (2) determining a TAI Region Score for the sample; and (3)(a) detecting (or diagnosing) HRD in the sample based at least in part on either the LOH Region Score exceeding a reference or the TAI Region Score exceeding a reference; or optionally (3)(b) detecting (or diagnosing) an absence of HRD in the sample based at least in part on both the LOH Region Score not exceeding a reference and the TAI Region Score not exceeding a reference. In another aspect the invention provides a method of assessing (e.g., detecting, diagnosing) HRD in a sample comprising (1) determining an LOH Region Score for the sample; (2) determining an LST Region Score for the sample; and (3)(a) detecting (or diagnosing) HRD in the sample based at least in part on either the LOH Region exceeding a reference or the LST Region Score exceeding a reference; or optionally (3)(b) detecting (or diagnosing) an absence of HRD in the sample based at least in part on both the LOH Region Score not exceeding a reference and the LST Region Score not exceeding a reference. In another aspect the invention provides a method of assessing (e.g., detecting, diagnosing) HRD in a sample comprising (1) determining a TAI Region Score for the sample; (2) determining an LST Region Score for the sample; and (3)(a) detecting (or diagnosing) HRD in the sample based at least in part on either the TAI Region Score exceeding a reference or the LST Region Score exceeding a reference; or optionally (3)(b) detecting (or diagnosing) an absence of HRD in the sample based at least in part on both the TAI Region Score not exceeding a reference and the LST Region Score not exceeding a reference. In another aspect the invention provides a method of assessing (e.g., detecting, diagnosing) HRD in a sample comprising (1) determining an LOH Region Score for the sample; (2) determining a TAI Region Score for the sample; (3) determining an LST Region Score for the sample; and (4)(a) detecting (or diagnosing) HRD in the sample based at least in part on either the LOH Region Score exceeding reference, the TAI Region Score exceeding a reference or the LST Region Score exceeding a reference; or optionally (4)(b) detecting (or diagnosing) an absence of HRD in the sample based at least in part on the LOH Region Score not exceeding a reference, the TAI Region Score not exceeding a reference and the LST Region Score not exceeding a reference.

In some embodiments the CA Region Score is a combination of scores derived or calculated from (e.g., representing or corresponding to) two or more of (1) the detected LOH Regions ("LOH Region Score", as defined herein), (2) the detected TAI Regions ("TAI Region Score", as defined herein), and/or (3) the detected LST Regions ("LST Region Score", as defined herein). In some embodiments the LOH Region Score and TAI Region Score are combined as follows to yield a CA Region Score:

CA Region Score=$A^*$(LOH Region Score)+$B^*$(TAI Region Score)

In some embodiments the LOH Region Score and TAI Region Score are combined as follows to yield a CA Region Score:

CA Region Score=0.32*(LOH Region Score)+0.68* (TAI Region Score)

OR

CA Region Score=0.34*(LOH Region Score)+0.66* (TAI Region Score)

In some embodiments the LOH Region Score and LST Region Score are combined as follows to yield a CA Region Score:

CA Region Score=$A^*$(LOH Region Score)+$B^*$(LST Region Score)

In some embodiments an LOH Region Score for a sample and an LST Region Score for a sample are combined to yield a CA Region Score as follows:

CA Region Score=0.85*(LOH Region Score)+0.15* (LST Region Score)

In some embodiments the TAI Region Score and LST Region Score are combined as follows to yield a CA Region Score:

CA Region Score=$A^*$(TAI Region Score)+$B^*$(LST Region Score)

In some embodiments the LOH Region Score, TAI Region Score and LST Region Score are combined as follows to yield a CA Region Score:

CA Region Score=$A^*$(LOH Region Score)+$B^*$(TAI Region Score)+$C^*$(LST Region Score)

In some embodiments the LOH Region Score, TAI Region Score and LST Region Score are combined as follows to yield a CA Region Score:

CA Region Score=0.21*(LOH Region Score)+0.67* (TAI Region Score)+0.12*(LST Region Score)

OR

CA Region Score=[0.24]*(LOH Region Score)+ [0.65]*(TAI Region Score)+[0.11]*(LST Region Score)

OR

CA Region Score=[0.11]*(LOH Region Score)+ [0.25]*(TAI Region Score)+[0.12]*(LST Region Score)

In some embodiments the CA Region Score is a combination of scores derived or calculated from (e.g., representing or corresponding to) the average (e.g., arithmetic mean) of (1) the detected LOH Regions ("LOH Region Score", as defined herein), (2) the detected TAI Regions ("TAI Region Score", as defined herein), and/or (3) the detected LST Regions ("LST Region Score", as defined herein) to yield a CA Region Score calculated from one of the following formulae:

$$CA\ \text{Region Score} = \frac{A*(LOH\ \text{Region Score}) + B*(TAI\ \text{Region Score}) + C*(LST\ \text{Region Score})}{3}$$

$$CA\ \text{Region Score} = \frac{A*(LOH\ \text{Region Score}) + B*(TAI\ \text{Region Score})}{2}$$

$$CA\ \text{Region Score} = \frac{A*(LOH\ \text{Region Score}) + C*(LST\ \text{Region Score})}{2}$$

$$CA\ \text{Region Score} = \frac{B*(TAI\ \text{Region Score}) + C*(LST\ \text{Region Score})}{2}$$

In some embodiments, including some specifically illustrated herein, one or more of these coefficients (i.e., A, B, or C, or any combination thereof) is 1 and in some embodiments all three coefficients (i.e., A, B, and C) are 1. Thus, in some embodiments the CA Region Score=(LOH Regions Score)+(TAI Region Score)+(LST Region Score), wherein the LOH Region Score is the number of Indicator LOH Regions (or the total length of LOH), the TAI Region Score is the number of Indicator TAI Regions (or the total length of TAI), and the LST Region Score is the number of Indicator LST Regions (or the total length of LST).

In some cases a formula may not have all of the specified coefficients (and thus not incorporate the corresponding variable(s)). For example, the embodiment mentioned immediately previously may be applied to formula (2) where A in formula (2) is 0.95 and B in formula (2) is 0.61. C and D would not be applicable as these coefficients and their corresponding variables are not found in formula (2) (though the clinical variables are incorporated into the clinical score found in formula (2)). In some embodiments A is between 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8. In some embodiments B is between 0.40 and 1, 0.45 and 0.99, 0.45 and 0.95, 0.55 and 0.8, 0.55 and 0.7, 0.55 and 0.65, 0.59 and 0.63, or between 0.6 and 0.62. In some embodiments C is, where applicable, between 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8. In some embodiments D is, where applicable, between 0.9 and 1, 0.9 and 0.99, 0.9 and 0.95, 0.85 and 0.95, 0.86 and 0.94, 0.87 and 0.93, 0.88 and 0.92, 0.89 and 0.91, 0.85 and 0.9, 0.8 and 0.95, 0.8 and 0.9, 0.8 and 0.85, 0.75 and 0.99, 0.75 and 0.95, 0.75 and 0.9, 0.75 and 0.85, or between 0.75 and 0.8.

In some embodiments A is between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; B is between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; C is, where applicable, between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20; and D is, where applicable, between 0.1 and 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.2 and 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.3 and 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.4 and 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.5 and 0.6, 0.7, 0.8, 0.9, 1, 1.5, 2, 2.5, 3, 3.5, 4, 4.5, 5, 6, 7, 8, 9, 10, 11, 12, 13, 14, 15, or 20; or between 0.6 and 0.7, 0.8, 0.9, 1, 1.5, 2, 2.5, 3, 3.5, 4, 4.5, 5, 6, 7, 8, 9, 10, 11, 12, 13, 14, 15, or 20; or between 0.7 and 0.8, 0.9, 1, 1.5, 2, 2.5, 3, 3.5, 4, 4.5, 5, 6, 7, 8, 9, 10, 11, 12, 13, 14, 15, or 20; or between 0.8 and 0.9, 1, 1.5, 2, 2.5, 3, 3.5, 4, 4.5, 5, 6, 7, 8, 9, 10, 11, 12, 13, 14, 15, or 20; or between 0.9 and 1, 1.5, 2, 2.5, 3, 3.5, 4, 4.5, 5, 6, 7, 8, 9, 10, 11, 12, 13, 14, 15, or 20; or between 1 and 1.5, 2, 2.5, 3, 3.5, 4, 4.5, 5, 6, 7, 8, 9, 10, 11, 12, 13, 14, 15, or 20; or between 1.5 and 2, 2.5, 3, 3.5, 4, 4.5, 5, 6, 7, 8, 9, 10, 11, 12, 13, 14, 15, or 20; or between 2 and 2.5, 3, 3.5, 4, 4.5, 5, 6, 7, 8, 9, 10, 11, 12, 13, 14, 15, or 20; or between 2.5 and 3, 3.5, 4, 4.5, 5, 6, 7, 8, 9, 10, 11, 12, 13, 14, 15, or 20; or between 3 and 3.5, 4, 4.5, 5, 6, 7, 8, 9, 10, 11, 12, 13, 14, 15, or 20; or between 3.5 and 4, 4.5, 5, 6, 7, 8, 9, 10, 11, 12, 13, 14, 15, or 20; or between 4 and 4.5, 5, 6, 7, 8, 9, 10, 11, 12, 13, 14, 15, or 20; or between 4.5 and 5, 6, 7, 8, 9, 10, 11, 12, 13, 14, 15, or 20; or between 5 and 6, 7, 8, 9, 10, 11, 12, 13, 14, 15, or 20; or between 6 and 7, 8, 9, 10, 11, 12, 13, 14, 15, or 20; or between 7 and 8, 9, 10, 11, 12, 13, 14, 15, or 20; or between 8 and 9, 10, 11, 12, 13, 14, 15, or 20; or between 9 and 10, 11, 12, 13, 14, 15, or 20; or between 10 and 11, 12, 13, 14, 15, or 20; or between 11 and 12, 13, 14, 15, or 20; or between 12 and 13, 14, 15, or 20; or between 13 and 14, 15, or 20; or between 14 and 15, or 20; or between 15 and 20. In some embodiments, A, B, and/or C is within rounding of any of these values (e.g., A is between 0.45 and 0.54, etc.).

Thus, in one aspect the invention provides a method of assessing (e.g., detecting, diagnosing) HRD in a sample comprising (1) determining an LOH Region Score for the sample; (2) determining a TAI Region Score for the sample; and (3)(a) detecting (or diagnosing) HRD in the sample based at least in part on a combination of the LOH Region Score and the TAI Region Score (e.g., a Combined CA Region Score) exceeding a reference; or optionally (3)(b) detecting (or diagnosing) an absence of HRD in the sample based at least in part on a combination of the LOH Region Score and the TAI Region Score (e.g., a Combined CA Region Score) not exceeding a reference. In another aspect the invention provides a method of assessing (e.g., detecting, diagnosing) HRD in a sample comprising (1) determining an LOH Region Score for the sample; (2) determining an LST Region Score for the sample; and (3)(a) detecting (or diagnosing) HRD in the sample based at least in part on a combination of the LOH Region Score and the LST Region Score (e.g., a Combined CA Region Score) exceeding a reference; or optionally (3)(b) detecting (or diagnosing) an absence of HRD in the sample based at least in part on a combination of the LOH Region Score and the LST Region Score (e.g., a Combined CA Region Score) not exceeding a reference. In another aspect the invention provides a method of assessing (e.g., detecting, diagnosing) HRD in a sample comprising (1) determining a TAI Region Score for the sample; (2) determining an LST Region Score for the sample; and (3)(a) detecting (or diagnosing) HRD in the sample based at least in part on a combination of the TAI Region Score and the LST Region Score (e.g., a Combined CA Region Score) exceeding a reference; or optionally (3)(b) detecting (or diagnosing) an absence of HRD in the sample based at least in part on a combination of the TAI Region Score and the LST Region Score (e.g., a Combined CA Region Score) not exceeding a reference. In another aspect the invention provides a method of assessing (e.g., detecting, diagnosing) HRD in a sample comprising (1) determining an LOH Region Score for the sample; (2) determining a TAI Region Score for the sample; (3) determining an LST Region Score for the sample; and (4)(a) detecting (or diagnosing) HRD in the sample based at least in part on a combination of the LOH Region Score, the TAI Region Score and the LST Region Score (e.g., a Combined CA Region Score) exceeding a reference; or optionally (4)(b) detecting (or diagnosing) an absence of HRD in the sample based at least in part on the LOH Region Score, the TAI Region Score and the LST Region Score (e.g., a Combined CA Region Score) not exceeding a reference.

Thus another aspect of the invention provides a method of assessing (e.g., detecting, diagnosing) HRD in a sample comprising (1) determining the total number of LOH Regions of a certain size or character (e.g., "Indicator LOH Regions", as defined herein) in the sample; (2) determining the total number of TAI Regions of a certain size or character (e.g., "Indicator TAI Regions", as defined herein) in the sample; (3) determining the total number of LST Regions of a certain size or character (e.g., "Indicator LST Regions", as defined herein) in the sample; (4) calculating the average (e.g., arithmetic mean) of the determinations made in (1), (2), and (3); and (5) assessing HRD in the sample based at least in part on the calculated average (e.g., arithmetic mean) made in (4).

In some embodiments, the reference (or index) discussed above for the CA Region Score (e.g., the number of Indicator CA Regions) may be 5, 6, 7, 8, 9, 10, 11, 12, 13, 14, 15, 16, 18, 19, 20 or greater, preferably 5, preferably 8, more preferably 9 or 10, most preferably 10. The reference for the total (e.g., combined) length of Indicator CA Regions may be about 75, 90, 105, 120, 130, 135, 150, 175, 200, 225, 250, 275, 300, 325 350, 375, 400, 425, 450, 475, 500 megabases or greater, preferably about 75 megabases or greater, preferably about 90 or 105 megabases or greater, more preferably about 120 or 130 megabases or greater, and more preferably about 135 megabases or greater, and most preferably about 150 megabases or greater. In some embodiments, the reference discussed above for the Combined CA Region Score (e.g., the combined number of Indicator LOH Regions, Indicator, TAI Regions and/or Indicator LST Regions) may be 5, 6, 7, 8, 9, 10, 11, 12, 13, 14, 15, 16, 18, 19, 20, 22, 24, 26, 28, 30, 32, 34, 36, 38, 40, 42, 44, 46, 48, 50 or greater, preferably 5, preferably 10, preferably 15, preferably 20, preferably 25, preferably 30, preferably 35, preferably 40-44, most preferably 42. The reference for the total (e.g., combined) length of Indicator LOH Regions, Indicator TAI Regions and/or Indicator LST Regions may be about 75, 90, 105, 120, 130, 135, 150, 175, 200, 225, 250, 275, 300, 325 350, 375, 400, 425, 450, 475, 500 megabases or greater, preferably about 75 megabases or greater, preferably about 90 or 105 megabases or greater, more preferably about 120 or 130 megabases or greater, and more preferably about 135 megabases or greater, and most preferably about 150 megabases or greater.

In some embodiments, the invention provides a method for detecting an HRD signature in a sample. Thus, another aspect of the invention provides a method for detecting an HRD signature in a sample comprising (1) determining the total number of LOH Regions of a certain size or character (e.g., "Indicator LOH Regions", as defined herein) in the sample; (2) determining the total number of TAI Regions of a certain size or character (e.g., "Indicator TAI Regions", as defined herein) in the sample; (3) determining the total number of LST Regions of a certain size or character (e.g., "Indicator LST Regions", as defined herein) in the sample; (4) combining the determinations made in (1), (2), and (3) (e.g., calculating or deriving a Combined CA Region Score); and (5) characterizing a sample in which the Combined CA Region Score is greater than a reference value as having an HRD signature. In some embodiments, the reference value is 42. Thus, in some embodiments a sample is characterized as having an HRD signature when the reference value is 42. In some embodiments, the reference discussed above for the Combined CA Region Score (e.g., the combined number of Indicator LOH Regions, Indicator, TAI Regions and/or Indicator LST Regions) may be 5, 6, 7, 8, 9, 10, 11, 12, 13, 14, 15, 16, 18, 19, 20, 22, 24, 26, 28, 30, 32, 34, 36, 38, 40, 42, 44, 46, 48, 50 or greater, preferably 5, preferably 10, preferably 15, preferably 20, preferably 25, preferably 30, preferably 35, preferably 40-44, most preferably 42.

In some embodiments, the number of Indicator CA Regions (or the combined length, a CA Region Score or a Combined CA Region Score) in a sample is considered "greater" than a reference if it is at least 2-, 3-, 4-, 5-, 6-, 7-, 8-, 9-, or 10-fold greater than the reference while in some embodiments, it is considered "greater" if it is at least 1, 2, 3, 4, 5, 6, 7, 8, 9, or 10 standard deviations greater than the reference. Conversely, in some embodiments the number of Indicator CA Regions (or the combined length, a CA Region Score or a Combined CA Region Score) in a sample is considered "not greater" than a reference if it is not more than 2-, 3-, 4-, 5-, 6-, 7-, 8-, 9-, or 10-fold greater than the reference while in some embodiments, it is considered "not greater" if it is not more than 1, 2, 3, 4, 5, 6, 7, 8, 9, or 10 standard deviations greater than the reference.

In some embodiments the reference number (or length, value or score) is derived from a relevant reference population. Such reference populations may include patients (a) with the same cancer as the patient being tested, (b) with the same cancer sub-type, (c) with cancer having similar genetic or other clinical or molecular features, (d) who responded to a particular treatment, (e) who did not respond to a particular treatment, (f) who are apparently healthy (e.g., do not have any cancer or at least do not have the tested patient's cancer), etc. The reference number (or length, value or score) may be (a) representative of the number (or length, value or score) found in the reference population as a whole, (b) an average (mean, median, etc.) of the number (or length, value or score) found in the reference population as a whole or a particular sub-population, (c) representative of the number (or length, value or score) (e.g., an average such as mean or median) found in terciles, quartiles, quintiles, etc. of the reference population as ranked by (i) their respective number (or length, value or score) or (ii) the clinical feature they were found to have (e.g., strength of response, prognosis (including time to cancer-specific death), etc.), or (d) selected to have a high sensitivity for detecting HRD for predicting response to a particular therapy (e.g., platinum, PARP inhibitor, etc.).

In some embodiments the reference or index that, if exceeded by the test value or score from the sample, indicates HRD is the same as the reference that, if not exceeded by the test value or score from the sample, indicates the absence of HRD (or functional HDR). In some embodiments they are different.

In another aspect, the present invention provides a method of predicting the status of BRCA1 and BRCA2 genes in a sample. Such method is analogous to the methods described above and differs in that the determination of CA Regions, LOH Regions, TAI Regions, LST Regions, or scores incorporating these are used to assess (e.g., detect) BRCA1 and/or BRCA2 deficiency in the sample.

In another aspect, this invention provides a method of predicting a cancer patient's response to a cancer treatment regimen comprising a DNA damaging agent, an anthracycline, a topoisomerase I inhibitor, radiation, and/or a PARP inhibitor. Such method is analogous to the methods described above and differs in that the determination of CA Regions, LOH Regions, TAI Regions, LST Regions, or scores incorporating these, including high HRD scores (e.g., an HRD signature or a high combined CA Region Score), are used to predict the likelihood that the cancer patient will respond to the cancer treatment regimen.

In some embodiments, the patients are treatment naïve patients. In another aspect, this invention provides a method of treating cancer. Such method is analogous to the methods described above and differs in that a particular treatment regimen is administered (recommended, prescribed, etc.) based at least in part on the determination of CA Regions, LOH Regions, TAI Regions, LST Regions, or scores incorporating these.

In another aspect, this invention features the use of one or more drugs selected from the group consisting of DNA damaging agents, anthracyclines, topoisomerase I inhibitors, and PARP inhibitors, in the manufacture of a medicament useful for treating a cancer in a patient identified as having (or as having had) a cancer cell determined to have high levels of HRD (e.g., an HRD signature) as described herein.

In another aspect, this document features a method for assessing a sample for the presence of a mutation within a gene from an HDR pathway. Such method is analogous to the methods described above and differs in that the determination of CA Regions, LOH Regions, TAI Regions, LST Regions, or scores incorporating these are used to detect (or not) the presence of a mutation within a gene from an HDR pathway.

In another aspect, this document features a method for assessing cancer cells of a patient for the presence of an HRD signature. The method comprises, or consists essentially of, (a) detecting the presence of more than a reference number of Indicator CA Regions in at least one pair of human chromosomes of a cancer cell of the cancer patient, and (b) identifying the patient as having cancer cells with the HRD signature. In another aspect, this document features a method for assessing cancer cells of a patient for the presence of an HDR deficient status. The method comprises, or consists essentially of, (a) detecting the presence of more than a reference number of Indicator CA Regions in at least one pair of human chromosomes of a cancer cell of the cancer patient, and (b) identifying the patient as having cancer cells with the HDR deficient status. In another aspect, this document features a method for assessing cancer cells of a patient for having an HRD signature. The method comprises, or consists essentially of, (a) detecting the presence of more than a reference number of Indicator CA Regions in at least one pair of human chromosomes of a cancer cell of the cancer patient, and (b) identifying the patient as having cancer cells with an HRD signature. In another aspect, this document features a method for assessing cancer cells of a patient for the presence of a genetic mutation within a gene from an HDR pathway. The method comprises, or consists essentially of, (a) detecting the presence of more than a reference number of Indicator CA Regions in at least one pair of human chromosomes of a cancer cell of the cancer patient, and (b) identifying the patient as having cancer cells with the genetic mutation.

In another aspect, this document features a method for determining if a patient is likely to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) detecting the presence of more than a reference number of Indicator CA Regions in at least one pair of human chromosomes of a cancer cell of the cancer patient, and (b) identifying the patient as being likely to respond to the cancer treatment regimen. In another aspect, this document features a method for assessing a patient. The method comprises, or consists essentially of, (a) determining that the patient comprises cancer cells having an HRD signature, wherein the presence of more than a reference number of Indicator CA Regions in at least one pair of human chromosomes of a cancer cell of the cancer patient indicates that the cancer cells have the HRD signature, and (b) diagnosing the patient as having cancer cells with the HRD signature. In another aspect, this document features a method for assessing a patient. The method comprises, or consists essentially of, (a) determining that the patient comprises cancer cells having an HDR deficiency status, wherein the presence of more than a reference number of Indicator CA Regions in at least one pair of human chromosomes of a cancer cell of the cancer patient indicates that the cancer cells have the HDR deficiency status, and (b) diagnosing the patient as having cancer cells with the HDR deficient status. In another aspect, this document features a method for assessing a patient. The method comprises, or consists essentially of, (a) determining that the patient comprises cancer cells having an HDR deficient status, wherein the presence of more than a reference number of Indicator CA Regions in at least one pair of human chromosomes of a cancer cell of the cancer patient indicates that the cancer cells have high HDR, and (b) diagnosing the patient as having cancer cells with an HDR deficient status. In another aspect, this document features a method for assessing a patient. The method comprises, or consists essentially of, (a) determining that the patient comprises cancer cells having a genetic mutation within a gene from an HDR pathway, wherein the presence of more than a reference number of Indicator CA Regions in at least one pair of human chromosomes of a cancer cell of the cancer patient indicates that the cancer cells have the genetic mutation, and (b) diagnosing the patient as having cancer cells with the genetic mutation. In another aspect, this document features a method for assessing a patient for a likelihood to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises cancer cells having an HRD signature, wherein the presence of more than a reference number of Indicator CA Regions in at least one pair of human chromosomes of a cancer cell of the cancer patient indicates that the cancer cells have the HRD signature, and (b) diagnosing, based at least in part on the presence of the HRD signature, the patient as being likely to respond to the cancer treatment regimen. In another aspect, this document features a method for assessing a patient for a likelihood to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises cancer cells having an HRD signature, wherein the presence of more than a reference number of Indicator CA Regions in at least one pair of human chromosomes of a cancer cell of the cancer patient indicates that the cancer cells have an HRD signature, and (b) diagnosing, based at least in part on the presence of the HRD signature, the patient as being likely to respond to the cancer treatment regimen.

In another aspect, this document features a method for performing a diagnostic analysis of a cancer cell of a patient. The method comprises, or consists essentially of, (a) detecting the presence of more than a reference number of Indicator CA Regions in at least one pair of human chromosomes of the cancer cell, and (b) identifying or classifying the patient as having cancer cells with an HRD signature.

In another aspect, this document features a method for performing a diagnostic analysis of a cancer cell of a patient. The method comprises, or consists essentially of, (a) detecting the presence of more than a reference number of Indicator CA Regions in at least one pair of human chromosomes of the cancer cell, and (b) identifying or classifying the patient as having cancer cells with a HDR deficient status. In another aspect, this document features a method for performing a diagnostic analysis of a cancer cell of a patient. The method comprises, or consists essentially of, (a) detecting the presence of more than a reference number of Indicator CA Regions in at least one pair of human chromosomes of the cancer cell, and (b) identifying or classifying the patient as having cancer cells with an HDR deficient status. In another aspect, this document features a method for performing a diagnostic analysis of a cancer cell of a patient. The method comprises, or consists essentially of, (a) detecting the presence of more than a reference number of Indicator CA Regions in at least one pair of human chromosomes of the cancer cell that are longer, and (b) identifying or classifying the patient as having cancer cells with a genetic mutation within a gene from an HDR pathway. In another aspect, this document features a method for performing a diagnostic analysis of a cancer cell of a patient to determine if the cancer patient is likely to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) detecting the presence of more than a reference number of Indicator CA Regions in at least one pair of human chromosomes of the cancer cell, and (b) identifying or classifying the patient as being likely to respond to the cancer treatment regimen.

In another aspect, this document features a method for diagnosing a patient as having cancer cells having an HRD signature. The method comprises, or consists essentially of, (a) determining that the patient comprises cancer cells having the HRD signature, wherein the presence of more than a reference number of Indicator CA Regions in at least one pair of human chromosomes of a cancer cell of the cancer patient indicates that the cancer cells have the HRD signature, and (b) diagnosing the patient as having cancer cells with the HRD signature. In another aspect, this document features a method for diagnosing a patient as having cancer cells with an HDR deficient status. The method comprises, or consists essentially of, (a) determining that the patient comprises cancer cells having the HDR deficiency status, wherein the presence of more than a reference number of Indicator CA Regions in at least one pair of human chromosomes of a cancer cell of the cancer patient indicates that the cancer cells have the HDR deficiency status, and (b) diagnosing the patient as having cancer cells with the HDR deficient status. In another aspect, this document features a method for diagnosing a patient as having cancer cells with an HDR deficient status. The method comprises, or consists essentially of, (a) determining that the patient comprises cancer cells having the HDR deficient status, wherein the presence of more than a reference number of Indicator CA Regions in at least one pair of human chromosomes of a cancer cell of the cancer patient indicates that the cancer cells have the HDR deficient status, and (b) diagnosing the patient as having cancer cells with the HDR deficient status. In another aspect, this document features a method for diagnosing a patient as having cancer cells with a genetic mutation within a gene from an HDR pathway. The method comprises, or consists essentially of, (a) determining that the patient comprises cancer cells having the genetic mutation, wherein the presence of more than a reference number of Indicator CA Regions in at least one pair of human chromosomes of a cancer cell of the cancer patient indicates that the cancer cells have the genetic mutation, and (b) diagnosing the patient as having cancer cells with the genetic mutation. In another aspect, this document features a method for diagnosing a patient as being a candidate for a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises cancer cells having an HRD signature, wherein the presence of more than a reference number of Indicator CA Regions in at least one pair of human chromosomes of a cancer cell of the cancer patient indicates that the cancer cells have the HRD signature, and (b) diagnosing, based at least in part on the presence of the HRD signature, the patient as being likely to respond to the cancer treatment regimen. In another aspect, this document features a method for diagnosing a patient as being a candidate for a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises cancer cells having high an HRD signature, wherein the presence of more than a reference number of Indicator CA Regions in at least one pair of human chromosomes of a cancer cell of the cancer patient indicates that the cancer cells have an HRD signature, and (b) diagnosing, based at least in part on the presence of the HRD signature, the patient as being likely to respond to the cancer treatment regimen.

In another aspect, the invention provides a method for assessing a patient. The method comprises, or consists essentially of, (a) determining whether the patient has (or had) cancer cells with more than a reference number of Indicator CA Regions (or, e.g., a CA Region Score exceeding a reference CA Region Score); and (b)(1) diagnosing the patient as having cancer cells with HRD if it is determined that the patient has (or had) cancer cells with more than a reference number of CA Regions (or, e.g., a CA Region Score exceeding a reference CA Region Score); or (b)(2) diagnosing the patient as not having cancer cells with HRD if it is determined that the patient does not have (or has not had) cancer cells with more than a reference number of CA Regions (or, e.g., the patient does not have (or has not had) cancer cells with a CA Region Score exceeding a reference CA Region Score).

In another aspect, this invention features the use of a plurality of oligonucleotides capable of hybridizing to a plurality of polymorphic regions of human genomic DNA, in the manufacture of a diagnostic kit useful for determining the total number or combined length of CA Regions in at least a chromosome pair (or DNA derived therefrom) in a sample obtained from a cancer patient, and for detecting (a) HRD, high HRD, or likelihood of HRD (each, e.g., an HRD signature) in the sample, (b) deficiency (or likelihood of deficiency) in a BRCA1 or BRCA2 gene in the sample, or (c) an increased likelihood that the cancer patient will respond to a cancer treatment regimen comprising a DNA damaging agent, an anthracycline, a topoisomerase I inhibitor, radiation, or a PARP inhibitor.

In another aspect, this invention features a system for detecting HRD (e.g., an HRD signature) in a sample. The system comprises, or consists essentially of, (a) a sample analyzer configured to produce a plurality of signals about genomic DNA of at least one pair of human chromosomes (or DNA derived therefrom) in the sample, and (b) a computer sub-system programmed to calculate, based on the plurality of signals, the number or combined length of CA Regions in the at least one pair of human chromosomes. The computer sub-system can be programmed to compare the number or combined length of CA Regions to a reference number to detect (a) HRD, high HRD, or likelihood of HRD (each, e.g., an HRD signature) in the sample, (b) deficiency (or likelihood of deficiency) in a BRCA1 or BRCA2 gene in the sample, or (c) an increased likelihood that the cancer patient will respond to a cancer treatment regimen comprising a DNA damaging agent, an anthracycline, a topoisomerase I inhibitor, radiation, or a PARP inhibitor. The system can comprise an output module configured to display (a), (b), or (c). The system can comprise an output module configured to display a recommendation for the use of the cancer treatment regimen.

In another aspect, the invention provides a computer program product embodied in a computer readable medium that, when executing on a computer, provides instructions for detecting the presence or absence of any CA Region along one or more human chromosomes other than the human X and Y sex chromosomes (the CA Regions optionally being Indicator CA Regions); and determining the total number or combined length of the CA Regions in the one or more chromosome pairs. The computer program product can include other instructions.

In another aspect, the present invention provides a diagnostic kit. The kit comprises, or consists essentially of, at least 500 oligonucleotides capable of hybridizing to a plurality of polymorphic regions of human genomic DNA (or DNA derived therefrom); and a computer program product provided herein. The computer program product can be embodied in a computer readable medium that, when executing on a computer, provides instructions for detecting the presence or absence of any CA Region along one or more of human chromosomes other than the human X and Y sex chromosomes (the CA Regions optionally being Indicator CA Regions); and determining the total number or combined length of the CA Regions in the one or more chromosome pairs. The computer program product can include other instructions.

In some embodiments of any one or more of the aspects of the invention described in the preceding paragraphs, any one or more of the following can be applied as appropriate. The CA Regions can be determined in at least two, five, ten, or 21 pairs of human chromosomes. The cancer cell can be an ovarian, breast, lung or esophageal cancer cell. The reference can be 6, 7, 8, 9, 10, 11, 12, 13, 14, 15, 16, 17, 18 or 20 or greater. The at least one pair of human chromosomes can exclude human chromosome 17. The DNA damaging agent can be cisplatin, carboplatin, oxalaplatin, or picoplatin, the anthracycline can be epirubincin or doxorubicin, the topoisomerase I inhibitor can be campothecin, topotecan, or irinotecan, or the PARP inhibitor can be iniparib, olaparib or velapirib. The patient can be a treatment naïve patient.

As described herein, a sample (e.g., cancer cell sample or a sample containing DNA derived from one or more cancer cells) can be identified as having an "HRD signature" (or alternatively called "HDR-deficiency signature") if the genome of the cells being assessed contains (a) any of an LOH Region Score, a TAI Region Score or an LST Region Score exceeding a reference or (b) a Combined CA Region Score exceeding a reference. Conversely, a sample (e.g., cancer cell sample or a sample containing DNA derived from one or more cancer cells) can be identified as lacking an "HRD signature" (or alternatively called "HDR-deficiency signature") if the genome of the cells being assessed contains (a) an LOH Region Score, a TAI Region Score and an LST Region Score each not exceeding a reference or (b) a Combined CA Region Score not exceeding a reference.

Cells (e.g., cancer cells) identified as having an HRD signature can be classified as having an increased likelihood of having an HDR deficiency and/or as having an increased likelihood of having a deficient status in one or more genes in the HDR pathway. For example, cancer cells identified as having an HRD signature can be classified as having an increased likelihood of having an HDR deficient status. In some cases, cancer cells identified as having an HRD signature can be classified as having an increased likelihood of having a deficient status for one or more genes in the HDR pathway. As used herein, deficient status for a gene means the sequence, structure, expression and/or activity of the gene or its product is/are deficient as compared to normal. Examples include, but are not limited to, low or no mRNA or protein expression, deleterious mutations, hypermethylation, attenuated activity (e.g., enzymatic activity, ability to bind to another biomolecule), etc. As used herein, deficient status for a pathway (e.g., HDR pathway) means at least one gene in that pathway (e.g., BRCA1) is deficient. Examples of highly deleterious mutations include frameshift mutations, stop codon mutations, and mutations that lead to altered RNA splicing. Deficient status in a gene in the HDR pathway may result in deficiency or reduced activity in homology directed repair in the cancer cells. Examples of genes in the HDR pathway include, without limitation, the genes listed in Table 1.

TABLE 1

Selected HDR Pathway Genes

| Gene Name | Entrez Gene Symbol (if assigned) | Entrez Gene Id |
|---|---|---|
| BLM | BLM | 641 |
| BRCA1 | BRCA1 | 672 |
| BRCA2 | BRCA2 | 675 |
| CtIP | RBBP8 | 5932 |
| DNA polymerase delta | POLD1 | 5424 |
| | POLD2 | 5424 |
| | POLD3 | 10714 |
| | POLD4 | 57804 |
| DNA polymerase eta | POLH | 5429 |
| DNA2 | DNA2 | 1763 |
| EME1 | EME1 | 146956 |
| ERCC1 | ERCC1 | 2067 |
| EXO1 | EXO1 | 9156 |
| FANCM | FANCM | 57697 |
| GEN1 | GEN1 | 348654 |
| MRE11 | MRE11A | 4361 |
| MUS81 | MUS81 | 80198 |
| NBS1 | NBN | 4683 |
| PALB2 | PALB2 | 79728 |
| PCNA | PCNA | 5111 |
| RAD50 | RAD50 | 10111 |
| RAD51 | RAD51 | 5888 |
| RAD51AP1 | RAD51AP1 | 10635 |
| RAD51B | RAD51L1 | 5890 |
| RAD51C | RAD51L2 | 5889 |
| RAD51D | RAD51L3 | 5892 |
| RAD54 | ATRX | 546 |
| RAD54B | RAD54B | 25788 |
| RMI1 | RMI1 | 80010 |

TABLE 1-continued

Selected HDR Pathway Genes

| Gene Name | Entrez Gene Symbol (if assigned) | Entrez Gene Id |
|---|---|---|
| RMI2 | C16orf75 | 116028 |
| RPA | RPA1 | 6117 |
| RTEL1 | RTEL1 | 51750 |
| SLX1 | | |
| SLX2 | | |
| SLX4 | SLX4 | 84464 |
| TOP2A | TOP2A | 7153 |
| XPF | ERCC4 | 2072 |
| XRCC2 | XRCC2 | 7516 |
| XRCC3 | XRCC3 | 7517 |

Figure 2:
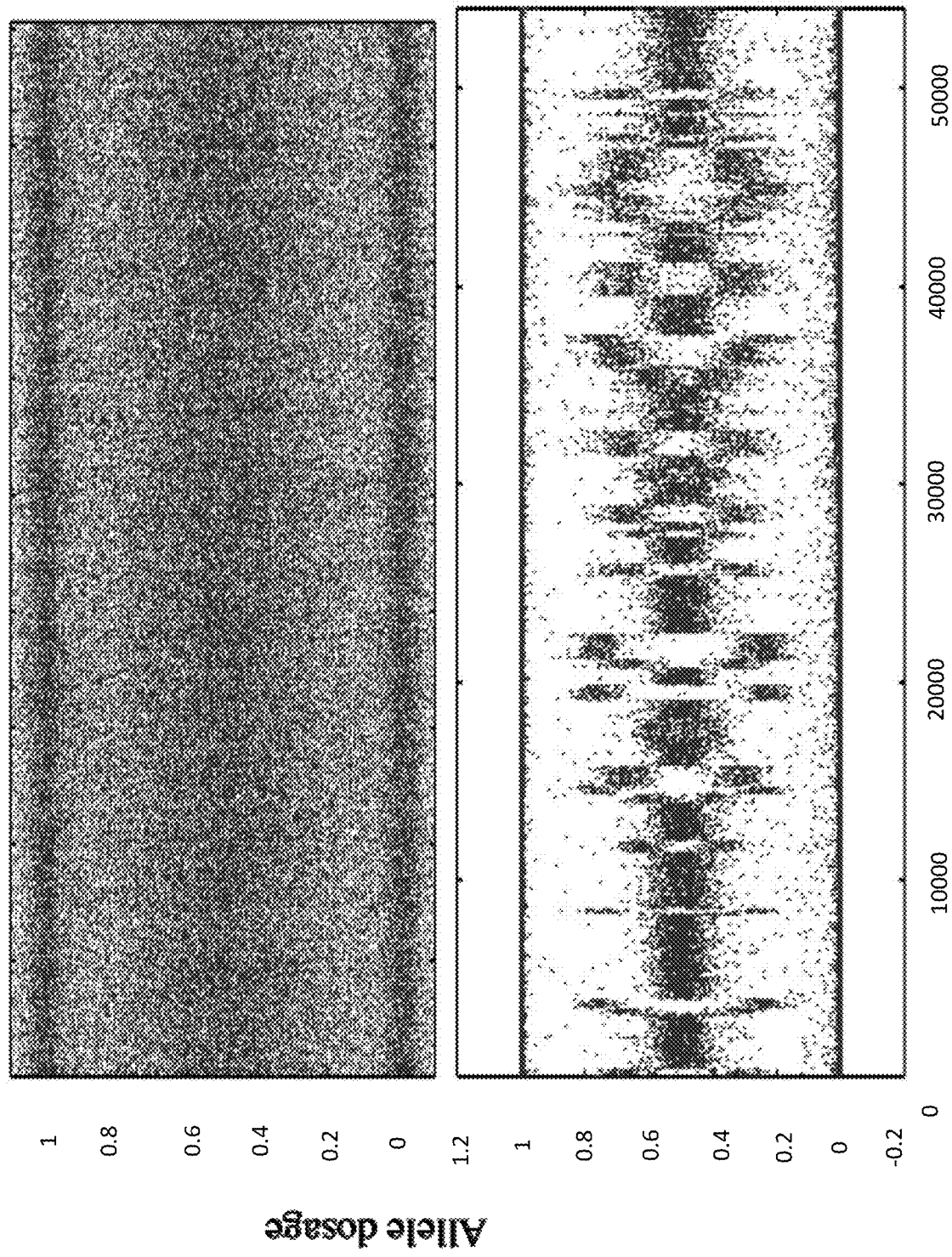
FIG. 2 shows graphs plotting allele dosages of breast cancer cells from an FFPE sample from a breast cancer patient along a chromosome as determined using a SNP array (above) and high-throughput sequencing (below).

As described herein, identifying CA loci (as well as the size and number of CA Regions) can include, first, determining the genotype of a sample at various genomic loci (e.g., SNP loci, individual bases in large-scale sequencing) and, second, determining whether the loci exhibit any of LOH, TAI or LST. Any appropriate technique can be used to determine genotypes at loci of interest within the genome of a cell. For example, single nucleotide polymorphism (SNP) arrays (e.g., human genome-wide SNP arrays), targeted sequencing of loci of interest (e.g., sequencing SNP loci and their surrounding sequences), and even large-scale sequencing (e.g., whole exome, transcriptome, or genome sequencing) can be used to identify loci as being homozygous or heterozygous. Typically, an analysis of the homozygous or heterozygous nature of loci over a length of a chromosome can be performed to determine the length of CA Regions. For example, a stretch of SNP locations that are spaced apart (e.g., spaced about 25 kb to about 100 kb apart) along a chromosome can be evaluated using SNP array results to determine not only the presence of a region of homozygosity (e.g., LOH) along a chromosome but also the length of that region. Results from a SNP array can be used to generate a graph that plots allele dosages along a chromosome. Allele dosage $d_i$ for SNP i can be calculated from adjusted signal intensities of two alleles ($A_i$ and $B_i$): $d_i = A_i/(A_i+B_i)$. An example of such a graph is presented in FIGS. 1 and 2, which show the difference between fresh frozen and FFPE samples and between SNP microarray and SNP sequencing analyses. Numerous variations on nucleic acid arrays useful in the invention are known in the art. These include the arrays used in the various examples below (e.g., Affymetrix 500K GeneChip array in Example 3; Affymetrix OncoScan™ FFPE Express 2.0 Services (Formerly MIP CN Services) in Example 4).

Once a sample's genotype has been determined for a plurality of loci (e.g., SNPs), common techniques can be used to identify loci and regions of LOH, TAI and LST (including those described in International Application no. PCT/US2011/040953 (published as WO/2011/160063); International Application no. PCT/US2011/048427 (published as WO/2012/027224); Popova et al., *Ploidy and large-scale genomic instability consistently identify basal-like breast carcinomas with BRCA1/2 inactivation*, CANCER RES. (2012) 72:5454-5462). In some embodiments determining whether chromosomal imbalance or large scale transitions includes determining whether these are somatic or germline aberrations. One way to determine to do this is to compare the somatic genotype to the germline. For example, the genotype for a plurality of loci (e.g., SNPs) can be determined in both a germline (e.g., blood) sample and a somatic (e.g., tumor) sample. The genotypes for each sample can be compared (typically computationally) to determine where the genome of the germline cell was heterozygous and the genome of the somatic cell is homozygous. Such loci are LOH loci and regions of such loci are LOH Regions.

Computational techniques can also be used to determine whether an aberration is germline or somatic. Such techniques are particularly useful when a germline sample is not available for analysis and comparison. For example, algorithms such as those described elsewhere can be used to detect LOH regions using information from SNP arrays (Nannya et al., Cancer Res. (2005) 65:6071-6079 (2005)). Typically these algorithms do not explicitly take into account contamination of tumor samples with benign tissue. Cf. International Application No. PCT/US2011/026098 to Abkevich et al.; Goransson et al., PLoS One (2009) 4(6): e6057. This contamination is often high enough to make the detection of LOH regions challenging. Improved analytical methods according to the present invention for identifying LOH, TAI and LST, even in spite of contamination, include those embodied in computer software products as described below.

The following is one example. If the observed ratio of the signals of two alleles, A and B, is two to one, there are two possibilities. The first possibility is that cancer cells have LOH with deletion of allele B in a sample with 50% contamination with normal cells. The second possibility is that there is no LOH but allele A is duplicated in a sample with no contamination with normal cells. An algorithm can be implemented as a computer program as described herein to reconstruct LOH regions based on genotype (e.g., SNP genotype) data. One point of the algorithm is to first reconstruct allele specific copy numbers (ASCN) at each locus (e.g., SNP). ASCNs are the numbers of copies of both paternal and maternal alleles. An LOH region is then determined as a stretch of SNPs with one of the ASCNs (paternal or maternal) being zero. The algorithm can be based on maximizing a likelihood function and can be conceptually akin to a previously described algorithm designed to reconstruct total copy number (rather than ASCN) at each locus (e.g., SNP). See International Application No. PCT/US2011/026098 to Abkevich et al. The likelihood function can be maximized over ASCN of all loci, level of contamination with benign tissue, total copy number averaged over the whole genome, and sample specific noise level. The input data for the algorithm can include or consist of (1) sample-specific normalized signal intensities for both allele of each locus and (2) assay-specific (specific for different SNP arrays and for sequence based approach) set of parameters defined based on analysis of large number of samples with known ASCN profiles.

In some cases, nucleic acid sequencing techniques can be used to genotype loci. For example, genomic DNA from a cell sample (e.g., a cancer cell sample) can be extracted and fragmented. Any appropriate method can be used to extract and fragment genomic nucleic acid including, without limitation, commercial kits such as QIAamp™ DNA Mini Kit (Qiagen™), MagNA™ Pure DNA Isolation Kit (Roche Applied Science™) and GenElute™ Mammalian Genomic DNA Miniprep Kit (Sigma-Aldrich™). Once extracted and fragmented, either targeted or untargeted sequencing can be done to determine the sample's genotypes at loci. For example, whole genome, whole transcriptome, or whole exome sequencing can be done to determine genotypes at millions or even billions of base pairs (i.e., base pairs can be "loci" to be evaluated).

In some cases, targeted sequencing of known polymorphic loci (e.g., SNPs and surrounding sequences) can be done as an alternative to microarray analysis. For example, the genomic DNA can be enriched for those fragments containing a locus (e.g., SNP location) to be analyzed using kits designed for this purpose (e.g., Agilent SureSelect™, Illumina TruSeq Capture™, and Nimblegen SeqCap EZ Choice™). For example, genomic DNA containing the loci to be analyzed can be hybridized to biotinylated capture RNA fragments to form biotinylated RNA/genomic DNA complexes. Alternatively, DNA capture probes may be utilized resulting in the formation of biotinylated DNA/genomic DNA hybrids. Streptavidin coated magnetic beads and a magnetic force can be used to separate the biotinylated RNA/genomic DNA complexes from those genomic DNA fragments not present within a biotinylated RNA/genomic DNA complex. The obtained biotinylated RNA/genomic DNA complexes can be treated to remove the captured RNA from the magnetic beads, thereby leaving intact genomic DNA fragments containing a locus to be analyzed. These intact genomic DNA fragments containing the loci to be analyzed can be amplified using, for example, PCR techniques. The amplified genomic DNA fragments can be sequenced using a high-throughput sequencing technology or a next-generation sequencing technology such as Illumina HiSeq™, Illumina MiSeq™, Life Technologies SoLID™ or Ion Torrent™, or Roche 454™.

The sequencing results from the genomic DNA fragments can be used to identify loci as exhibiting or not exhibiting a CA, analogous to the microarray analysis described herein. In some cases, an analysis of the genotype of loci over a length of a chromosome can be performed to determine the length of CA Regions. For example, a stretch of SNP locations that are spaced apart (e.g., spaced about 25 kb to about 100 kb apart) along a chromosome can be evaluated by sequencing, and the sequencing results used to determine not only the presence of a CA Region but also the length of that CA Region. Obtained sequencing results can be used to generate a graph that plots allele dosages along a chromosome. Allele dosage $d_i$ for SNP i can be calculated from adjusted number of captured probes for two alleles ($A_i$ and $B_i$): $d_i = A_i(A_i + B_i)$. An example of such a graph is presented in FIGS. 1 and 2. Determining whether an aberration is germline or somatic can be performed as described herein.

In some cases, a selection process can be used to select loci (e.g., SNP loci) to be evaluated using an assay configured to genotype loci (e.g., SNP array-based assays and sequencing-based assays). For example, any human SNP location can be selected for inclusion in a SNP array-based assay or a sequencing-based assay configured to genotype loci. In some cases, 0.5, 1.0, 1.5, 2.0, 2.5 million or more SNP locations present within the human genome can be evaluated to identify those SNPs that (a) are not present on the Y chromosome, (b) are not mitochondrial SNPs, (c) have a minor allele frequency of at least about five percent in Caucasians, (d) have a minor allele frequency of at least about one percent in three races other than Caucasians (e.g., Chinese, Japanese, and Yoruba), and/or (e) do not have a significant deviation from Hardy Weinberg equilibrium in any of the four races. In some cases, more than 100,000, 150,000, or 200,000 human SNPs can be selected that meet criteria (a) through (e). Of the human SNPs meeting criteria (a) through (e), a group of SNPs (e.g., top 110,000 SNPs) can be selected such that the SNPs have a high degree of allele frequency in Caucasians, cover the human genome in a somewhat evenly spaced manner (e.g., at least one SNP every about 25 kb to about 500 kb), and are not in linkage disequilibrium with another selected SNP for in any of the four races. In some cases, about 40, 50, 60, 70, 80, 90, 100, 110, 120, 130 thousand or more SNPs can be selected as meeting each of these criteria and included in an assay configured to identify CA Regions across a human genome. For example, between about 70,000 and about 90,000 (e.g., about 80,000) SNPs can be selected for analysis with a SNP array-based assay, and between about 45,000 and about 55,000 (e.g., about 54,000) SNPs can be selected for analysis with a sequencing-based assay.

As described herein, any appropriate type of sample can be assessed. For example, a sample containing cancer cells can be assessed to determine if the genome of the cancer cells contains an HRD signature, lacks an HRD signature, has an increased number of Indicator CA Regions or has an increased CA Region Score. Examples of samples containing cancer cells that can be assessed as described herein include, without limitation, tumor biopsy samples (e.g., breast tumor biopsy samples), formalin-fixed, paraffin-embedded tissue samples containing cancer cells, core needle biopsies, fine needle aspirates, and samples containing cancer cells shed from a tumor (e.g., blood, urine or other bodily fluids). For formalin-fixed, paraffin-embedded tissue samples, the sample can be prepared by DNA extraction using a genomic DNA extraction kit optimized for FFPE tissue, including but not limited to those described above (e.g., QuickExtract™ FFPE DNA Extraction Kit (Epicentre™), and QIAamp™ DNA FFPE Tissue Kit (Qiagen™)).

In some cases, laser dissection techniques can be performed on a tissue sample to minimize the number of non-cancer cells within a cancer cell sample to be assessed. In some cases, antibody based purification methods can be used to enrich for cancer cells and/or deplete non-cancer cells. Examples of antibodies that could be used for cancer cell enrichment include, without limitation, anti-EpCAM, anti-TROP-2, anti-c-Met, anti-Folate binding protein, anti-N-Cadherin, anti-CD318, anti-antimesencymal stem cell antigen, anti-Her2, anti-MUC1, anti-EGFR, anti-cytokeratins (e.g., cytokeratin 7, cytokeratin 20, etc.), anti-Caveolin-1, anti-PSA, anti-CA125, and anti-surfactant protein antibodies.

Any type of cancer cell can be assessed using the methods and materials described herein. For example, breast cancer cells, ovarian cancer cells, liver cancer cells, esophageal cancer cells, lung cancer cells, head and neck cancer cells, prostate cancer cells, colon, rectal, or colorectal cancer cells, and pancreatic cancer cells can be assessed to determine if the genome of the cancer cells contains an HRD signature, lacks an HRD signature, has an increased number of Indicator CA Regions or has an increased CA Region Score. In some embodiments, the cancer cells are primary or metastatic cancer cells of ovarian cancer, breast cancer, lung cancer or esophageal cancer.

When assessing the genome of cancer cells for the presence or absence of an HRD signature, one or more (e.g., one, two, three, four, five, six, seven, eight, nine, ten, eleven, twelve, 13, 14, 15, 16, 17, 18, 19, 20, 21, 22, or 23) pairs of chromosomes can be assessed. In some cases, the genome of cancer cells is assessed for the presence or absence of an HRD signature using one or more (e.g., one, two, three, four, five, six, seven, eight, nine, ten, eleven, twelve, 13, 14, 15, 16, 17, 18, 19, 20, 21, 22, 23) pairs of chromosomes.

In some cases, it can be helpful to exclude certain chromosomes from this analysis. For example, in the case of females, a pair to be assessed can include the pair of X sex chromosomes; whereas, in the case of males, a pair of any autosomal chromosomes (i.e., any pair other than the pair of X and Y sex chromosomes) can be assessed. As another example, in some cases the chromosome number 17 pair may be excluded from the analysis. It has been determined that certain chromosomes carry unusually high levels of CA in certain cancers and, thus, it can be helpful to exclude such chromosomes when analyzing samples as described herein from patients having these cancers. In some cases, the sample is from a patient having ovarian cancer, and the chromosome to be excluded is chromosome 17.

Thus, a predefined number of chromosomes may be analyzed to determine the number of Indicator CA Regions (or the CA Region Score or Combined CA Region Score), preferably the number of CA Regions of a length of greater than 9 megabases, 10 megabases, 12 megabases, 14 megabases, more preferably greater than 15 megabases. Alternatively or in addition, the sizes of all identified Indicator CA Regions may be summed up to obtain a total length of Indicator CA Regions.

As described herein, patients having cancer cells (or samples derived therefrom) identified as having an HRD signature status can be classified, based at least in part on such HRD signature, as being likely to respond to a particular cancer treatment regimen. For example, patients having cancer cells with an HRD signature can be classified, based at least in part on such HRD signature, as being likely to respond to a cancer treatment regimen that includes the use of a DNA damaging agent, a synthetic lethality agent (e.g., a PARP inhibitor), radiation, or a combination thereof. In some embodiments the patients are treatment naïve patients. Examples of DNA damaging agents include, without limitation, platinum-based chemotherapy drugs (e.g., cisplatin, carboplatin, oxaliplatin, and picoplatin), anthracyclines (e.g., epirubicin and doxorubicin), topoisomerase I inhibitors (e.g., campothecin, topotecan, and irinotecan), DNA crosslinkers such as mitomycin C, and triazene compounds (e.g., dacarbazine and temozolomide). Synthetic lethality therapeutic approaches typically involve administering an agent that inhibits at least one critical component of a biological pathway that is especially important to a particular tumor cell's survival. For example, when a tumor cell has a deficient homologous repair pathway (e.g., as determined according to the present invention), inhibitors of poly ADP ribose polymerase (or platinum drugs, double strand break repair inhibitors, etc.) can be especially potent against such tumors because two pathways critical to survival become obstructed (one biologically, e.g., by BRCA1 mutation, and the other synthetically, e.g., by administration of a pathway drug). Synthetic lethality approaches to cancer therapy are described in, e.g., O'Brien et al., *Converting cancer mutations into therapeutic opportunities*, EMBO MOL. MED. (2009) 1:297-299. Examples of synthetic lethality agents include, without limitation, PARP inhibitors or double strand break repair inhibitors in homologous repair-deficient tumor cells, PARP inhibitors in PTEN-deficient tumor cells, methotrexate in MSH2-deficient tumor cells, etc. Examples of PARP inhibitors include, without limitation, olaparib, iniparib, and veliparib. Examples of double strand break repair inhibitors include, without limitation, KU55933 (ATM inhibitor) and NU7441 (DNA-PKcs inhibitor). Examples of information that can be used in addition to the presence of an HRD signature to base a classification of being likely to respond to a particular cancer treatment regimen include, without limitation, previous treatment results, germline or somatic DNA mutations, gene or protein expression profiling (e.g., ER/PR/HER2 status, PSA levels), tumor histology (e.g., adenocarcinoma, squamous cell carcinoma, papillary serous carcinoma, mucinous carcinoma, invasive ductal carcinoma, ductal carcinoma in situ (non-invasive), etc.), disease stage, tumor or cancer grade (e.g., well, moderately, or poorly differentiated (e.g., Gleason, modified Bloom Richardson), etc.), number of previous courses of treatment, etc.

Once classified as being likely to respond to a particular cancer treatment regimen (e.g., a cancer treatment regimen that includes the use of a DNA damaging agent, a PARP inhibitor, radiation, or a combination thereof), the cancer patient can be treated with such a cancer treatment regimen. In some embodiments, the patients are treatment naïve patients. The invention thus provides a method of treating a patient comprising detecting an HRD signature as described herein and administering (or recommending or prescribing) a treatment regimen comprising the use of a DNA damaging agent, a PARP inhibitor, radiation, or a combination thereof. Any appropriate method for treating the cancer at issue can be used to treat a cancer patient identified as having cancer cells having an HRD signature. For example, platinum-based chemotherapy drugs or a combination of platinum-based chemotherapy drugs can be used to treat cancer as described elsewhere (see, e.g., U.S. Pat. Nos. 3,892,790, 3,904,663, 7,759,510, 7,759,488 and 7,754,684. In some cases, anthracyclines or a combination of anthracyclines can be used to treat cancer as described elsewhere (see, e.g., U.S. Pat. Nos. 3,590,028, 4,138,480, 4,950,738, 6,087,340, 7,868,040, and 7,485,707). In some cases, topoisomerase I inhibitors or a combination of topoisomerase I inhibitors can be used to treat cancer as described elsewhere (see, e.g., U.S. Pat. Nos. 5,633,016 and 6,403,563. In some cases, PARP inhibitors or a combination of PARP inhibitors can be used to treat cancer as described elsewhere (see, e.g., U.S. Pat. Nos. 5,177,075, 7,915,280, and 7,351,701. In some cases, radiation can be used to treat cancer as described elsewhere (see, e.g., U.S. Pat. No. 5,295,944). In some cases, a combination comprising different agents (e.g., a combination comprising any of platinum-based chemotherapy drugs, anthracyclines, topoisomerase I inhibitors, and/or PARP inhibitors) with or without radiation treatments can be used to treat cancer. In some cases, a combination treatment may comprise any of the above agents or treatments (e.g., a DNA damaging agent, a PARP inhibitor, radiation, or a combination thereof) together with another agent or treatment—e.g., a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite (e.g., 5-flourouracil, methotrexate).

In some cases, patients identified as having cancer cells lacking an HRD signature can be classified, based at least in part on a sample lacking an HRD signature, as being less likely to respond to a treatment regimen that includes a DNA damaging agent, a PARP inhibitor, radiation, or a combination thereof. In turn, such a patient can be classified as likely to respond to a cancer treatment regimen that includes the use of one or more cancer treatment agents not associated with HDR, such as a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite agent (e.g., 5-flourouracil, methotrexate). In some embodiments, the patients are treatment naïve patients. Once classified as being likely to respond to a particular cancer treatment regimen (e.g., a cancer treatment regimen that includes the use of a cancer treatment agent not associated with HDR), the cancer patient can be treated with such a cancer treatment regimen. The invention thus provides a method of treating a patient comprising detecting the absence of an HRD signature as described herein and administering (or recommending or prescribing) a treatment regimen not comprising the use of a DNA damaging agent, a PARP inhibitor, radiation, or a combination thereof. In some embodiments the treatment regimen comprises one or more of a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite agent (e.g., 5-flourouracil, methotrexate). Any appropriate method for the cancer being treated can be used to treat a cancer patient identified as having cancer cells lacking an HRD signature. Examples of information that can be used in addition to the absence of an HRD signature to base a classification of being likely to respond to a particular cancer treatment regimen include, without limitation, previous treatment results, germline or somatic DNA mutations, gene or protein expression profiling (e.g., ER/PR/HER2 status, PSA levels), tumor histology (e.g., adenocarcinoma, squamous cell carcinoma, papillary serous carcinoma, mucinous carcinoma, invasive ductal carcinoma, ductal carcinoma in situ (non-invasive), etc.), disease stage, tumor or cancer grade (e.g., well, moderately, or poorly differentiated (e.g., Gleason, modified Bloom Richardson), etc.), number of previous courses of treatment, etc.

Once treated for a particular period of time (e.g., between one to six months), the patient can be assessed to determine whether or not the treatment regimen has an effect. If a beneficial effect is detected, the patient can continue with the same or a similar cancer treatment regimen. If a minimal or no beneficial effect is detected, then adjustments to the cancer treatment regimen can be made. For example, the dose, frequency of administration, or duration of treatment can be increased. In some cases, additional anti-cancer agents can be added to the treatment regimen or a particular anti-cancer agent can be replaced with one or more different anti-cancer agents. The patient being treated can continue to be monitored as appropriate, and changes can be made to the cancer treatment regimen as appropriate.

In addition to predicting likely treatment response or selecting desirable treatment regimens, an HRD signature can be used to determine a patient's prognosis. Thus, in one aspect, this document features a method for determining a patient's prognosis based at least in part of detecting the presence or absence of an HRD signature in a sample from the patient. The method comprises, or consists essentially of, (a) determining whether a sample from the patient comprises cancer cells (or whether a sample comprises DNA derived from such cells) having an HRD signature (sometimes referred to herein as having high HRD) as described herein (e.g., wherein the presence of more Indicator CA Regions or a higher CA Region Score or Combined CA Region Score than a reference), and (b)(1) determining, based at least in part on the presence of the HRD signature or having high HRD, that the patient has a relatively good prognosis, or (b)(2) determining, based at least in part on the absence of the HRD signature, that the patient has a relatively poor prognosis. Prognosis may include the patient's likelihood of survival (e.g., progression-free survival, overall survival), wherein a relatively good prognosis would include an increased likelihood of survival as compared to some reference population (e.g., average patient with this patient's cancer type/subtype, average patient not having an HRD signature, etc.). Conversely, a relatively poor prognosis in terms of survival would include a decreased likelihood of survival as compared to some reference population (e.g., average patient with this patient's cancer type/subtype, average patient having an HRD signature, etc.).

As described herein, this document provides methods for assessing patients for cells (e.g., cancer cells) having an HRD signature. In some embodiments, one or more clinicians or medical professionals can determine whether a sample from the patient comprises cancer cells (or whether a sample comprises DNA derived from such cells) having an HRD signature. In some cases, one or more clinicians or medical professionals can determine if a patient contains cancer cells having an HRD signature by obtaining a cancer cell sample from the patient and assessing the DNA of cancer cells of the cancer cell sample to determine the presence or absence of an HRD signature as described herein.

In some cases, one or more clinicians or medical professionals can obtain a cancer cell sample from a patient and provide that sample to a testing laboratory having the ability to assess DNA of cancer cells of the cancer cell sample to provide an indication about the presence or absence of an HRD signature as described herein. In some embodiments, the patients are treatment naïve patients. In such cases, the one or more clinicians or medical professionals can determine if a sample from the patient comprises cancer cells (or whether a sample comprises DNA derived from such cells) having an HRD signature by receiving information about the presence or absence of an HRD signature as described herein directly or indirectly from the testing laboratory. For example, a testing laboratory, after assessing DNA of cancer cells for presence or absence of an HRD signature as described herein, can provide a clinician or medical professional with, or access to, a written, electronic, or oral report or medical record that provides an indication about the presence or absence of an HRD signature for a particular patient (or patient sample) being assessed. Such a written, electronic, or oral report or medical record can allow the one or more clinicians or medical professionals to determine if a particular patient being assessed contains cancer cells having an HRD signature.

Once a clinician or medical professional or group of clinicians or medical professionals determines that a particular patient being assessed contains cancer cells having an HRD signature, the clinician or medical professional (or group) can classify that patient as having cancer cells whose genome contains the presence of an HRD signature. In some embodiments, the patients are treatment naïve patients. In some cases, a clinician or medical professional or group of clinicians or medical professionals can diagnose a patient determined to have cancer cells whose genome contains the presence of an HRD signature as having cancer cells deficient in (or likely to be deficient in) HDR. Such a diagnosis can be based solely on a determination that a sample from the patient comprises cancer cells (or whether a sample comprises DNA derived from such cells) having an HRD signature or can be based at least in part on a determination that a sample from the patient comprises cancer cells (or whether a sample comprises DNA derived from such cells) having an HRD signature. For example, a patient determined to have cancer cells having an HRD signature can be diagnosed as likely to be deficient in HDR based on the combination of the presence of an HRD signature and deficient status in one or more tumor suppressor genes (e.g., BRCA1/2, RAD51C), a family history of cancer, or the presence of behavioral risk factors (e.g., smoking).

In some cases, a clinician or medical professional or group of clinicians or medical professionals can diagnose a patient determined to have cancer cells whose genome contains the presence of an HRD signature as having cancer cells likely to contain genetic mutations in one or more genes in the HDR pathway. In some embodiments, the patients are treatment naïve patients. Such a diagnosis can be based solely on a determination that a particular patient being assessed contains cancer cells having a genome containing an HRD signature or can be based at least in part on a determination that a particular patient being assessed contains cancer cells having a genome containing an HRD signature. For example, a patient determined to have cancer cells whose genome contains the presence of an HRD signature can be diagnosed as having cancer cells likely to contain genetic mutations in one or more genes in the HDR pathway based on the combination of the presence of an HRD signature and a family history of cancer, or the presence of behavioral risk factors (e.g., smoking).

In some cases, a clinician or medical professional or group of clinicians or medical professionals can diagnose a patient determined to have cancer cells having an HRD signature as having cancer cells likely to respond to a particular cancer treatment regimen. In some embodiments, the patients are treatment naïve patients. Such a diagnosis can be based solely on a determination that a sample from the patient comprises cancer cells (or whether a sample comprises DNA derived from such cells) having an HRD signature or can be based at least in part on a determination that a sample from the patient comprises cancer cells (or whether a sample comprises DNA derived from such cells) having an HRD signature. For example, a patient determined to have cancer cells having an HRD signature can be diagnosed as being likely to respond to a particular cancer treatment regimen based on the combination of the presence of an HRD signature and deficient status in one or more tumor suppressor genes (e.g., BRCA1/2, RAD51), a family history of cancer, or the presence of behavioral risk factors (e.g., smoking). As described herein, a patient determined to have cancer cells having an HRD signature can be diagnosed as likely to respond to a cancer treatment regimen that includes the use of a platinum-based chemotherapy drug such as cisplatin, carboplatin, oxaliplatin, or picoplatin, an anthracycline such as epirubicin or doxorubicin, a topoisomerase I inhibitor such as campothecin, topotecan, or irinotecan, a PARP inhibitor, radiation, a combination thereof, or a combination of any of the preceding with another anti-cancer agent. In some embodiments, the patients are treatment naïve patients.

Once a clinician or medical professional or group of clinicians or medical professionals determines that a sample from the patient comprises cancer cells (or whether a sample comprises DNA derived from such cells) having a genome lacking an HRD signature, the clinician or medical professional (or group) can classify that patient as having cancer cells whose genome lacks an HRD signature. In some embodiments, the patients are treatment naïve patients. In some cases, a clinician or medical professional or group of clinicians or medical professionals can diagnose a patient determined to have cancer cells containing a genome lacking an HRD signature as having cancer cells likely to have functional HDR. In some cases, a clinician or medical professional or group of clinicians or medical professionals can diagnose a patient determined to have cancer cells containing a genome lacking an HRD signature as having cancer cells that do not likely contain genetic mutations in one or more genes in the HDR pathway. In some cases, a clinician or medical professional or group of clinicians or medical professionals can diagnose a patient determined to have cancer cells containing a genome lacking an HRD signature or containing an increased number of CA Regions that cover the whole chromosome as having cancer cells that are less likely to respond to a platinum-based chemotherapy drug such as cisplatin, carboplatin, oxalaplatin, or picoplatin, an anthracycline such as epirubincin or doxorubicin, a topoisomerase I inhibitor such as campothecin, topotecan, or irinotecan, a PARP inhibitor, or radiation and/or more likely to respond to a cancer treatment regimen that includes the use of a cancer treatment agent not associated with HDR such as one or more taxane agents, growth factor or growth factor receptor inhibitors, anti-metabolite agents, etc. In some embodiments, the patients are treatment naïve patients.

As described herein, this document also provides methods for performing a diagnostic analysis of a nucleic acid sample (e.g., a genomic nucleic acid sample or nucleic acids amplified therefrom) of a cancer patient to determine if a sample from the patient comprises cancer cells (or whether a sample comprises DNA derived from such cells) containing an HRD signature and/or an increased number of CA Regions that cover the whole chromosome. In some embodiments, the patients are treatment naïve patients. For example, one or more laboratory technicians or laboratory professionals can detect the presence or absence of an HRD signature in the genome of cancer cells (or DNA derived therefrom) of the patient or the presence or absence of an increased number of CA Regions that cover the whole chromosome in the genome of cancer cells of the patient. In some cases, one or more laboratory technicians or laboratory professionals can detect the presence or absence of an HRD signature or the presence or absence of an increased number of CA Regions that cover the whole chromosome in the genome of cancer cells of the patient by (a) receiving a cancer cell sample obtained from the patient, receiving a genomic nucleic acid sample obtained from cancer cells obtained from the patient, or receiving a sample containing nucleic acids enriched and/or amplified from such a genomic nucleic acid sample obtained from cancer cells obtained from the patient and (b) performing an analysis (e.g., a SNP array-based assay or a sequencing-based assay) using the received material to detect the presence or absence of an HRD signature or the presence or absence of an increased number of CA Regions that cover the whole chromosome as described herein. In some cases, one or more laboratory technicians or laboratory professionals can receive a sample to be analyzed (e.g., a cancer cell sample obtained from the patient, a genomic nucleic acid sample obtained from cancer cells obtained from the patient, or a sample containing nucleic acids enriched and/or amplified from such a genomic nucleic acid sample obtained from cancer cells obtained from the patient) directly or indirectly from a clinician or medical professional. In some embodiments, the patients are treatment naïve patients.

Once a laboratory technician or laboratory professional or group of laboratory technicians or laboratory professionals detects the presence of an HRD signature as described herein, the laboratory technician or laboratory professional (or group) can associate that HRD signature or the result (or results or a summary of results) of the performed diagnostic analysis with the corresponding patient's name, medical record, symbolic/numerical identifier, or a combination thereof. Such identification can be based solely on detecting the presence of an HRD signature or can be based at least in part on detecting the presence of an HRD signature. For example, a laboratory technician or laboratory professional can identify a patient having cancer cells that were detected to have an HRD signature as having cancer cells potentially deficient in HDR (or as having an increased likelihood of responding to a particular treatment as described at length herein) based on a combination of the presence of an HRD signature and the results of other genetic and biochemical tests performed at the testing laboratory. In some embodiments, the patients are treatment naïve patients.

The converse of the preceding is also true. Namely, once a laboratory technician or laboratory professional or group of laboratory technicians or laboratory professionals detects the absence of an HRD signature, the laboratory technician or laboratory professional (or group) can associate the absence of an HRD signature or the result (or results or a summary of results) of the performed diagnostic analysis with the corresponding patient's name, medical record, symbolic/numerical identifier, or a combination thereof. In some cases, a laboratory technician or laboratory professional or group of laboratory technicians or laboratory professionals can identify a patient having cancer cells that were detected to lack an HRD signature as having cancer cells with potentially intact HDR (or having a decreased likelihood of responding to a particular treatment as described at length herein) either based solely on the absence of an HRD signature or based on a combination of the presence of an HRD signature and the results of other genetic and biochemical tests performed at the testing laboratory. In some embodiments, the patients are treatment naïve patients.

The results of any analyses according to the invention will often be communicated to physicians, genetic counselors and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. For example, graphs or diagrams showing genotype or LOH (or HRD status) information can be used in explaining the results. The statements and visual forms can be recorded on a tangible medium such as papers, computer readable media such as floppy disks, compact disks, flash memory, etc., or in an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an assay is conducted outside the United States, the information and data on a test result may be generated, cast in a transmittable form as described above, and then imported into the United States. Accordingly, the present invention also encompasses a method for producing a transmittable form of information on an HRD signature for at least one patient sample. The method comprises the steps of (1) determining an HRD signature according to methods of the present invention; and (2) embodying the result of the determining step in a transmittable form. The transmittable form is a product of such a method.

Several embodiments of the invention described herein involve a step of correlating the presence of an HRD signature according to the present invention (e.g., the total number of Indicator CA Regions or a CA Region Score or Combined CA Region Score greater than a reference) to a particular clinical feature (e.g., an increased likelihood of a deficiency in the BRCA1 or BRCA2 gene; an increased likelihood of HDR deficiency; an increased likelihood of response to a treatment regimen comprising a DNA damaging agent, an anthracycline, a topoisomerase I inhibitor, radiation, and/or a PARP inhibitor; etc.) and optionally correlating the absence of a HRD signature to one or more other clinical features. Throughout this document, wherever such an embodiment is described, another embodiment of the invention may involve, in addition to or instead of a correlating step, one or both of the following steps: (a) concluding that the patient has the clinical feature based at least in part on the presence or absence of the HRD signature; or (b) communicating that the patient has the clinical feature based at least in part on the presence or absence of the HRD signature.

By way of illustration, but not limitation, one embodiment described in this document is a method of predicting a cancer patient's response to a cancer treatment regimen comprising a DNA damaging agent, an anthracycline, a topoisomerase I inhibitor, radiation, and/or a PARP inhibitor, said method comprising: (1) determining in a sample two or more of (a) an LOH Region Score for the sample; (b) a TAI Region Score for the sample; or (c) an LST Region Score for the sample; and (2)(a) correlating a combination of two or more of the LOH Region Score, the TAI Region Score and the LST Region Score (e.g., a Combined CA Region Score) exceeding a reference to an increased likelihood of responding to the treatment regimen; or optionally (2)(b) correlating a combination of two or more of the LOH Region Score, the TAI Region Score and the LST Region Score (e.g., a Combined CA Region Score) not exceeding a reference to a not increased likelihood of responding to the treatment regimen; or optionally (2)(c) correlating an average (e.g., arithmetic mean) of the LOH Region Score, the TAI Region Score, and the LST Region Score. According to the preceding paragraph, this description of this embodiment is understood to include a description of two alternative related embodiments. One such embodiment provides a method of predicting a cancer patient's response to a cancer treatment regimen comprising a DNA damaging agent, an anthracycline, a topoisomerase I inhibitor, radiation, and/or a PARP inhibitor, said method comprising: (1) determining in a sample two or more of (a) an LOH Region Score for the sample; (b) a TAI Region Score for the sample; or (c) an LST Region Score for the sample; or (d) an average (e.g., arithmetic mean) of the LOH Region Score, the TAI Region Score, and the LST Region Score; and (2)(a) concluding that said patient has an increased likelihood of responding to said cancer treatment regimen based at least in part on a combination of two or more of the LOH Region Score, the TAI Region Score and the LST Region Score (e.g., a Combined CA Region Score) exceeding a reference; or optionally (2)(b) concluding that said patient has a not increased likelihood of responding to said cancer treatment regimen based at least in part on a combination of two or more of the LOH Region Score, the TAI Region Score and the LST Region Score (e.g., a Combined CA Region Score), or an average (e.g., arithmetic mean) of the LOH Region Score, the TAI Region Score, and the LST Region Score, not exceeding a reference. Another such embodiment provides a method of predicting a cancer patient's response to a cancer treatment regimen comprising a DNA damaging agent, an anthracycline, a topoisomerase I inhibitor, radiation, and/or a PARP inhibitor, said method comprising: (1) determining in a sample two or more of (a) an LOH Region Score for the sample; (b) a TAI Region Score for the sample; or (c) an LST Region Score for the sample; or (d) an average (e.g., arithmetic mean) of the LOH Region Score, the TAI Region Score, and the LST Region Score; and (2)(a) communicating that said patient has an increased likelihood of responding to said cancer treatment regimen based at least in part on a combination of two or more of the LOH Region Score, the TAI Region Score and the LST Region Score (e.g., a Combined CA Region Score); or an average (e.g., arithmetic mean) of the LOH Region Score, the TAI Region Score, and the LST Region Score, exceeding a reference; or optionally (2)(b) communicating that said patient has a not increased likelihood of responding to said cancer treatment regimen based at least in part on a combination of two or more of the LOH Region Score, the TAI Region Score and the LST Region Score (e.g., a Combined CA Region Score); or an average (e.g., arithmetic mean) of the LOH Region Score, the TAI Region Score, and the LST Region Score, not exceeding a reference.

In each embodiment described in this document involving correlating a particular assay or analysis output (e.g., total number of Indicator CA Regions greater than a reference number, presence of an HRD signature etc.) to some likelihood (e.g., increased, not increased, decreased, etc.) of some clinical feature (e.g., response to a particular treatment, cancer-specific death, etc.), or additionally or alternatively concluding or communicating such clinical feature based at least in part on such particular assay or analysis output, such correlating, concluding or communicating may comprise assigning a risk or likelihood of the clinical feature occurring based at least in part on the particular assay or analysis output. In some embodiments, such risk is a percentage probability of the event or outcome occurring. In some embodiments, the patient is assigned to a risk group (e.g., low risk, intermediate risk, high risk, etc.). In some embodiments "low risk" is any percentage probability below 5%, 10%, 15%, 20%, 25%, 30%, 35%, 40%, 45%, or 50%. In some embodiments "intermediate risk" is any percentage probability above 5%, 10%, 15%, 20%, 25%, 30%, 35%, 40%, 45%, or 50% and below 15%, 20%, 25%, 30%, 35%, 40%, 45%, 50%, 55%, 60%, 65%, 70%, or 75%. In some embodiments "high risk" is any percentage probability above 25%, 30%, 35%, 40%, 45%, 50%, 55%, 60%, 65%, 70%, 75%, 80%, 85%, 90%, 95%, or 99%.

As used herein, "communicating" a particular piece of information means to make such information known to another person or transfer such information to a thing (e.g., a computer). In some methods of the invention, a patient's prognosis or likelihood of response to a particular treatment is communicated. In some embodiments, the information used to arrive at such a prognosis or response prediction (e.g., HRD signature according to the present invention, etc.) is communicated. This communication may be auditory (e.g., verbal), visual (e.g., written), electronic (e.g., data transferred from one computer system to another), etc. In some embodiments, communicating a cancer classification (e.g., prognosis, likelihood of response, appropriate treatment, etc.) comprises generating a report that communicates the cancer classification. In some embodiments the report is a paper report, an auditory report, or an electronic record. In some embodiments the report is displayed and/or stored on a computing device (e.g., handheld device, desktop computer, smart device, website, etc.). In some embodiments the cancer classification is communicated to a physician (e.g., a report communicating the classification is provided to the physician). In some embodiments the cancer classification is communicated to a patient (e.g., a report communicating the classification is provided to the patient). Communicating a cancer classification can also be accomplished by transferring information (e.g., data) embodying the classification to a server computer and allowing an intermediary or end-user to access such information (e.g., by viewing the information as displayed from the server, by downloading the information in the form of one or more files transferred from the server to the intermediary or end-user's device, etc.).

Wherever an embodiment of the invention comprises concluding some fact (e.g., a patient's prognosis or a patient's likelihood of response to a particular treatment regimen), this may include in some embodiments a computer program concluding such fact, typically after performing an algorithm that applies information on CA Regions according to the present invention.

In each embodiment described herein involving a number of CA Regions (e.g., Indicator CA Regions), or a total combined length of such CA Regions, or an average (e.g., arithmetic mean) of the combined CAR Region scores, the present invention encompasses a related embodiment involving a test value or score (e.g., CA Region Score, LOH Region Score, etc.) derived from, incorporating, and/or, at least to some degree, reflecting such number or length. In other words, the bare CA Region numbers or lengths need not be used in the various methods, systems, etc. of the invention; a test value or score derived from such numbers or lengths may be used. For example, one embodiment of the invention provides a method of treating cancer in a patient, comprising: (1) determining in a sample from said patient two or more of, or an average (e.g., arithmetic mean) of, (a) the number of Indicator LOH Regions, (b) the number of Indicator TAI Regions, or (c) the number of Indicator LST Regions; (2) providing one or more test values derived from said number of Indicator LOH Regions, Indicator TAI Regions, and/or Indicator LST Regions; (3) comparing said test value(s) to one or more reference values (e.g., reference values derived from the number of Indicator LOH regions, Indicator TAI Regions, and/or Indicator LST Regions in a reference population (e.g., mean, median, terciles, quartiles, quintiles, etc.)); and (4)(a) administering to said patient an anti-cancer drug, or recommending or prescribing or initiating a treatment regimen comprising chemotherapy and/or a synthetic lethality agent based at least in part on said comparing step revealing that one or more of the test values is greater (e.g., at least 2-, 3-, 4-, 5-, 6-, 7-, 8-, 9-, or 10-fold greater; at least 1, 2, 3, 4, 5, 6, 7, 8, 9, or 10 standard deviations greater) than at least one said reference value; or optionally (4)(b) recommending or prescribing or initiating a treatment regimen not comprising chemotherapy and/or a synthetic lethality agent based at least in part on said comparing step revealing that one or more of the test values is not greater (e.g., not more than 2-, 3-, 4-, 5-, 6-, 7-, 8-, 9-, or 10-fold greater; not more than 1, 2, 3, 4, 5, 6, 7, 8, 9, or 10 standard deviations greater) than at least one said reference value. The invention encompasses, mutatis mutandis, corresponding embodiments where the test value or score is used to determine the patient's prognosis, the patient's likelihood of response to a particular treatment regimen, the patient's or patient's sample's likelihood of having a BRCA1, BRCA2, RAD51C or HDR deficiency, etc.

Figure 8:
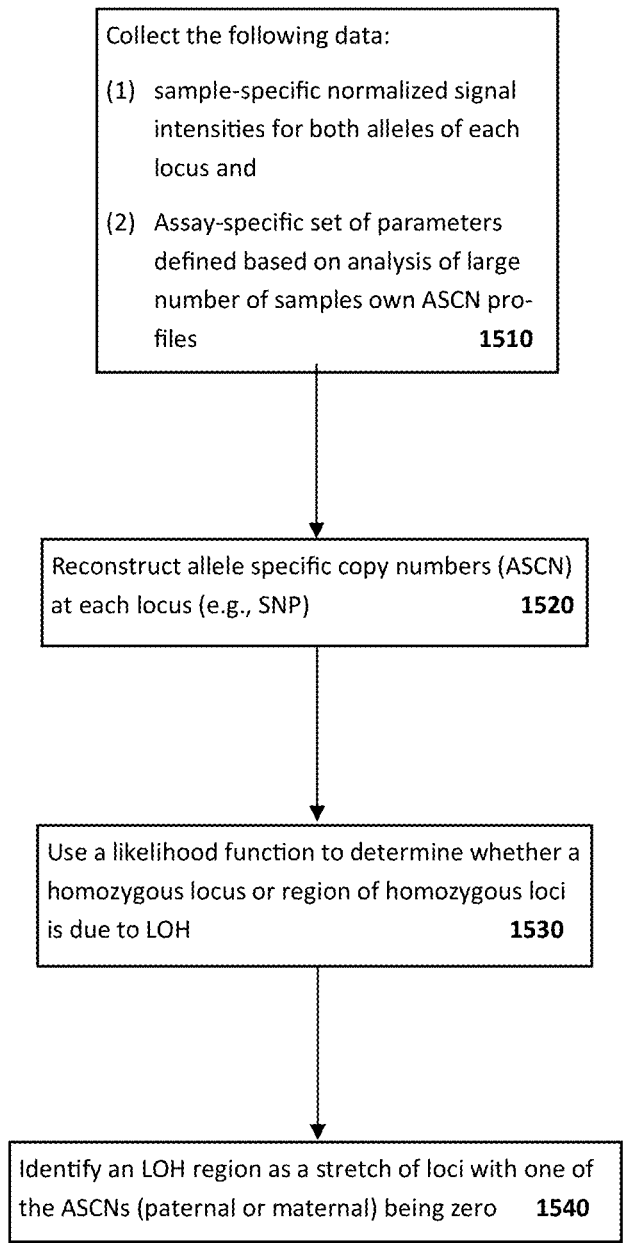
FIG. 8 is a graph plotting the number of LOH regions longer than 15 Mb and shorter than the entire chromosome for ovarian cancer cell samples with somatic BRCA mutations, with germline BRCA mutations, with low BRCA1 expression, or with intact BRCA (BRCA normal). The size of the circles is proportional to the number of samples with such number of LOH regions.

FIG. 8 shows an exemplary process by which a computing system (or a computer program (e.g., software) containing computer-executable instructions) can identify LOH loci or regions from genotype data as described herein. This process may be adapted to use in determining TAI and LST as will be apparent to those skilled in the art. If the observed ratio of the signals of two alleles, A and B, is two to one, there are two possibilities. The first possibility is that cancer cells have LOH with deletion of allele B in a sample with 50% contamination with normal cells. The second possibility is that there is no LOH but allele A is duplicated in a sample with no contamination with normal cells. The process begins at box 1500, where the following data are collected by the computing system; (1) sample-specific normalized signal intensities for both alleles of each locus and (2) assay-specific (specific for different SNP arrays and for sequence based approach) set of parameters defined based on analysis of large number of samples with known ASCN profiles. As described herein, any appropriate assay such as a SNP array-based assay or sequencing-based assay can be used to assess loci along a chromosome for homozygosity or heterozygosity. In some cases, a system including a signal detector and a computer can be used to collect data (e.g., fluorescent signals or sequencing results) regarding the homozygous or heterozygous nature of the plurality of loci (e.g., sample-specific normalized signal intensities for both alleles of each locus). At box 1510, allele specific copy numbers (ASCN) are reconstructed at each locus (e.g., each SNP). ASCNs are the numbers of copies of both paternal and maternal alleles. At box 1530, a likelihood function is used to determine whether a homozygous locus or region of homozygous loci is due to LOH. This can be conceptually analogous to a previously described algorithm designed to reconstruct total copy number (rather than ASCN) at each locus (e.g., SNP). See International Application No. PCT/US2011/026098 to Abkevich et al. The likelihood function can be maximized over ASCN of all loci, level of contamination with benign tissue, total copy number averaged over the whole genome, and sample specific noise level. At box 1540, an LOH region is determined as a stretch of SNPs with one of the ASCNs (paternal or maternal) being zero. In some embodiments, the computer process further comprises a step of inquiring or determining whether a patient is treatment naïve.

Figure 3:
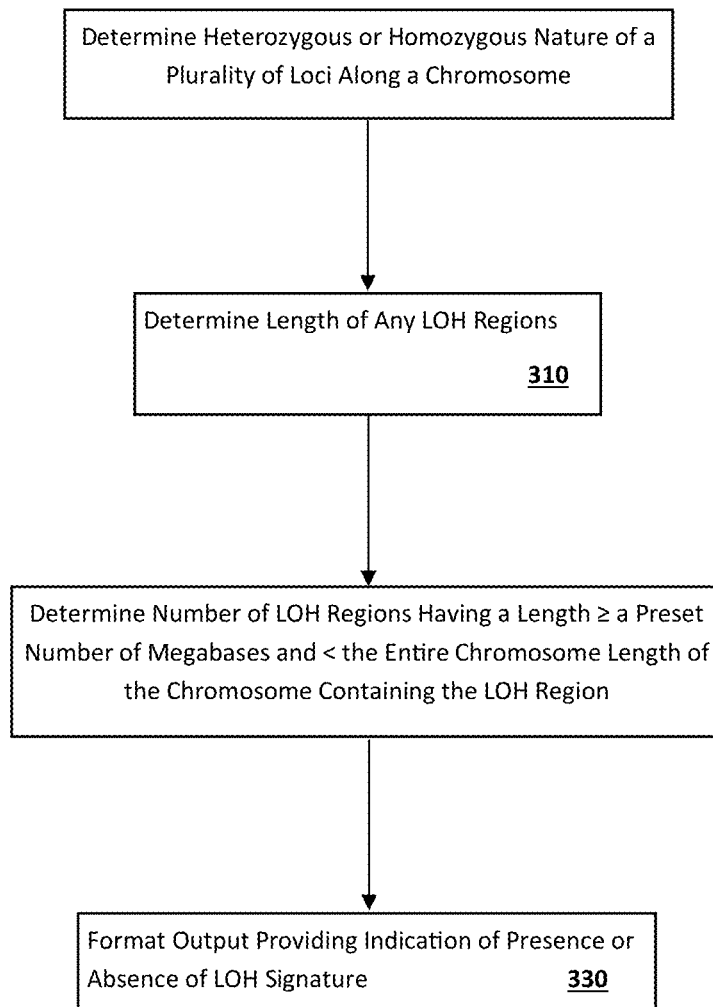
FIG. 3 is a flow chart of an example process for assessing the genome of a cell (e.g., a cancer cell) for an HRD signature.

FIG. 3 shows an exemplary process by which a computing system can determine the presence or absence of an LOH signature and is included to illustrate how this process can, as will be apparent to those skilled in the art, be applied to TAI and LST. The process begins at box 300, where data regarding the homozygous or heterozygous nature of a plurality of loci along a chromosome is collected by the computing system. As described herein, any appropriate assay such as a SNP array-based assay or sequencing-based assay can be used to assess loci along a chromosome for homozygosity or heterozygosity. In some cases, a system including a signal detector and a computer can be used to collect data (e.g., fluorescent signals or sequencing results) regarding the homozygous or heterozygous nature of the plurality of loci. At box 310, data regarding the homozygous or heterozygous nature of a plurality of loci as well as the location or spatial relationship of each locus is assessed by the computing system to determine the length of any LOH regions present along a chromosome. At box 320, data regarding the number of LOH regions detected and the length of each detected LOH region is assessed by the computing system to determine the number of LOH regions that have a length (a) greater than or equal to a preset number of Mb (e.g., 15 Mb) and (b) less than the entire length of the chromosome containing that LOH region. Alternatively the computing system can determine the total or combined LOH length as described above. At box 330, the computing system formats an output providing an indication of the presence or absence of an HRD signature. Once formatted, the computing system can present the output to a user (e.g., a laboratory technician, clinician, or medical professional). As described herein, the presence or absence of an HRD signature can be used to provide an indication about a patient's likely HDR status, an indication about the likely presence or absence of genetic mutations in genes of the HDR pathway, and/or an indication about possible cancer treatment regimens.

Figure 4:
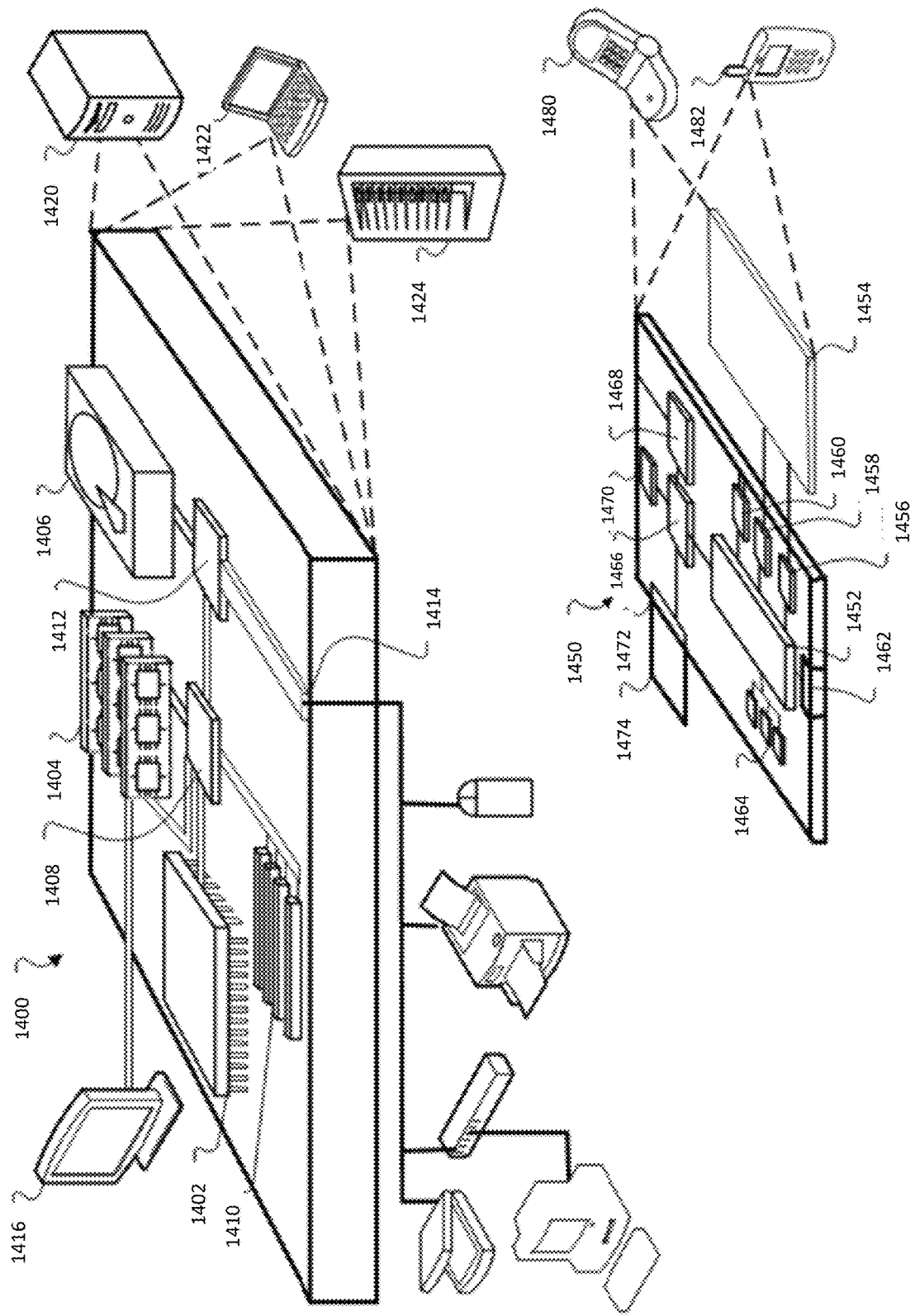
FIG. 4 is a diagram of an example of a computer device and a mobile computer device that can be used to implement the techniques described herein.

FIG. 4 is a diagram of an example of a computer device 1400 and a mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some cases, a computing system provided herein can be configured to include one or more sample analyzers. A sample analyzer can be configured to produce a plurality of signals about genomic DNA of at least one pair of human chromosomes of a cancer cell. For example, a sample analyzer can produce signals that are capable of being interpreted in a manner that identifies the genotype of loci along a chromosome. In some cases, a sample analyzer can be configured to carry out one or more steps of a SNP array-based assay or sequencing-based assay and can be configured to produce and/or capture signals from such assays. In some cases, a computing system provided herein can be configured to include a computing device. In such cases, the computing device can be configured to receive signals from a sample analyzer. The computing device can include computer-executable instructions or a computer program (e.g., software) containing computer-executable instructions for carrying out one or more of the methods or steps described herein. In some cases, such computer-executable instructions can instruct a computing device to analyze signals from a sample analyzer, from another computing device, from a SNP array-based assay, or from a sequencing-based assay. The analysis of such signals can be carried out to determine genotypes, homozygosity or other chromosomal aberration s at certain loci, regions of CA, the number of CA Regions, to determine the size of CA Regions, to determine the number of CA Regions having a particular size or range of sizes, to determine whether or not a sample is positive for an HRD signature, to determine the number of Indicator CA Regions in at least one pair of human chromosomes, to determine a likelihood of a deficiency in BRCA1 and/or BRCA2 genes, to determine a likelihood of a deficiency in HDR, to determine a likelihood that a cancer patient will respond to a particular cancer treatment regimen (e.g., a regimen that includes a DNA damaging agent, an anthracycline, a topoisomerase I inhibitor, radiation, a PARP inhibitor, or a combination thereof), or to determine a combination of these items.

In some cases, a computing system provided herein can include computer-executable instructions or a computer program (e.g., software) containing computer-executable instructions for formatting an output providing an indication about the number of CA Regions, the size of CA Regions, the number of CA Regions having a particular size or range of sizes, whether or not a sample is positive for an HRD signature, the number of Indicator CA Regions in at least one pair of human chromosomes, a likelihood of a deficiency in BRCA1 and/or BRCA2 genes, to determine a likelihood of a deficiency in HDR, a likelihood that a cancer patient will respond to a particular cancer treatment regimen (e.g., a regimen that includes a DNA damaging agent, an anthracycline, a topoisomerase I inhibitor, radiation, a PARP inhibitor, or a combination thereof), or a combination of these items. In some cases, a computing system provided herein can include computer-executable instructions or a computer program (e.g., software) containing computer-executable instructions for determining a desired cancer treatment regimen for a particular patient based at least in part on the presence or absence of an HRD signature or on the number of Indicator CA Regions.

In some cases, a computing system provided herein can include a pre-processing device configured to process a sample (e.g., cancer cells) such that a SNP array-based assay or sequencing-based assay can be performed. Examples of pre-processing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

This document also provides kits for assessing samples (e.g., cancer cells) as described herein. For example, this document provides kits for assessing cancer cells for the presence of an HRD signature or to determine the number of Indicator CA Regions in at least one pair of human chromosomes. A kit provided herein can include either SNP probes (e.g., an array of SNP probes for carrying out a SNP array-based assay described herein) or primers (e.g., primers designed for sequencing SNP regions via a sequencing-based assay) in combination with a computer program product containing computer-executable instructions for carrying out one or more of the methods or steps described herein (e.g., computer-executable instructions for determining the number of Indicator CA Regions). In some cases, a kit provided herein can include at least 500, 1000, 10,000, 25,000, or 50,000 SNP probes capable of hybridizing to polymorphic regions of human genomic DNA. In some cases, a kit provided herein can include at least 500, 1000, 10,000, 25,000, or 50,000 primers capable of sequencing polymorphic regions of human genomic DNA. In some cases, a kit provided herein can include one or more other ingredients for performing a SNP array-based assay or a sequencing-based assay. Examples of such other ingredients include, without limitation, buffers, sequencing nucleotides, enzymes (e.g., polymerases), etc. This document also provides the use of any appropriate number of the materials provided herein in the manufacture of a kit for carrying out one or more of the methods or steps described herein. For example, this document provides the use of a collection of SNP probes (e.g., a collection of 10,000 to 100,000 SNP probes) and a computer program product provided herein in the manufacture of a kit for assessing cancer cells for the presence of an HRD signature. As another example, this document provides the use of a collection of primers (e.g., a collection of 10,000 to 100,000 primers for sequencing SNP regions) and a computer program product provided herein in the manufacture of a kit for assessing cancer cells for the presence of an HRD signature.

SPECIFIC EMBODIMENTS

As follows are specific embodiments of the present disclosure, that is, exemplary but non-limiting details of methods and systems according to the more general description above.

In some embodiments, the sample used is a frozen tumor sample. In some embodiments, the sample is from a particular breast cancer subtype chosen from triple negative, ER+/HER2−, ER−/HER2+, or ER+/HER2+. In some embodiments, the laboratory assay portion of the method, system, etc. comprises assaying the sample to sequence the BRCA1 and/or BRCA2 genes (as well as any other gene or genes in Table 1). In some embodiments, the laboratory assay portion of the method, system, etc. comprises assaying the sample to determine the allele dosage (e.g., genotype, copy number, etc.) for at least 10,000, 20,000, 30,000, 40,000, 50,000, 60,000, 70,000, 80,000, 90,000, 100,000 or more selected SNPs across the complete genome. In some embodiments the SNP analysis is done using an oligonucleotide microarray as discussed above. In some embodiments the BRCA sequence analysis, the SNP analysis, or both are performed using a probe capture (e.g., probes to each SNP to be analyzed and/or probes to capture the entire coding region of BRCA1 and/or BRCA2) with subsequent PCR enrichment technique (e.g., Agilent™ SureSelect XT). In some embodiments the BRCA sequence analysis, the SNP analysis, or both are performed by processing the output from the enrichment technique using a "next-generation" sequencing platform (e.g., Illumina™ HiSeq2500). In some embodiments the sample is analyzed for BRCA1/2 somatic and/or germline mutations, which may include large rearrangements. In some embodiments, the sample is analyzed for BRCA1 promoter methylation (e.g., by a qPCR assay (e.g., SA Biosciences)). In some embodiments, a sample is determined to have high methylation (or are "methylated") if the sample has greater than 10% (or 5%, 15%, 20%, 25%, 30%, 35%, 40%, 45%, 50%) methylation (e.g., % of BRCA1 or BRCA2 promoter CpGs methylated). In some embodiments, DNA from a patient's matched normal (non-tumor) tissue may be analyzed, e.g., to determine whether BRCA1 or BRCA2 mutations are germline or somatic.

In some embodiments, LOH Region Score can be calculated by counting the number of LOH regions that are >15 Mb in length, but shorter than the length of a complete chromosome. In some embodiments, TAI Region Score can be calculated by counting the number of telomeric regions >11 Mb in length with allelic imbalance that extends to one of the subtelomeres, but does not cross the centromere. In some embodiments, LST Region Score can be calculated by counting the number of breakpoints between regions longer than 10 megabases having stable copy number after filtering out regions shorter than 3 megabases. In some embodiments the LST Region Score can be modified by adjusting it by ploidy: LSTm=LST−kP, where P is ploidy and k is a constant (in some embodiments, k=15.5). In some embodiments BRCA1/2 deficiency can be defined as loss of function resulting from a BRCA1 or BRCA2 mutation, or methylation of the BRCA1 or BRCA2 promoter region, together with LOH in the affected gene. In some embodiments response to treatment can be partial complete response ("pCR"), which in some embodiments can be defined as Miller-Payne 5 status following treatment (e.g., neoadjuvant).

In some embodiments, the claimed method predicts BRCA deficiency with a p-value of at least $8*10^{-12}$, $6*10^{-6}$, 0.0009, 0.01, 0.03, $2*10^{-16}$, $3*10^{-6}$, $10^{-6}$, 0.0009, $8*10^{-12}$, $2*10^{-16}$, $8*10^{-8}$, $6*10^{-6}$, $3*10^{-6}$, or 0.0002 (e.g., each CA Region Score is predefined and optionally multiple scores are combined in such a way as to yield these p-values). In some embodiments p-values are calculated according to Kolmogorov-Smirnov test. In some embodiments HRD scores and age at diagnosis can be coded as a numeric (e.g., integer) variable, breast cancer stage and subtype can be coded as categorical variables, and grade can be analyzed as either a numeric or categorical variable, or both.

In some embodiments p-values are two-sided. In some embodiments, logistic regression analysis can be used to predict BRCA1/2 deficiency based on an HRD score as disclosed herein, including the HRD-combined score). In some embodiments, the various CA Region Scores are correlated according to (e.g., defined in order to achieve) the following correlation coefficients: LOH Region Score and TAI Region Score=0.69 ($p=10^{-39}$), between LOH and LST=0.55 ($p=2*10^{-19}$), and between TAI and LST=0.39 ($p=10^{-9}$).

In some embodiments the method combines the LOH Region Score and TAI Region Score as follows to detect BRCA1/2 deficiency and/or predict therapy response (e.g., platinum therapy response, e.g., cisplatin): Combined CA Region Score=0.32*LOH Region Score+0.68*TAI Region Score. In some embodiments the method combines the LOH Region Score, TAI Region Score, and LST Region Score as follows to detect BRCA1/2 deficiency and/or predict therapy response (e.g., platinum therapy response, e.g., cisplatin): Combined CA Region Score=0.21*LOH Region Score+0.67*TAI Region Score+0.12*LST Region Score. In some embodiments the method combines the LOH Region Score, TAI Region Score, and LST Region Score as follows to detect BRCA1/2 deficiency and/or predict therapy response (e.g., platinum therapy response, e.g., cisplatin): Combined CA Region Score=0.11*LOH Region Score+0.25*TAI Region Score+0.12*LST Region Score. In some embodiments the method combines the LOH Region Score, TAI Region Score, and LST Region Score as follows to detect BRCA1/2 deficiency and/or predict therapy response (e.g., platinum therapy response, e.g., cisplatin): Combined CA Region Score=Arithmetic Mean of LOH Region Score, TAI Region Score and LST Region Score.

In some embodiments, BRCA deficiency status and HRD status can be combined to predict therapy response. For example, the disclosure can include a method of predicting patient (e.g., triple negative breast cancer patient) response to a cancer treatment regimen comprising a DNA damaging agent (e.g., platinum agent, e.g., cisplatin), an anthracycline, a topoisomerase I inhibitor, radiation, and/or a PARP inhibitor, the method comprising:

determining, in a cancer cell from a patient sample, the number of Indicator CA Regions (e.g., Indicator LOH Regions, Indicator TAI Regions, Indicator LST Regions, or any combination thereof) in at least one pair of human chromosomes of a cancer cell of said cancer patient;

determining whether a cancer cell from a patient sample is deficient in BRCA1 or BRCA2 (e.g., deleterious mutation, high promoter methylation); and diagnosing a patient in whose sample either (a) said number of Indicator CA Regions is greater than a reference number or (b) there is a BRCA1 or BRCA2 deficiency, or both (a) and (b), as having an increased likelihood of responding to said cancer treatment regimen.

ADDITIONAL SPECIFIC EMBODIMENTS

Embodiment 1

An in vitro method of predicting patient response to a cancer treatment regimen comprising a DNA damaging agent, anthracycline, topoisomerase I inhibitor, or PARP inhibitor, the method comprising:
 (1) determining, in a sample comprising a cancer cell, the number of Indicator CA Regions comprising at least two types chosen from Indicator LOH Regions, Indicator TAI Regions, or Indicator LST Regions in at least one pair of human chromosomes of a cancer cell of said cancer patient; and
 (2) diagnosing a patient in whose sample said number of Indicator LOH Regions, Indicator TAI Regions, or Indicator LST Regions is greater than a reference number as having an increased likelihood of responding to said cancer treatment regimen.

Embodiment 2

The method of Embodiment 1, said at least one pair of human chromosomes is representative of the entire genome.

Embodiment 3

The method of Embodiment 1 or Embodiment 2, wherein said Indicator CA Regions are determined in at least two, three, four, five, six, seven, eight, nine, ten, 11, 12, 13, 14, 15, 16, 17, 18, 19, 20 or 21 pairs of human chromosomes.

Embodiment 4

The method of any one of Embodiments 1-3, wherein said cancer cell is an ovarian, breast, or esophageal cancer cell.

Embodiment 5

The method of any one of Embodiments 1-4, wherein the reference number of Indicator LOH Regions is two, three, four, five, six, seven, eight, nine, ten, 11, 12, 13, 14, 15, 16, 17, 18, 19, 20, 21, 22, 23, 24, 25, 30, 35, 40, 45, 50 or more, the reference number of Indicator TAI Regions is two, three, four, five, six, seven, eight, nine, ten, 11, 12, 13, 14, 15, 16, 17, 18, 19, 20, 21, 22, 23, 24, 25, 30, 35, 40, 45, 50 or more, and the reference number of Indicator LST Regions is two, three, four, five, six, seven, eight, nine, ten, 11, 12, 13, 14, 15, 16, 17, 18, 19, 20, 21, 22, 23, 24, 25, 30, 35, 40 45, 50 or more.

Embodiment 6

The method of any one of Embodiments 1-5, wherein said Indicator LOH Regions are defined as LOH Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length but less than a either a complete chromosome or a complete chromosome arm, said Indicator TAI Regions are defined as TAI Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length but not extending across a centromere, and said Indicator LST Regions are defined as LST Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length.

Embodiment 7

The method of any one of Embodiments 1-6, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, or said PARP inhibitor is iniparib, olaparib or velapirib.

Embodiment 8

The method of any one of Embodiments 1-7, further comprising administering said cancer treatment regimen to said patient diagnosed as having an increased likelihood of responding to said cancer treatment regimen.

Embodiment 9

An in vitro method of predicting patient response to a cancer treatment regimen comprising a platinum agent, the method comprising:
  (1) determining, in a sample comprising a cancer cell, the number of Indicator CA Regions comprising at least two types chosen from Indicator LOH Regions, Indicator TAI Regions, or Indicator LST Regions in at least one pair of human chromosomes of a cancer cell of said cancer patient;
  (2) determining whether a sample comprising a cancer cell is deficient in BRCA1 or BRCA2; and
  (3) diagnosing a patient in whose sample either (a) said number of Indicator LOH Regions, Indicator TAI Regions, or Indicator LST Regions is greater than a reference number or (b) there is a BRCA1 or BRCA2 deficiency, or both (a) and (b), as having an increased likelihood of responding to said cancer treatment regimen.

Embodiment 10

The method of Embodiment 9, said at least one pair of human chromosomes is representative of the entire genome.

Embodiment 11

The method of Embodiment 9 or Embodiment 10, wherein said Indicator CA Regions are determined in at least two, three, four, five, six, seven, eight, nine, ten, 11, 12, 13, 14, 15, 16, 17, 18, 19, 20 or 21 pairs of human chromosomes.

Embodiment 12

The method of any one of Embodiments 9-11, wherein said cancer cell is an ovarian, breast, or esophageal cancer cell.

Embodiment 13

The method of any one of Embodiments 9-12, wherein the reference number of Indicator LOH Regions is two, three, four, five, six, seven, eight, nine, ten, 11, 12, 13, 14, 15, 16, 17, 18, 19, 20, 21, 22, 23, 24, 25, 30, 35, 40, 45, 50 or more, the reference number of Indicator TAI Regions is two, three, four, five, six, seven, eight, nine, ten, 11, 12, 13, 14, 15, 16, 17, 18, 19, 20, 21, 22, 23, 24, 25, 30, 35, 40, 45, 50 or more, and the reference number of Indicator LST Regions is two, three, four, five, six, seven, eight, nine, ten, 11, 12, 13, 14, 15, 16, 17, 18, 19, 20, 21, 22, 23, 24, 25, 30, 35, 40 45, 50 or more.

Embodiment 14

The method of any one of Embodiments 9-13, wherein said Indicator LOH Regions are defined as LOH Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length but less than a either a complete chromosome or a complete chromosome arm, said Indicator TAI Regions are defined as TAI Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length but not extending across a centromere, and said Indicator LST Regions are defined as LST Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length.

Embodiment 15

The method of any one of Embodiments 9-14, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, or said PARP inhibitor is iniparib, olaparib or velapirib.

Embodiment 16

The method of any one of Embodiments 9-15, wherein said sample is deficient in BRCA1 or BRCA2 if a deleterious mutation, loss of heterozygosity or high methylation is detected in either BRCA1 or BRCA2 in said sample.

Embodiment 17

The method of Embodiment 16, wherein high methylation is detected if methylation is detected in at least 5%, 10%, 15%, 20%, 25%, 30%, 35%, 40%, 45%, or 50% or more of BRCA1 or BRCA2 promoter CpGs analyzed.

Embodiment 18

An in vitro method of predicting patient response to a cancer treatment regimen comprising a DNA damaging agent, anthracycline, topoisomerase I inhibitor, or PARP inhibitor, the method comprising:
(1) determining, in a sample comprising a cancer cell, the number of Indicator CA Regions comprising at least two types chosen from Indicator LOH Regions, Indicator TAI Regions, or Indicator LST Regions in at least one pair of human chromosomes of a cancer cell of said cancer patient;
(2) providing a test value derived from the number of said Indicator CA Regions;
(3) comparing said test value to one or more reference values derived from the number of said Indicator CA Regions in a reference population; and
(4) diagnosing a patient in whose sample said test value is greater than said one or more reference numbers as having an increased likelihood of responding to said cancer treatment regimen.

Embodiment 19

The method of Embodiment 18, said at least one pair of human chromosomes is representative of the entire genome.

Embodiment 20

The method of Embodiment 18 or Embodiment 19, wherein said Indicator CA Regions are determined in at least two, three, four, five, six, seven, eight, nine, ten, 11, 12, 13, 14, 15, 16, 17, 18, 19, 20 or 21 pairs of human chromosomes.

Embodiment 21

The method of any one of Embodiments 18-20, wherein said cancer cell is an ovarian, breast, or esophageal cancer cell.

Embodiment 22

The method of any one of Embodiments 18-21, wherein the reference number of Indicator LOH Regions is two, three, four, five, six, seven, eight, nine, ten, 11, 12, 13, 14, 15, 16, 17, 18, 19, 20, 21, 22, 23, 24, 25, 30, 35, 40, 45, 50 or more, the reference number of Indicator TAI Regions is two, three, four, five, six, seven, eight, nine, ten, 11, 12, 13, 14, 15, 16, 17, 18, 19, 20, 21, 22, 23, 24, 25, 30, 35, 40, 45, 50 or more, and the reference number of Indicator LST Regions is two, three, four, five, six, seven, eight, nine, ten, 11, 12, 13, 14, 15, 16, 17, 18, 19, 20, 21, 22, 23, 24, 25, 30, 35, 40 45, 50 or more.

Embodiment 23

The method of any one of Embodiments 18-22, wherein said Indicator LOH Regions are defined as LOH Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length but less than a either a complete chromosome or a complete chromosome arm, said Indicator TAI Regions are defined as TAI Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length but not extending across a centromere, and said Indicator LST Regions are defined as LST Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length.

Embodiment 24

The method of any one of Embodiments 18-23, wherein said DNA damaging agent is cisplatin, carboplatin, oxaliplatin, or picoplatin, said anthracycline is epirubincin or doxorubicin, said topoisomerase I inhibitor is campothecin, topotecan, or irinotecan, or said PARP inhibitor is iniparib, olaparib or velapirib.

Embodiment 25

The method of any one of Embodiments 18-24, further comprising diagnosing a patient in whose sample said test value is not greater than said one or more reference numbers as not having an increased likelihood of responding to said cancer treatment regimen and either (5)(a) recommending, prescribing, initiating or continuing a treatment regimen comprising a DNA damaging agent, anthracycline, topoisomerase I inhibitor, or PARP inhibitor in said patient diagnosed as having an increased likelihood of responding to said cancer treatment regimen; or (5)(b) recommending, prescribing, initiating or continuing a treatment regimen not comprising a DNA damaging agent, anthracycline, topoisomerase I inhibitor, or PARP inhibitor in said patient diagnosed as not having an increased likelihood of responding to said cancer treatment regimen.

Embodiment 26

The method of any one of Embodiments 18-25, wherein said test value is derived by calculating the arithmetic mean of the numbers of Indicator LOH Regions, Indicator TAI Regions and Indicator LST Regions in said sample as follows:

$$\text{Test Value} = \frac{(\text{\# of Indicator } LOH \text{ Regions}) + (\text{\# of Indicator } TAI \text{ Regions}) + (\text{\# of Indicator } LST \text{ Regions})}{3}$$

and said one or more reference values were derived by calculating the arithmetic mean of the numbers of Indicator LOH Regions, Indicator TAI Regions and Indicator LST Regions in samples from said reference population as follows:

$$\text{Test Value} = \frac{(\text{\# of Indicator } LOH \text{ Regions}) + (\text{\# of Indicator } TAI \text{ Regions}) + (\text{\# of Indicator } LST \text{ Regions})}{3}$$

Embodiment 27

The method of any one of Embodiments 18-26, comprising diagnosing a patient in whose sample said test value is at least 2-, 3-, 4-, 5-, 6-, 7-, 8-, 9-, or 10-fold greater, at least 1, 2, 3, 4, 5, 6, 7, 8, 9, or 10 standard deviations greater, or at least 5%, 10%, 15%, 20%, 25%, 30%, 35%, 40%, 45%, 50%, 55%, 60%, 65%, 70%, 75%, 80%, 85%, 90%, 95% greater than said one or more reference numbers as having an increased likelihood of responding to said cancer treatment regimen.

Embodiment 28

A method of treating cancer patients, comprising:
(1) determining, in a sample comprising a cancer cell, the number of Indicator CA Regions comprising Indicator LOH Regions, Indicator TAI Regions, and Indicator LST Regions in at least one pair of human chromosomes of a cancer cell of said cancer patient;
(2) providing a test value derived from the number of said Indicator CA Regions;
(3) comparing said test value to one or more reference values derived from the number of said Indicator CA Regions in a reference population; and either
(4)(a) recommending, prescribing, initiating or continuing a treatment regimen comprising a DNA damaging agent, anthracycline, topoisomerase I inhibitor, or PARP inhibitor in a patient in whose sample the test value is greater than at least one said reference value; or
(4)(b) recommending, prescribing, initiating or continuing a treatment regimen comprising a DNA damaging agent, anthracycline, topoisomerase I inhibitor, or PARP inhibitor in a patient in whose sample the test value is not greater than at least one said reference value.

Embodiment 29

The method of Embodiment 28, said at least one pair of human chromosomes is representative of the entire genome.

Embodiment 30

The method of Embodiment 28 or Embodiment 29, wherein said Indicator CA Regions are determined in at least two, three, four, five, six, seven, eight, nine, ten, 11, 12, 13, 14, 15, 16, 17, 18, 19, 20 or 21 pairs of human chromosomes.

Embodiment 31

The method of any one of Embodiments 28-30, wherein said cancer cell is an ovarian, breast, or esophageal cancer cell.

Embodiment 32

The method of any one of Embodiments 28-31, wherein the reference number of Indicator LOH Regions is two, three, four, five, six, seven, eight, nine, ten, 11, 12, 13, 14, 15, 16, 17, 18, 19, 20, 21, 22, 23, 24, 25, 30, 35, 40, 45, 50 or more, the reference number of Indicator TAI Regions is two, three, four, five, six, seven, eight, nine, ten, 11, 12, 13, 14, 15, 16, 17, 18, 19, 20, 21, 22, 23, 24, 25, 30, 35, 40, 45, 50 or more, and the reference number of Indicator LST Regions is two, three, four, five, six, seven, eight, nine, ten, 11, 12, 13, 14, 15, 16, 17, 18, 19, 20, 21, 22, 23, 24, 25, 30, 35, 40 45, 50 or more.

Embodiment 33

The method of any one of Embodiments 28-32, wherein said Indicator LOH Regions are defined as LOH Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length but less than a either a complete chromosome or a complete chromosome arm, said Indicator TAI Regions are defined as TAI Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length but not extending across a centromere, and said Indicator LST Regions are defined as LST Regions at least two, three, four, five, six, seven, eight, nine, ten, 11, 12, 13, 14, 15, 16, 17, 18, 19, 20, 21, 22, 23, 24, 25, 30, 35, 40, 45, 50 or more megabases in length.

Embodiment 34

The method of any one of Embodiments 28-33, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, or said PARP inhibitor is iniparib, olaparib or velapirib.

Embodiment 35

The method of any one of Embodiments 28-34, wherein said test value is derived by calculating the arithmetic mean of the numbers of Indicator LOH Regions, Indicator TAI Regions and Indicator LST Regions in said sample as follows:

$$\text{Test Value} = \frac{(\text{\# of Indicator } LOH \text{ Regions}) + (\text{\# of Indicator } TAI \text{ Regions}) + (\text{\# of Indicator } LST \text{ Regions})}{3}$$

and said one or more reference values were derived by calculating the arithmetic mean of the numbers of Indicator LOH Regions, Indicator TAI Regions and Indicator LST Regions in samples from said reference population as follows:

$$\text{Test Value} = \frac{(\text{\# of Indicator } LOH \text{ Regions}) + (\text{\# of Indicator } TAI \text{ Regions}) + (\text{\# of Indicator } LST \text{ Regions})}{3}$$

Embodiment 36

The method of any one of Embodiments 28-35, comprising diagnosing a patient in whose sample said test value is at least 2-, 3-, 4-, 5-, 6-, 7-, 8-, 9-, or 10-fold greater, at least 1, 2, 3, 4, 5, 6, 7, 8, 9, or 10 standard deviations greater, or at least 5%, 10%, 15%, 20%, 25%, 30%, 35%, 40%, 45%, 50%, 55%, 60%, 65%, 70%, 75%, 80%, 85%, 90%, 95% greater than said one or more reference numbers as having an increased likelihood of responding to said cancer treatment regimen.

Embodiment 37

A method for assessing HRD in a cancer cell or genomic DNA thereof, wherein said method comprises:

(a) detecting, in a cancer cell or genomic DNA derived therefrom, Indicator CA Regions in at least one pair of human chromosomes of said cancer cell, wherein said at least one pair of human chromosomes is not a human X/Y sex chromosome pair; and
(b) determining the total number of Indicator CA Regions in said at least one pair of human chromosomes.

Embodiment 38

A method of predicting the status of BRCA1 and BRCA2 genes in a cancer cell, comprising:
determining, in the cancer cell, the total number of Indicator CA Regions in at least one pair of human chromosomes of said cancer cell; and
diagnosing a patient in whose cancer cell said total number that is greater than a reference number as having an increased likelihood of a deficiency in the BRCA1 or BRCA2 gene.

Embodiment 39

A method of predicting the status of HDR in a cancer cell, comprising:
determining, in the cancer cell, the total number of Indicator CA Regions in at least one pair of human chromosomes of said cancer cell; and
diagnosing a patient in whose cancer cell said total number that is greater than a reference number as having an increased likelihood of a deficiency in HDR.

Embodiment 40

A method of predicting a cancer patient's response to a cancer treatment regimen comprising a DNA damaging agent, an anthracycline, a topoisomerase I inhibitor, radiation, and/or a PARP inhibitor, said method comprising:
determining, in a cancer cell from said cancer patient, the number of Indicator CA Regions in at least one pair of human chromosomes of a cancer cell of said cancer patient; and
diagnosing a patient in whose cancer cell said total number that is greater than a reference number as having an increased likelihood of responding to said cancer treatment regimen.

Embodiment 41

A method of predicting a cancer patient's response to a treatment regimen, comprising:
determining, in a cancer cell from said cancer patient, the total number of Indicator CA Regions in at least one pair of human chromosomes of a cancer cell of said cancer patient; and
diagnosing a patient in whose cancer cell said total number that is greater than a reference number as having an increased likelihood of not responding to a treatment regimen including paclitaxel or docetaxel.

Embodiment 42

A method of treating cancer, comprising:
(a) determining, in a cancer cell from a cancer patient or genomic DNA obtained therefrom, the total number of Indicator CA Regions in at least one pair of human chromosomes of the cancer cell; and
(b) administering to said cancer patient a cancer treatment regimen comprising one or more drugs chosen from the group consisting of DNA damaging agents, anthracyclines, topoisomerase I inhibitors, and PARP inhibitors, if said total number of Indicator CA Regions is greater than a reference number.

Embodiment 43

Use of one or more drugs chosen from the group consisting of DNA damaging agents, anthracyclines, topoisomerase I inhibitors, and PARP inhibitors, for the manufacturing of a medicament useful for treating a cancer in a patient identified as having a cancer cell determined to have a total of 5 or more Indicator CA Regions.

Embodiment 44

A system for determining LOH status of a cancer cell of a cancer patient, comprising:
(a) a sample analyzer configured to produce a plurality of signals about genomic DNA of at least one pair of human chromosomes of said cancer cell, and
(b) a computer sub-system programmed to calculate, based on said plurality of signals, the number of Indicator CA Regions in said at least one pair of human chromosomes.

Embodiment 45

The system of Embodiment 8, wherein said computer sub-system is programmed to compare said number of Indicator CA Regions to a reference number to determine
(a) a likelihood of a deficiency in BRCA1 and/or BRCA2 genes in said cancer cell,
(b) a likelihood of a deficiency in HDR in said cancer cell, or
(c) a likelihood that said cancer patient will respond to cancer treatment regimen comprising a DNA damaging agent, an anthracycline, a topoisomerase I inhibitor, radiation, or a PARP inhibitor.

Embodiment 46

A computer program product embodied in a computer readable medium that, when executing on a computer, performs steps comprising:
detecting the presence or absence of any Indicator CA Region along one or more of human chromosomes; and
determining the total number of said Indicator CA Region in said one or more chromosome pairs.

Embodiment 47

A diagnostic kit comprising:
at least 500 oligonucleotides capable of hybridizing to a plurality of polymorphic regions of human genomic DNA; and
the computer program product of Embodiment 10.

Embodiment 48

Use of a plurality of oligonucleotides capable of hybridizing to a plurality of polymorphic regions of human genomic DNA, for the manufacturing of a diagnostic kit useful for determining the total number of Indicator CA Regions in at least a chromosome pair of a human cancer cell obtained from a cancer patient, and for detecting:
(a) an increased likelihood of a deficiency in the BRCA1 or BRCA2 gene in said cancer cell,
(b) an increased likelihood of a deficiency in HDR in said cancer cell, or
(c) an increased likelihood that said cancer patient will respond to cancer treatment regimen comprising a DNA damaging agent, an anthracycline, a topoisomerase I inhibitor, radiation, or a PARP inhibitor.

Embodiment 49

The method of any one of Embodiments 37-42, wherein said Indicator CA Regions are Indicator LOH Regions, Indicator TAI Regions and Indicator LST Regions and, optionally, are determined in at least two, five, ten or 21 pairs of human chromosomes.

50. The method of any one of Embodiments 36-42, wherein said cancer cell is an ovarian, breast, or esophageal cancer cell.

Embodiment 51

The method of any one of Embodiments 36-42, wherein the total number of are Indicator LOH Regions, Indicator TAI Regions or Indicator LST Regions is 9, 15, 20 or more.

Embodiment 52

The method of any one of Embodiments 36-42, wherein an Indicator LOH Region, Indicator TAI Region or Indicator LST Region is defined as having a length of about 6, 12, or 15 or more megabases.

Embodiment 53

The method of any one of Embodiments 36-42, wherein said reference number is 6, 7, 8, 9, 10, 11, 12 or 13 or greater.

Embodiment 54

The use of Embodiment 43 or 48, wherein said Indicator CA Regions are Indicator LOH Regions, Indicator TAI Regions and Indicator LST Regions and, optionally, are determined in at least two, five, ten or 21 pairs of human chromosomes.

Embodiment 55

The use of Embodiment 43 or 48, wherein said cancer cell is an ovarian, breast, or esophageal cancer cell.

Embodiment 56

The use of Embodiment 43 or 48, wherein the total number of are Indicator LOH Regions, Indicator TAI Regions or Indicator LST Regions is 9, 15, 20 or more.

Embodiment 57

The use of Embodiment 43 or 48, wherein an Indicator LOH Region, Indicator TAI Region or Indicator LST Region is defined as having a length of about 6, 12, or 15 or more megabases.

Embodiment 58

The system of Embodiment 44 or 45, wherein said Indicator CA Regions are Indicator LOH Regions, Indicator TAI Regions and Indicator LST Regions and, optionally, are determined in at least two, five, ten or 21 pairs of human chromosomes.

Embodiment 59

The system of Embodiment 44 or 45, wherein said cancer cell is an ovarian, breast, or esophageal cancer cell.

Embodiment 60

The system of Embodiment 44 or 45, wherein the total number of are Indicator LOH Regions, Indicator TAI Regions or Indicator LST Regions is 9, 15, 20 or more.

Embodiment 61

The system of Embodiment 44 or 45, wherein an Indicator LOH Region, Indicator TAI Region or Indicator LST Region is defined as having a length of about 6, 12, or 15 or more megabases.

Embodiment 62

The computer program product of Embodiment 46, wherein said Indicator CA Regions are Indicator LOH Regions, Indicator TAI Regions and Indicator LST Regions and, optionally, are determined in at least two, five, ten or 21 pairs of human chromosomes.

Embodiment 63

The computer program product of Embodiment 46, wherein said cancer cell is an ovarian, breast, or esophageal cancer cell.

Embodiment 64

The computer program product of Embodiment 46, wherein the total number of are Indicator LOH Regions, Indicator TAI Regions or Indicator LST Regions is 9, 15, 20 or more.

Embodiment 65

The computer program product of Embodiment 46, wherein an Indicator LOH Region, Indicator TAI Region or Indicator LST Region is defined as having a length of about 6, 12, or 15 or more megabases.

Embodiment 66

The method of any one of Embodiments 36-42, wherein said at least one pair of human chromosomes is not human chromosome 17.

Embodiment 67

The use of Embodiment 43 or 48, wherein said Indicator CA Regions are not in human chromosome 17.

Embodiment 68

The system of Embodiment 44 or 45, wherein said Indicator CA Regions are not in human chromosome 17.

Embodiment 69

The computer program product of Embodiment 46, wherein said Indicator CA Regions are not in human chromosome 17.

Embodiment 70

The method of Embodiment 40 or 42, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, or said PARP inhibitor is iniparib, olaparib or velapirib.

Embodiment 71

The use of Embodiment 48, wherein said DNA damaging agent is a platinum-based chemotherapy drug, said anthracycline is epirubincin or doxorubicin, said topoisomerase I inhibitor is campothecin, topotecan, or irinotecan, or said PARP inhibitor is iniparib, olaparib or velapirib.

Embodiment 72

The system of Embodiment 45, wherein said DNA damaging agent is a platinum-based chemotherapy drug, said anthracycline is epirubincin or doxorubicin, said topoisomerase I inhibitor is campothecin, topotecan, or irinotecan, or said PARP inhibitor is iniparib, olaparib or velapirib.

Embodiment 73

The computer program product of Embodiment 46, wherein said DNA damaging agent is a platinum-based chemotherapy drug, said anthracycline is epirubincin or doxorubicin, said topoisomerase I inhibitor is campothecin, topotecan, or irinotecan, or said PARP inhibitor is iniparib, olaparib or velapirib.

Embodiment 74

A method comprising:
(a) detecting, in a cancer cell or genomic DNA derived therefrom, Indicator CA Regions comprising at least two types chosen from Indicator LOH Regions, Indicator TAI Regions or Indicator LST Regions in a representative number of pairs of human chromosomes of the cancer cell; and
(b) determining the number and size of said Indicator CA Regions.

Embodiment 75

The method of Embodiment 74, said representative number of pairs of human chromosomes is representative of the entire genome.

Embodiment 76

The method of Embodiment 74, further comprising correlating an increased number of Indicator CA Regions of a particular size to an increased likelihood of deficiency in HDR.

Embodiment 77

The method of Embodiment 76, wherein said particular size is longer than about 1.5, 2, 2.5, 3, 4, 5, 6, 7, 8, 9, 10, 11, 12, 13, 14, 15, 16, 17, 18, 19, 20, 25, 30, 35, 40, 45, 50, 75, or 100 megabases and less than the length of the entire chromosome that contains the Indicator CA Region.

Embodiment 78

The method of either of Embodiments 76 or 77, wherein 6, 7, 8, 9, 10, 11, 12 or 13 or more Indicator CA Regions of said particular size are correlated to an increased likelihood of deficiency in HDR.

Embodiment 79

A method of determining cancer patient prognosis comprising:
(a) determining whether a sample comprising cancer cells has an HRD signature, wherein the presence of more than a reference number of Indicator CA Regions comprising at least two types chosen from Indicator LOH Regions, Indicator TAI Regions or Indicator LST Regions in at least one pair of human chromosomes of a cancer cell of the cancer patient indicates that the cancer cells have the HRD signature, and
(b)(1) diagnosing a patient in whose sample an HRD signature is detected as having a relatively good prognosis, or
(b)(2) diagnosing a patient in whose sample an HRD signature is not detected as having a relatively poor prognosis 80. A composition comprising a therapeutic agent selected from the group consisting of DNA damaging agent, anthracycline, topoisomerase I inhibitor, and PARP inhibitor for use in treating disease a cancer selected from the group consisting of breast cancer, ovarian cancer, liver cancer, esophageal cancer, lung cancer, head and neck cancer, prostate cancer, colon cancer, rectal cancer, colorectal cancer, and pancreatic cancer in a patient with more than a reference number of Indicator CA Regions in at least one pair of human chromosomes of a cancer cell of the patient.

Embodiment 81

The composition of Embodiment 80, wherein said Indicator CA Regions are determined in at least two, five, ten or 21 pairs of human chromosomes.

Embodiment 82

The composition of Embodiment 80, wherein the total number of said Indicator CA Regions is 9, 15, 20 or more.

Embodiment 83

The composition of Embodiment 80, wherein said first length is about 6, 12, or 15 or more megabases.

Embodiment 84

The composition of Embodiment 80, wherein said reference number is 6, 7, 8, 9, 10, 11, 12 or 13 or greater.

Embodiment 85

A method of treating cancer in a patient, comprising:
determining in a sample from said patient the number of Indicator CA Regions comprising at least two types chosen from Indicator LOH Regions, Indicator TAI Regions or Indicator LST Regions in at least one pair of human chromosomes of a cancer cell of the cancer patient indicates that the cancer cells have the HRD signature;

providing a test value derived from the number of said Indicator CA Regions;

comparing said test value to one or more reference values derived from the number of said Indicator CA Regions in a reference population (e.g., mean, median, terciles, quartiles, quintiles, etc.); and administering to said patient an anti-cancer drug, or recommending or prescribing or initiating a treatment regimen comprising chemotherapy and/or a synthetic lethality agent based at least in part on said comparing step revealing that the test value is greater (e.g., at least 2-, 3-, 4-, 5-, 6-, 7-, 8-, 9-, or 10-fold greater; at least 1, 2, 3, 4, 5, 6, 7, 8, 9, or 10 standard deviations greater) than at least one said reference value; or recommending or prescribing or initiating a treatment regimen not comprising chemotherapy and/or a synthetic lethality agent based at least in part on said comparing step revealing that the test value is not greater (e.g., not more than 2-, 3-, 4-, 5-, 6-, 7-, 8-, 9-, or 10-fold greater; not more than 1, 2, 3, 4, 5, 6, 7, 8, 9, or 10 standard deviations greater) than at least one said reference value.

Embodiment 86

The method of Embodiment 85, wherein said Indicator CA Regions are determined in at least two, five, ten or 21 pairs of human chromosomes.

Embodiment 87

The method of Embodiment 85, wherein the total number of said Indicator CA Regions is 9, 15, 20 or more.

Embodiment 88

The method of Embodiment 85, wherein said first length is about 6, 12, or 15 or more megabases.

Embodiment 89

The method of Embodiment 85, wherein said reference number is 6, 7, 8, 9, 10, 11, 12 or 13 or greater.

Embodiment 90

The method of Embodiment 85, wherein said chemotherapy is selected from the group consisting of a DNA damaging agent, an anthracycline, and a topoisomerase I inhibitor and/or wherein said synthetic lethality agent is a PARP inhibitor drug.

Embodiment 91

The method of Embodiment 85, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, and/or said PARP inhibitor is iniparib, olaparib or velapirib.

Embodiment 92

A method for assessing HRD in a cancer cell or genomic DNA thereof, wherein said method comprises:

(a) detecting, in a cancer cell or genomic DNA derived therefrom, Indicator CA Regions comprising at least two types chosen from Indicator LOH Regions, Indicator TAI Regions or Indicator LST Regions in at least one pair of human chromosomes of said cancer cell, wherein said at least one pair of human chromosomes is not a human X/Y sex chromosome pair; and (b) determining an average (e.g., arithmetic mean) across the total number of Indicator CA Regions by calculating the average of the numbers of Indicator CA Regions of each type detected in said at least one pair of human chromosomes (e.g., if 16 Indicator LOH Regions and 18 Indicator LST Regions, then arithmetic mean is calculated to be 17).

Embodiment 93

A method of predicting the status of BRCA1 and BRCA2 genes in a cancer cell, comprising:

determining, in the cancer cell, an average (e.g., arithmetic mean) across the total number of each type of Indicator CA Regions comprising at least two types chosen from Indicator LOH Regions, Indicator TAI Regions or Indicator LST Regions in at least one pair of human chromosomes of said cancer cell; and correlating said average (e.g., arithmetic mean) across the total number that is greater than a reference number with an increased likelihood of a deficiency in the BRCA1 or BRCA2 gene.

Embodiment 94

A method of predicting the status of HDR in a cancer cell, comprising:

determining, in the cancer cell, an average (e.g., arithmetic mean) across the total number of each type of Indicator CA Regions comprising at least two types chosen from Indicator LOH Regions, Indicator TAI Regions or Indicator LST Regions in at least one pair of human chromosomes of said cancer cell; and correlating said average (e.g., arithmetic mean) across the total number that is greater than a reference number with an increased likelihood of a deficiency in HDR.

Embodiment 95

A method of predicting cancer patient response to a cancer treatment regimen comprising a DNA damaging agent, an anthracycline, a topoisomerase I inhibitor, radiation, and/or a PARP inhibitor, said method comprising:

determining, in a sample comprising a cancer cell, an average (e.g., arithmetic mean) across the total number of each type of Indicator CA Regions comprising at least two types chosen from Indicator LOH Regions, Indicator TAI Regions or Indicator LST Regions in at least one pair of human chromosomes of said sample (e.g., if 16 Indicator LOH Regions and 18 Indicator LST Regions, then arithmetic mean is determined to be 17); and diagnosing a patient in whose sample said average (e.g., arithmetic mean) across the total number is greater than a reference number as having an increased likelihood of responding to said cancer treatment regimen.

Embodiment 96

A method of predicting cancer patient response to a treatment regimen, comprising:

determining, in a patient sample comprising a cancer cell, an average (e.g., arithmetic mean) across the total number of Indicator CA Regions comprising at least two types chosen from Indicator LOH Regions, Indicator TAI Regions or Indicator LST Regions in at least one pair of human chromosomes of said patient sample; and diagnosing a patient in whose sample said average (e.g., arithmetic mean) across the total number is greater than a reference number as having an increased likelihood of not responding to a treatment regimen including paclitaxel or docetaxel.

Embodiment 97

A method of treating cancer, comprising:
(a) determining, in a patient sample comprising a cancer cell or genomic DNA obtained therefrom, an average (e.g., arithmetic mean) across the total number of each type of Indicator CA Regions comprising at least two types chosen from Indicator LOH Regions, Indicator TAI Regions or Indicator LST Regions in at least one pair of human chromosomes of the cancer cell; and
(b) administering to a patient in whose sample said total number of Indicator CA Regions is greater than a reference number a cancer treatment regimen comprising one or more drugs chosen from the group consisting of DNA damaging agents, anthracyclines, topoisomerase I inhibitors, and PARP inhibitors.

Embodiment 98

The method of Embodiment 95 or 97, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, or said PARP inhibitor is iniparib, olaparib or velapirib.

Embodiment 99

A composition comprising a therapeutic agent selected from the group consisting of DNA damaging agent, anthracycline, topoisomerase I inhibitor, and PARP inhibitor for use in treating disease a cancer selected from the group consisting of breast cancer, ovarian cancer, liver cancer, esophageal cancer, lung cancer, head and neck cancer, prostate cancer, colon cancer, rectal cancer, colorectal cancer, and pancreatic cancer in a patient with more than a reference number of an average (e.g., arithmetic mean) across the types of Indicator CA Regions comprising at least two types chosen from Indicator LOH Regions, Indicator TAI Regions or Indicator LST Regions in at least one pair of human chromosomes of a cancer cell of the patient.

Embodiment 100

A method of treating cancer in a patient, comprising:
determining in a sample from said patient an average (e.g., arithmetic mean) of the total number of Indicator CA Regions in at least one pair of human chromosomes of a cancer cell of the cancer patient indicates that the cancer cells have the HRD signature;
providing a test value derived from the average (e.g., arithmetic mean) across the numbers of each type of said Indicator CA Regions comprising at least two types chosen from Indicator LOH Regions, Indicator TAI Regions or Indicator LST Regions;
comparing said test value to one or more reference values derived from the number of said average (e.g., arithmetic mean) across the types of Indicator CA Regions in a reference population (e.g., mean, median, terciles, quartiles, quintiles, etc.); and
administering to said patient an anti-cancer drug, or recommending or prescribing or initiating a treatment regimen comprising chemotherapy and/or a synthetic lethality agent based at least in part on said comparing step revealing that the test value is greater (e.g., at least 2-, 3-, 4-, 5-, 6-, 7-, 8-, 9-, or 10-fold greater; at least 1, 2, 3, 4, 5, 6, 7, 8, 9, or 10 standard deviations greater) than at least one said reference value; or
recommending or prescribing or initiating a treatment regimen not comprising chemotherapy and/or a synthetic lethality agent based at least in part on said comparing step revealing that the test value is not greater (e.g., not more than 2-, 3-, 4-, 5-, 6-, 7-, 8-, 9-, or 10-fold greater; not more than 1, 2, 3, 4, 5, 6, 7, 8, 9, or 10 standard deviations greater) than at least one said reference value.

Embodiment 101

The method of Embodiment 100, wherein said average (e.g., arithmetic mean) across the types of Indicator CA Regions are determined in at least two, five, ten or 21 pairs of human chromosomes.

Embodiment 102

The method of Embodiment 100, wherein said chemotherapy is selected from the group consisting of a DNA damaging agent, an anthracycline, and a topoisomerase I inhibitor and/or wherein said synthetic lethality agent is a PARP inhibitor drug.

Embodiment 103

The method of Embodiment 100, wherein said DNA damaging agent is cisplatin, carboplatin, oxalaplatin, or picoplatin, said anthracycline is epirubincin or doxorubicin, said topoisomerase I inhibitor is campothecin, topotecan, or irinotecan, and/or said PARP inhibitor is iniparib, olaparib or velapirib.

Embodiment 104

The method of Embodiment 1, wherein said Indicator CA Regions are the combination of Indicator LOH Regions, Indicator TAI Regions and Indicator LST Regions.

Embodiment 105

The method of Embodiment 104, wherein said reference number is 42.

Embodiment 106

The method of Embodiment 9, wherein said Indicator CA Regions are the combination of Indicator LOH Regions, Indicator TAI Regions and Indicator LST Regions.

Embodiment 107

The method of Embodiment 106, wherein said reference number is 42.

Embodiment 108

The method of Embodiment 18, wherein said Indicator CA Regions are the combination of Indicator LOH Regions, Indicator TAI Regions and Indicator LST Regions.

Embodiment 109

The method of Embodiment 108, wherein said reference number is 42.

Embodiment 110

The method of Embodiment 28, wherein said reference number is 42.

Embodiment 111

The method of Embodiment 37, wherein said Indicator CA Regions are the combination of Indicator LOH Regions, Indicator TAI Regions and Indicator LST Regions.

Embodiment 112

The method of Embodiment 111, wherein said reference number is 42.

Embodiment 113

The method of Embodiment 38, wherein said Indicator CA Regions are the combination of Indicator LOH Regions, Indicator TAI Regions and Indicator LST Regions.

Embodiment 114

The method of Embodiment 113, wherein said reference number is 42.

Embodiment 115

The method of Embodiment 39, wherein said Indicator CA Regions are the combination of Indicator LOH Regions, Indicator TAI Regions and Indicator LST Regions.

Embodiment 116

The method of Embodiment 115, wherein said reference number is 42.

Embodiment 117

The method of Embodiment 40, wherein said Indicator CA Regions are the combination of Indicator LOH Regions, Indicator TAI Regions and Indicator LST Regions.

Embodiment 118

The method of Embodiment 117, wherein said reference number is 42.

Embodiment 119

The method of Embodiment 41, wherein said Indicator CA Regions are the combination of Indicator LOH Regions, Indicator TAI Regions and Indicator LST Regions.

Embodiment 120

The method of Embodiment 119, wherein said reference number is 42.

Embodiment 121

The method of Embodiment 42, wherein said Indicator CA Regions are the combination of Indicator LOH Regions, Indicator TAI Regions and Indicator LST Regions.

Embodiment 122

The method of Embodiment 121, wherein said reference number is 42.

Embodiment 123

The method of Embodiment 79, wherein said Indicator CA Regions are the combination of Indicator LOH Regions, Indicator TAI Regions and Indicator LST Regions.

Embodiment 124

The method of Embodiment 123, wherein said reference number is 42.

Embodiment 125

The method of Embodiment 85, wherein said Indicator CA Regions are the combination of Indicator LOH Regions, Indicator TAI Regions and Indicator LST Regions.

Embodiment 126

The method of Embodiment 125, wherein said reference number is 42.

Embodiment 127

An in vitro method of predicting patient response to a cancer treatment regimen comprising a DNA damaging agent, anthracycline, topoisomerase I inhibitor, or PARP inhibitor, the method comprising:
  (1) determining, in a sample comprising a cancer cell, the number of Indicator CA Regions comprising Indicator LOH Regions, Indicator TAI Regions, and Indicator LST Regions in at least one pair of human chromosomes of a cancer cell of said cancer patient;
  (2) combining said Indicator CA Regions to provide a test value as follows: Test Value=(number of Indicator LOH Regions)+(number of Indicator TAI Regions)+(number of Indicator LST Regions); and
  (3) providing a reference value for comparison against said test value.

Embodiment 128

The method of Embodiment 127, wherein said reference value represents the $5^{th}$ percentile of Indicator CA Region scores in a training cohort of HDR deficient patients.

Embodiment 129

The method of Embodiment 127 or Embodiment 128, wherein said reference value is 42.

Embodiment 130

The method of any one of Embodiments 127 to 129, further comprising comparing said test value to said reference value.

Embodiment 131

The method of any one of Embodiments 127 to 130, further comprising diagnosing a patient in whose sample said test value is greater than said reference value as having an increased likelihood of responding to said cancer treatment regimen.

Embodiment 132

The method of any one of Embodiments 127 to 131, wherein said determining step comprises assaying said sample to measure the copy number of each allele for at least 150, 200, 250, 300, 350, 400, 450, 500, 600, 700, 800, 900, 1,000, 1,500, 2,000, 2,500, 3,000, 3,500, 4,000, 4,500, 5,000, 6,000, 7,000, 8,000, 9,000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000 80,000, 90,000, 100,000, 125,000, 150,000, 175,000, 200,000, 250,000, 300,000, 400,000, 500,000, 600,000, 700,000, 800,000, 900,000, 1,000,000 or more polymorphic genomic loci in at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 autosome pairs.

Embodiment 133

The method of Embodiment 132, wherein said determining step comprises assaying said polymorphic genomic loci in at least 10 autosome pairs.

Embodiment 134

The method of Embodiment 133, wherein said polymorphic genomic loci in 22 autosome pairs.

Embodiment 135

The method of any one of Embodiments 132 to 134, wherein said determining step comprises assaying said sample to measure the copy number of each allele for at least 5,000 polymorphic genomic loci in said autosome pairs.

Embodiment 136

The method of Embodiment 135, wherein said determining step comprises assaying said sample to measure the copy number of each allele for at least 10,000 polymorphic genomic loci in said autosome pairs.

Embodiment 137

The method of Embodiment 136, wherein said determining step comprises assaying said sample to measure the copy number of each allele for at least 50,000 polymorphic genomic loci in said autosome pairs.

The invention will be further described in the following examples, which do not limit the scope of the invention described in the claims.

EXAMPLES

Example 1—LOH and TAI Region Scores Across Breast Cancer Subtypes and Association with BRCA1/2 Deficiency An LOH signature based on whole genome tumor LOH profiles has been developed that is highly correlated with defects in BRCA1/2 and other HDR pathway genes in ovarian cancer (Abkevich, et al., *Patterns of Genomic Loss of Heterozygosity Predict Homologous Recombination Repair Defects*, BR. J. CANCER (2012)), and which predicts response to DNA-damaging agent (e.g., platinum-based neoadjuvant) therapy in breast cancer (Telli et al., *Homologous Recombination Deficiency (HRD) score predicts response following neoadjuvant platinum-based therapy in triple-negative and BRCA1/2 mutation-associated breast cancer (BC)*, CANCER RES. (2012)). A second score based on TAI score also shows strong correlation with BRCA1/2 defects and predicts response to platinum treatment in triple negative breast cancer (Birkbak et al., *Telomeric allelic imbalance indicates defective DNA repair and sensitivity to DNA-damaging agents*, CANCER DISCOV. (2012)). This study examined the frequency of BRCA1/2 defects and elevated LOH or TAI Region Score across breast cancer subtypes as defined by ER/PR/HER2 status.

Frozen tumors were purchased from 3 commercial tissue biobanks. Approximately 50 randomly ascertained tumors from each of 4 breast cancer subtypes (triple negative, ER+/HER2−, ER−/HER2+, ER+/HER2+) were selected for analysis. A targeted custom hybridization panel was developed targeting BRCA1, BRCA2, and 50,000 selected SNPs across the complete genome. This panel, in combination with sequencing on the Illumina HiSeq2500, was used to analyze the tumors for BRCA1/2 somatic and germline mutations, including large rearrangements, and SNP allele dosages. BRCA1 promoter methylation was determined by a qPCR assay (SA Biosciences). When available, DNA from normal tissue was used to determine whether deleterious mutations were germline or somatic.

SNP data was analyzed using an algorithm that determines the most likely allele specific copy number at each SNP location. The LOH Region Score was calculated by counting the number of LOH regions that are >15 Mb in length, but shorter than the length of a complete chromosome. The TAI Region Score was calculated by counting the number of telomeric regions with allelic imbalance that are >11 Mb in length, but do not cross the centromere. Samples with low quality SNP data and/or with high contamination with normal DNA were excluded. 191 out of 213 samples yielded robust scores.

TABLE 2

BRCA1/2 deficiency in breast cancer IHC subtypes.

| Subtype | n | BRCA1 Mutations | BRCA2 Mutations | Total Mutants (%) | BRCA1 Promoter Methylation (%) |
|---|---|---|---|---|---|
| Triple Negative | 61 | 10 | 3 | 10 (16.4) | 12 (19.7) |
| ER+/HER2− | 51 | 2 | 2 | 4 (7.8) | 1 (1.9) |
| ER−/HER2+ | 38 | 3 | 1 | 4 (10.5) | 0 |
| ER+/HER2+ | 63 | 8 | 1 | 7 (11.1) | 1 (1.6) |

TABLE 3

Mutation screening was performed on matched normal tissue from 17 of the BRCA1/2 mutants. 13 of the 17 individuals (76.5%) had a germline mutation.

| Subtype | Tumor Mutation Profile | n | Germline | Somatic |
|---|---|---|---|---|
| Triple Negative | 1 BRCA1 mutation | 3 | 2 | 1 |
| | 1 BRCA2 mutation | 1 | 1 | 0 |
| | 2 BRCA1 mutations | 1 | 1 | 1 |
| | 1 BRCA1 mutation & 2 BRCA2 mutations | 1 | 1 (BRCA2) | 2 |
| ER+/HER2− | 1 BRCA1 mutation | 1 | 1 | 0 |
| | 1 BRCA2 mutation | 2 | 2 | 0 |
| ER−/HER2+ | 1 BRCA1 mutation | 2 | 1 | 1 |
| ER+/HER2+ | 1 BRCA1 mutation | 3 | 1 | 2 |
| | 2 BRCA1 mutations | 2* | 2 | 2 |
| | 1 BRCA2 mutation | 1 | 1 | 0 |

*Each individual had 1 germline and 1 somatic mutation in BRCA1.

TABLE 4

Association between LOH or TAI score and BRCA1/2 deficiency

| | | Mean LOH Score | | | Mean TAI Score | | |
|---|---|---|---|---|---|---|---|
| Subtype | n (BRCA1/2 Deficient) | BRCA1/2 Intact | BRCA1/2 Deficient | p value | BRCA1/2 Intact | BRCA1/2 Deficient | p value |
| All | 191 (38) | 8.1 | 16.5 | $8*10^{-12}$ | 5.7 | 13.9 | $2*10^{-16}$ |
| Triple Negative | 53 (22) | 8.3 | 18.1 | $6*10^{-6}$ | 6.7 | 13.2 | $3*10^{-6}$ |
| ER+/HER2+ | 56 (8) | 7.4 | 13.6 | 0.0009 | 5 | 15.6 | $10^{-6}$ |
| ER+/HER2− | 47 (5) | 7.7 | 15 | 0.01 | 5 | 16 | 0.0009 |
| ER−/HER2+ | 34 (3) | 9.5 | 15.3 | 0.03 | 6.6 | 11.3 | NS |

Figure 5A:
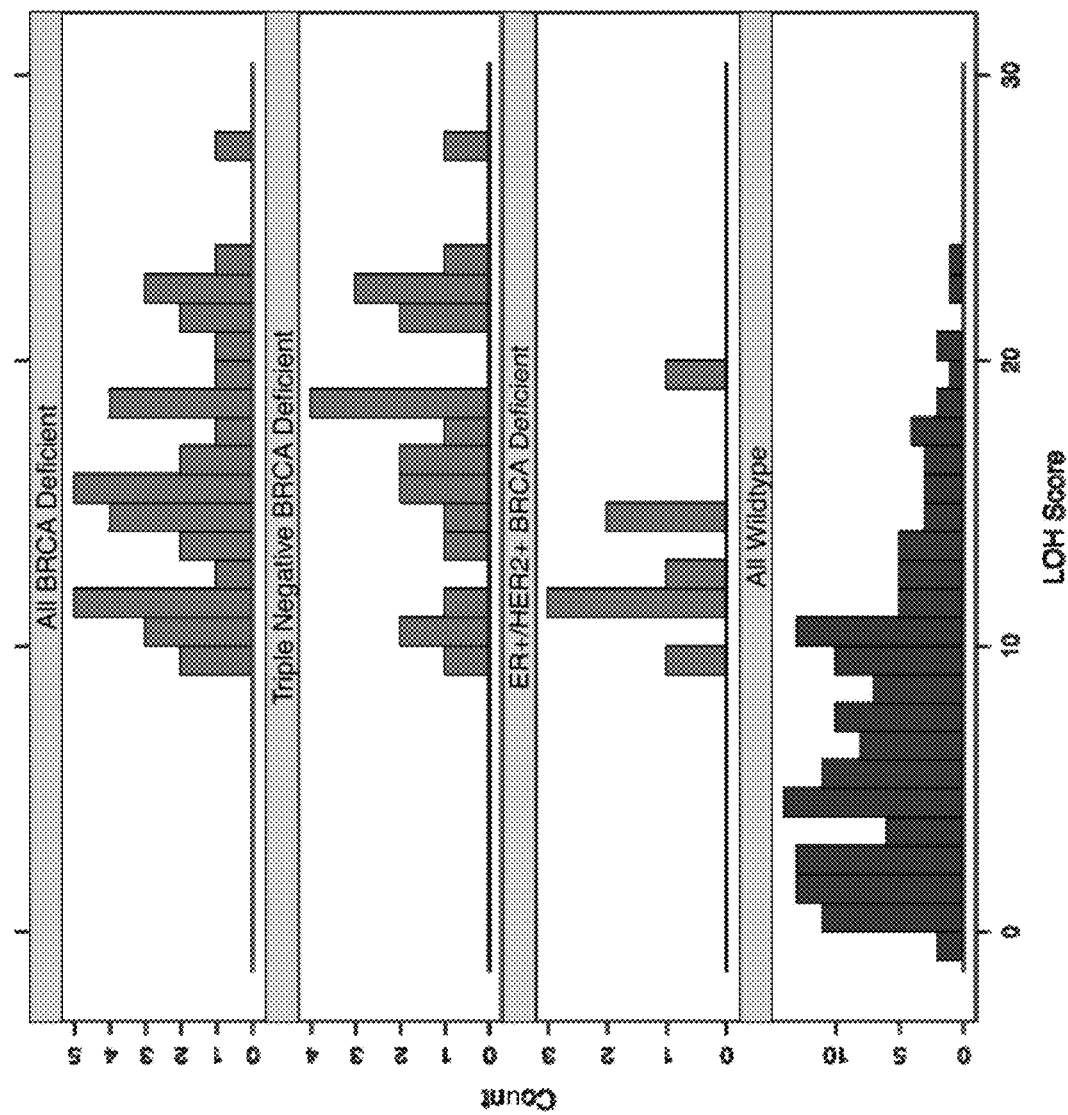
FIG. 5A shows LOH Regions Scores across breast cancer IHC subtypes. The top three panels are BRCA1/2 deficient samples. The bottom panel is BRCA1/2 intact samples.
Figure 5B:
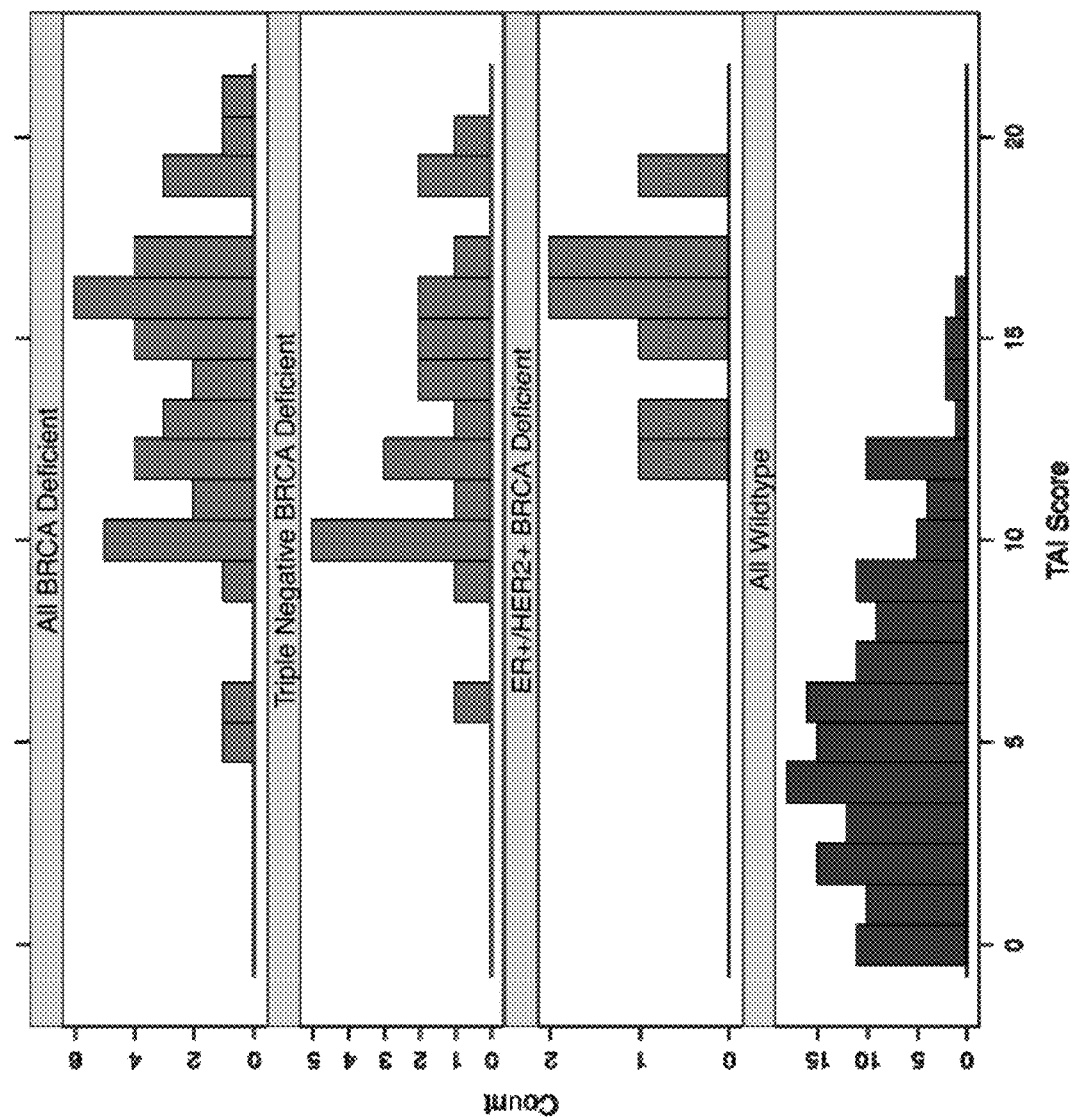
FIG. 5B shows TAI Regions Scores across breast cancer IHC subtypes. The top three panels are BRCA1/2 deficient samples. The bottom panel is BRCA1/2 intact samples.
Figure 6:
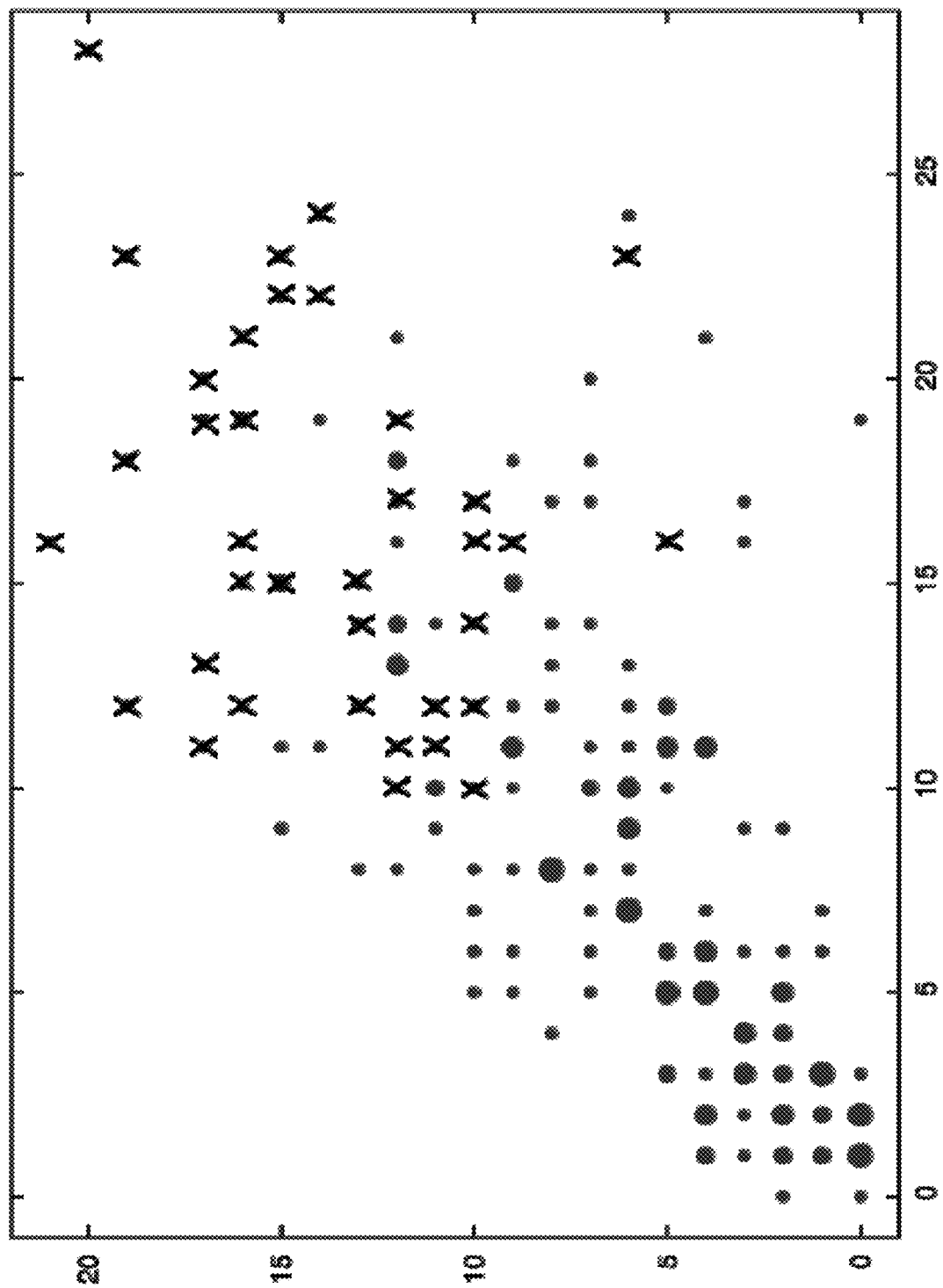
FIG. 6 shows the correlation between LOH and TAI Region Scores. Correlation coefficient=0.69. X axis: LOH score; Y axis: TAI score; red dots: intact samples; blue dots (with a super imposed "X"): BRCA1/2 deficient samples. The area under the dots is proportional to the number of samples with that combination of LOH and TAI scores. $p=10^{-39}$.

FIG. 5 shows LOH and TAI Region Scores across breast cancer IHC subtypes. 5A: LOH score; 5B: TAI score. Blue bars: BRCA1/2 deficient samples. Red bars: BRCA1/2 intact samples. FIG. 6 shows the correlation between LOH and TAI Region Scores (Correlation coefficient=0.69). X axis: LOH score; Y axis: TAI score; red dots: intact samples; blue dots: BRCA1/2 deficient samples. The area under the dots is proportional to the number of samples with that combination of LOH and TAI scores ($p=10^{-39}$).

Logistic regression analysis was used to predict BRCA1/2 deficiency based on LOH and TAI scores. Both scores were significant in a multivariate analysis (Chi Square for LOH is 10.8, and for TAI is 44.7; p=0.001 and $2.3*10^{-11}$). The best model for differentiation between BRCA1/2 deficient and intact samples is 0.32*LOH Region Score+0.68*TAI Region Score ($p=9*10^{-18}$).

Conclusions

Elevated LOH and TAI Region Scores are each highly associated with BRCA1/2 deficiency in all subtypes of breast cancer; LOH and TAI Region Scores are highly significantly correlated; a Combined CA Region Score (i.e., combining LOH and TAI) shows the optimal correlation with BRCA1/2 deficiency in this dataset. The combination of LOH-HRD and TAI-HRD scores can, based on the present disclosure, predict response to DNA-damaging and other agents (e.g., platinum therapy) in triple negative breast cancer, and enable expansion of platinum use to other breast cancer subtypes.

Example 2—LOH, TAI, and LST Region Scores Across Breast Cancer Subtypes and Association with BRCA1/2 Deficiency SNP allele frequency ratios were obtained and were used to calculate LOH, TAI and LST Region Scores as described in Example 1. LST score was defined as the number of breakpoints between regions longer than 10 megabases having stable copy number after filtering out regions shorter than 3 megabases. We observed that LST score increased with ploidy both within intact and deficient samples. Instead of using ploidy-specific cutoffs in this Example 2, therefore, we modified LST Region Score by adjusting it by ploidy: LSTm=LST−kP, where P is ploidy and k is a constant. Based on multivariate logistic regression analysis with deficiency as an outcome and LST and P as predictors, k=15.5.

Figure 7A:
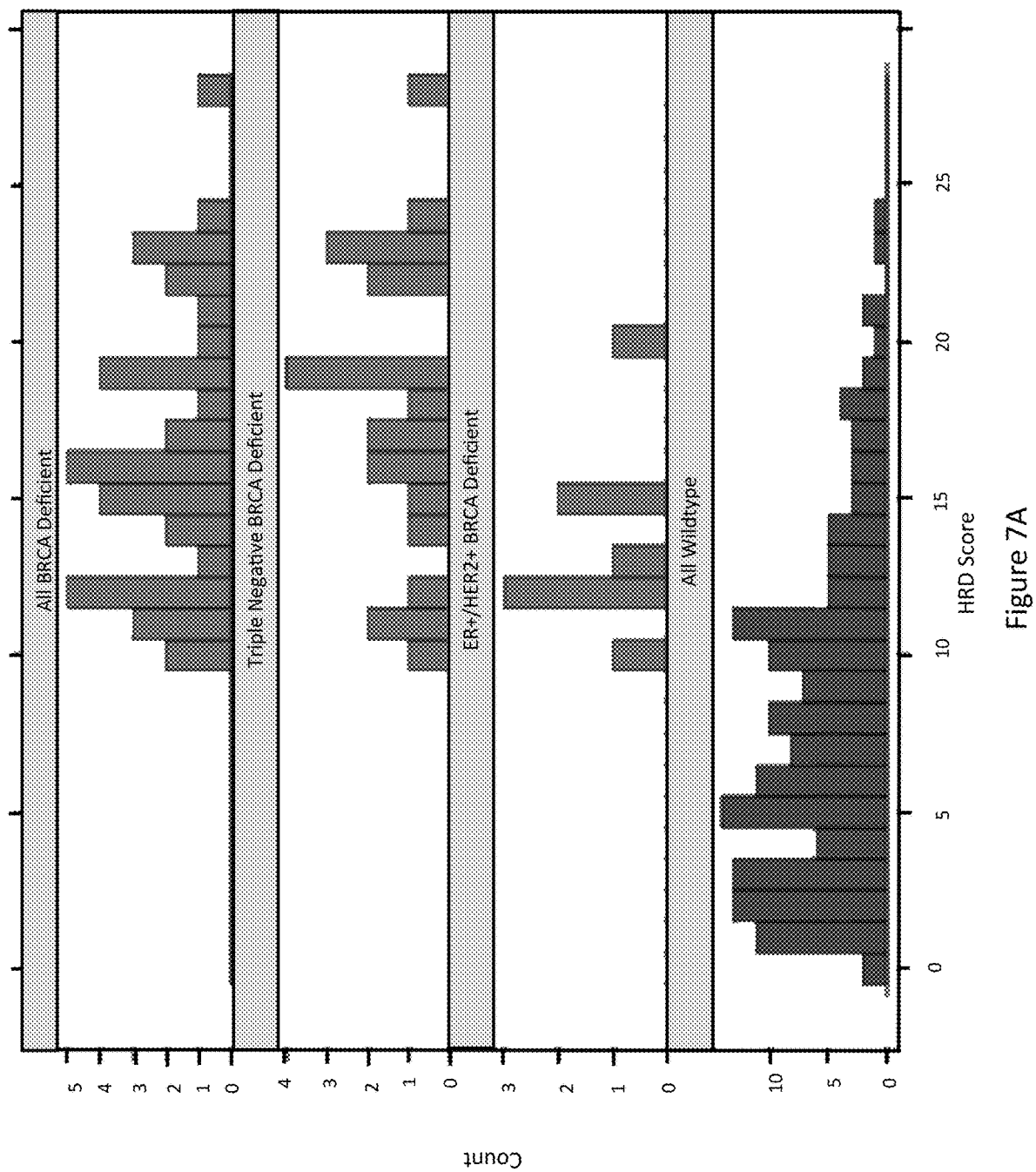
FIG. 7A shows LOH Region Scores for patients as analyzed in Example 2 herein. The top three panels are BRCA1/2 deficient samples. The bottom panel is BRCA1/2 intact samples.
Figure 7B:
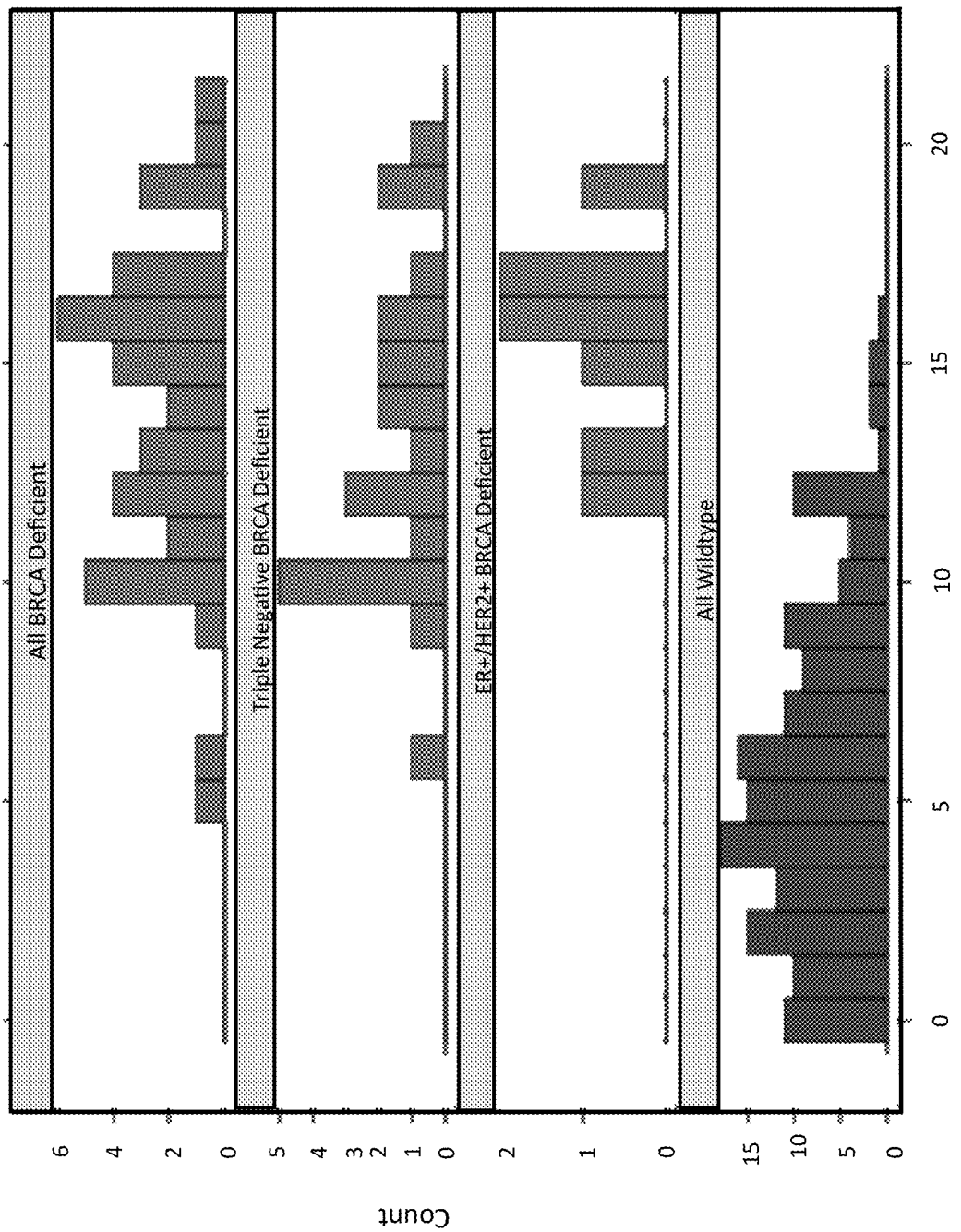
FIG. 7B shows TAI Region Scores for patients as analyzed in Example 2 herein. The top three panels are BRCA1/2 deficient samples. The bottom panel is BRCA1/2 intact samples.
Figure 7C:
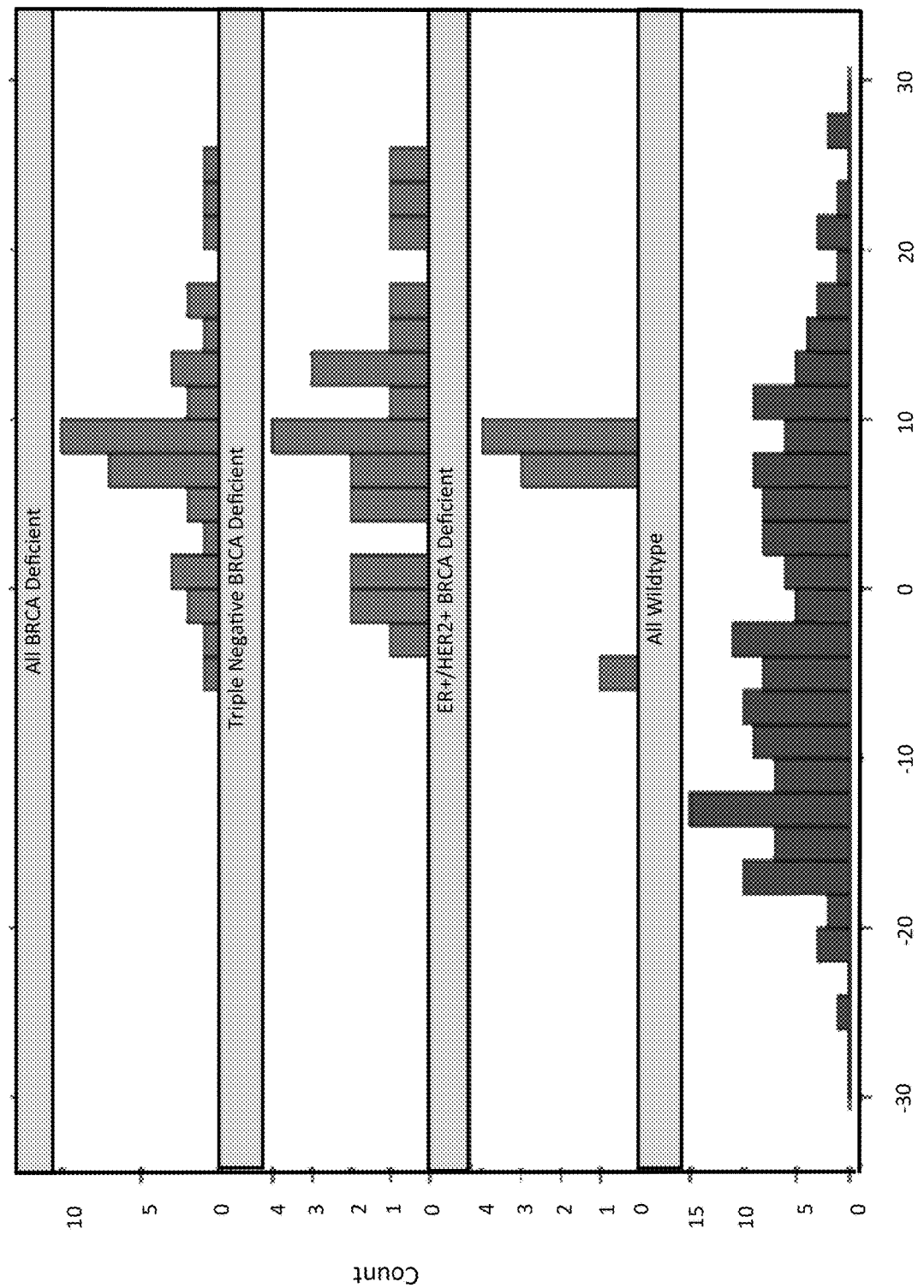
FIG. 7C shows LST Regions Scores for patients as analyzed in Example 2 herein. The top three panels are BRCA1/2 deficient samples. The bottom panel is BRCA1/2 intact samples.
Figure 7D:
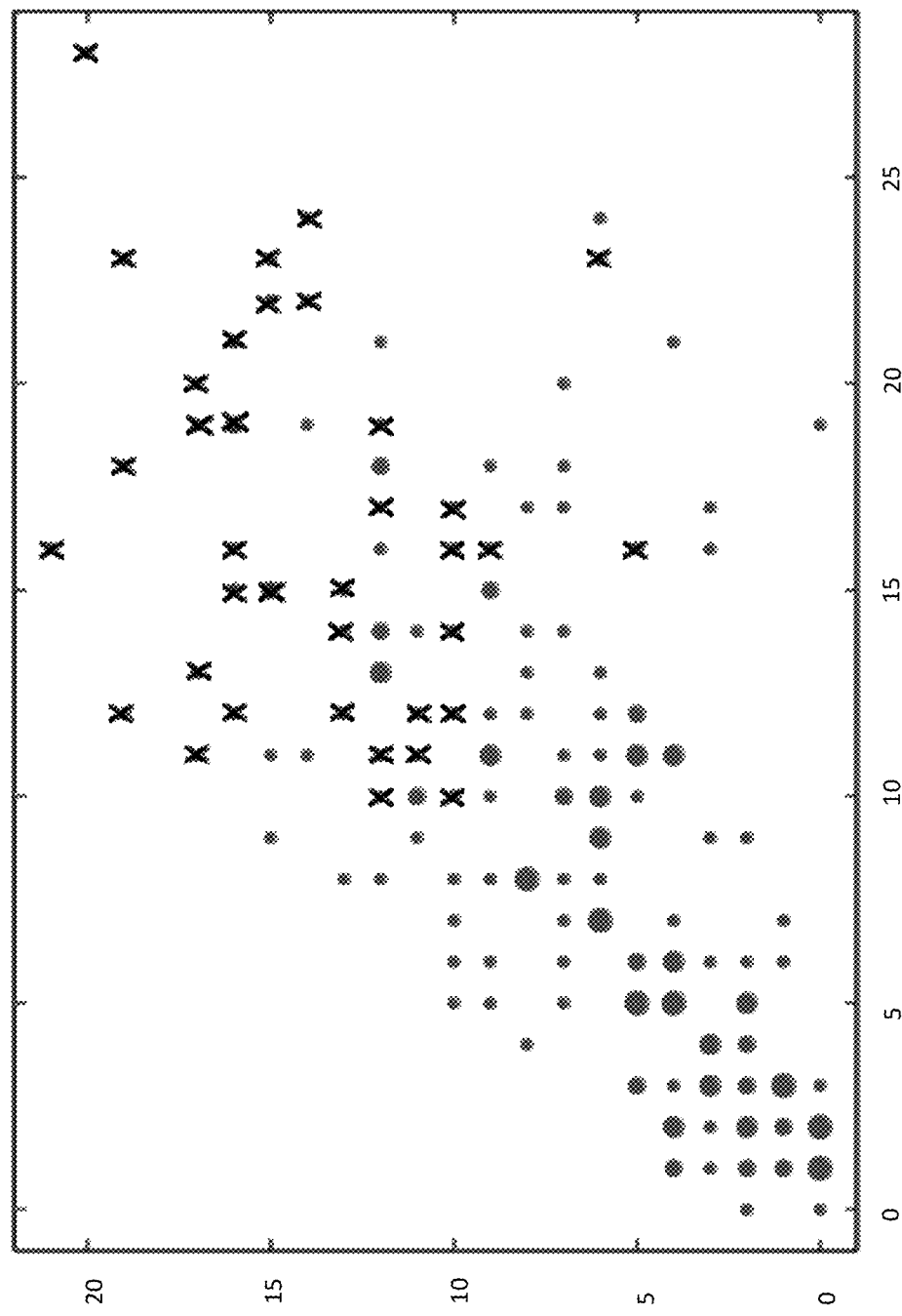
FIG. 7D shows LOH vs TAI for patients as analyzed in Example 2 herein. X axis: LOH score; Y axis: TAI score; red dots: intact samples; blue dots (with a super imposed "X"): BRCA1/2 deficient samples. The area under the dots is proportional to the number of samples with that combination of LOH and TAI scores.
Figure 7E:
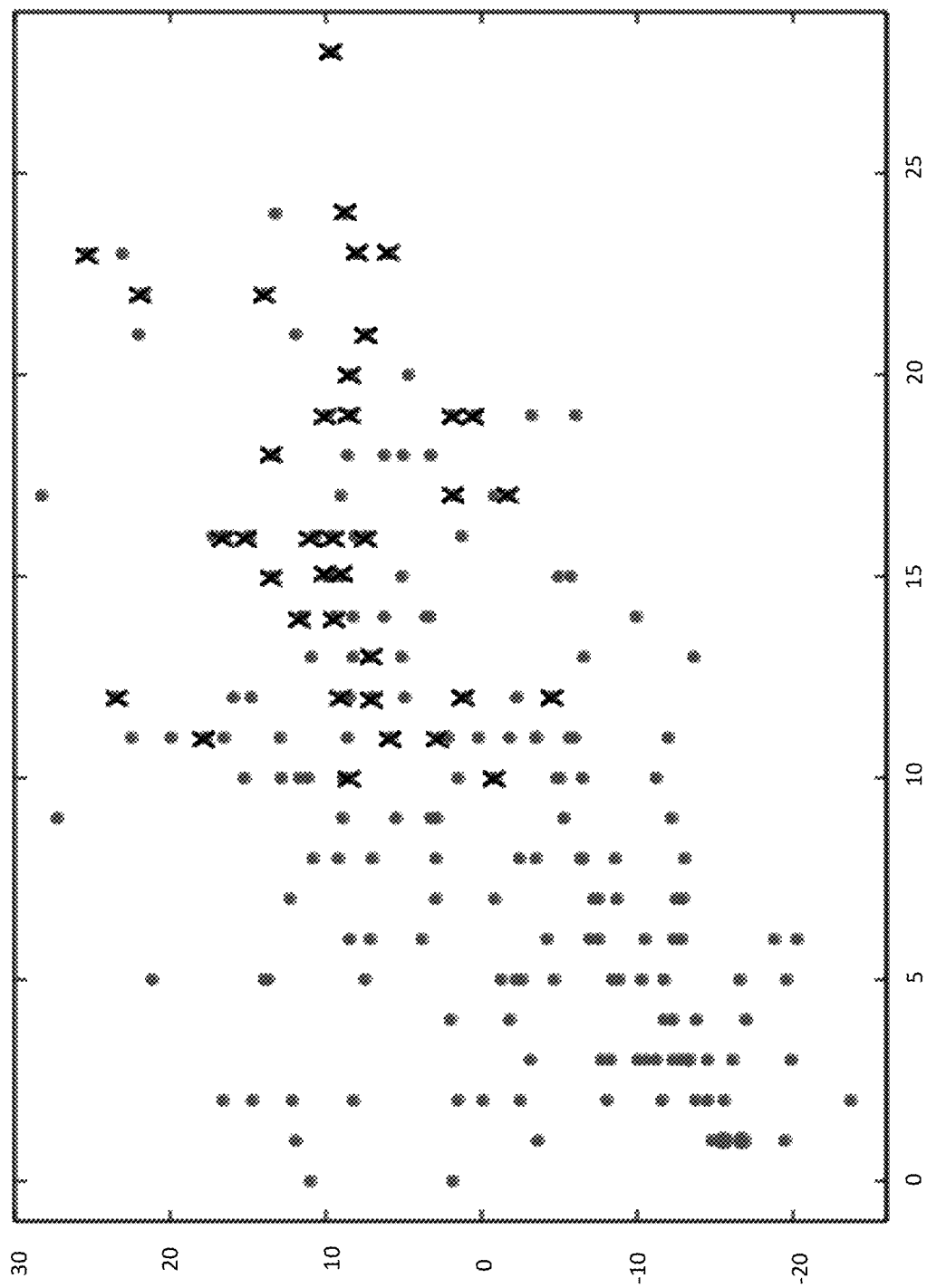
FIG. 7E shows LOH vs LST for patients as analyzed in Example 2 herein. X axis: LOH score; Y axis: LST score; red dots: intact samples; blue dots (with a super imposed "X"): BRCA1/2 deficient samples. The area under the dots is proportional to the number of samples with that combination of LOH and LST scores.

191 of 214 samples gave scores that passed the QC criteria used. 38 of these samples were BRCA1/2 deficient. The corresponding p-values according to Kolmogorov-Smirnov test for LOH Region Score is $8*10^{-12}$, for TAI Region Score is $2*10^{-16}$, and for LST Region Score is $8*10^{-8}$. 53/191 samples were triple negative breast cancer, including 22 that were BRCA1/2 deficient. Corresponding p-values were $6*10^{-6}$, $3*10^{-6}$, and 0.0002 for LOH, TAI, and LST Region Scores respectively. When the same analysis is performed for each individual breast cancer subtype significant p-values are also seen for all subtypes with at least one of the scores (Table 5). The distribution of scores is shown for BRCA1/2 deficient vs. BRCA1/2 intact samples in FIG. 7A-C.

The scores were next analyzed to determine whether they were correlated (FIG. 2D-F). The correlation coefficient between LOH Region Score and TAI Region Score was 0.69 ($p=10^{-39}$), between LOH and LST was 0.55 ($p=2*10^{-19}$), and between TAI and LST was 0.39 ($p=10^{-9}$).

Logistic regression analysis was used to predict BRCA1/2 deficiency based on LOH, TAI, and LST Region Scores. All three scores were significant in a multivariate analysis (Chi Square for LOH is 5.1 (p=0.02), for TAI is 44.7 ($p=2*10^{-11}$), and for LST is 5.4 (p=0.02)). The best model for differentiation between BRCA1/2 deficient and intact samples in this dataset was 0.21*LOH+0.67*TAI+0.12*LST (p=10−

18). This Example 2 extends the conclusions from Example 1 (i.e., a model combining LOH and TAI Region Scores) to a model combining LOH, TAI, and LST Region Scores.

Other clinical data that were available for many of the samples included stage, grade, and age of diagnosis. Stage information was available for 64/191 samples. The correlation coefficient between stage and LOH Region Score (0.07) and TAI Region Score (0.1) were not significant. Grade information was available for 164/191 samples. The correlation coefficient between grade and LOH Region Score (0.33) and TAI Region Score (0.23) are significant ($p=2*10^{-5}$ and 0.004 respectively). Age of diagnosis was known for 184/191 samples. The correlation coefficient between age and LOH Region Score (−0.13) was not significant. The correlation coefficient between age and TAI Region Score (−0.25) was significant (p=0.0009).

TABLE 5

| Subtype | n (BRCA1/2 Deficient) | Mean Score BRCA1/2 Intact | Mean Score BRCA1/2 Deficient | p value |
|---|---|---|---|---|
| LOH Region Score | | | | |
| All | 191 (38) | 8.1 | 16.5 | $8*10^{-12}$ |
| Triple Negative | 53 (22) | 8.3 | 18.1 | $6*10^{-6}$ |
| ER+/HER2− | 47 (5) | 7.7 | 15 | 0.01 |
| ER−/HER2+ | 34 (3) | 9.5 | 15.3 | 0.03 |
| ER+/HER2+ | 56 (8) | 7.4 | 13.6 | $9*10^{-4}$ |
| TAI Region Score | | | | |
| All | 191 (38) | 5.7 | 13.9 | $2*10^{-16}$ |
| Triple Negative | 53 (22) | 6.7 | 13.2 | $3*10^{-6}$ |
| ER+/HER2− | 47 (5) | 5 | 16 | $9*10^{-4}$ |
| ER−/HER2+ | 34 (3) | 6.6 | 11.3 | NS |
| ER+/HER2+ | 56 (8) | 5 | 15.6 | $10^{-6}$ |
| LST Region Score | | | | |
| All | 191 (38) | 9.01 | −1.3 | $8*10^{-8}$ |
| Triple Negative | 53 (22) | 10.14 | −1.41 | 0.0002 |
| ER+/HER2− | 47 (5) | 7.31 | 1.54 | NS |
| ER−/HER2+ | 34 (3) | 9.18 | −2.19 | 0.02 |
| ER+/HER2+ | 56 (8) | 7.31 | 1.54 | NS |

Example 3—Arithmetic Mean of LOH, TAI, and LST Region Scores Across Breast Cancer Subtypes and Association with BRCA1/2 Deficiency The following study shows how HRD scores as described herein can predict BRCA1/2 deficiency and the efficacy of agents targeting HR deficiency in triple negative breast cancer (TNBC). To investigate the rate of BRCA1/2 deficiency across breast cancer subtypes, breast tumor samples were assayed for BRCA1/2 mutations and promoter methylation. The three HRD scores as described in Example 2 were determined for the samples, and the association with BRCA1/2 deficiency was then examined using an arithmetic mean of the LOH/TAI/LST scores. Analysis of a neoadjuvant TNBC cohort treated with cisplatin was further examined relative to the relationship between all three HRD scores and response.

Invasive breast tumor samples and matched normal tissue were obtained from three commercial vendors. The samples were selected to give approximately equal numbers of all subtypes of breast cancer as defined by IHC analysis of ER, PR, and HER2. BRCA1 promoter methylation analysis was performed by qPCR. BRCA1/2 mutation screening and genome wide SNP profiles were generated using a custom Agilent SureSelect XT capture followed by sequencing on Illumina HiSeq2500. These data were used to calculate HRD-LOH, HRD-TAI, and HRD-LST scores.

SNP microarray data and clinical data were downloaded from a public repository for the cisplatin-1 and cisplatin-2 trial cohorts. BRCA1/2 mutation data was not available for one of these cohorts. All three HRD scores were calculated using publically available data, and analyzed for association with response to cisplatin. The two cohorts were combined to improve power.

To calculate HRD scores the SNP data was analyzed using an algorithm that determines the most likely allele specific copy number at each SNP location. HRD-LOH was calculated by counting the number of LOH regions >15 Mb in length, but shorter than the length of a complete chromosome. HRD-TAI score was calculated by counting the number of regions >11 Mb in length with allelic imbalance that extend to one of the subtelomeres, but do not cross the centromere. HRD-LST score was the number of break points between regions longer than 10 Mb after filtering out regions shorter than 3 Mb.

The combined score was the arithmetic mean of the LOH/TAI/LST scores. All p values were from logistic regression models with BRCA deficiency or response to cisplatin as the dependent variable.

Figure 9A:
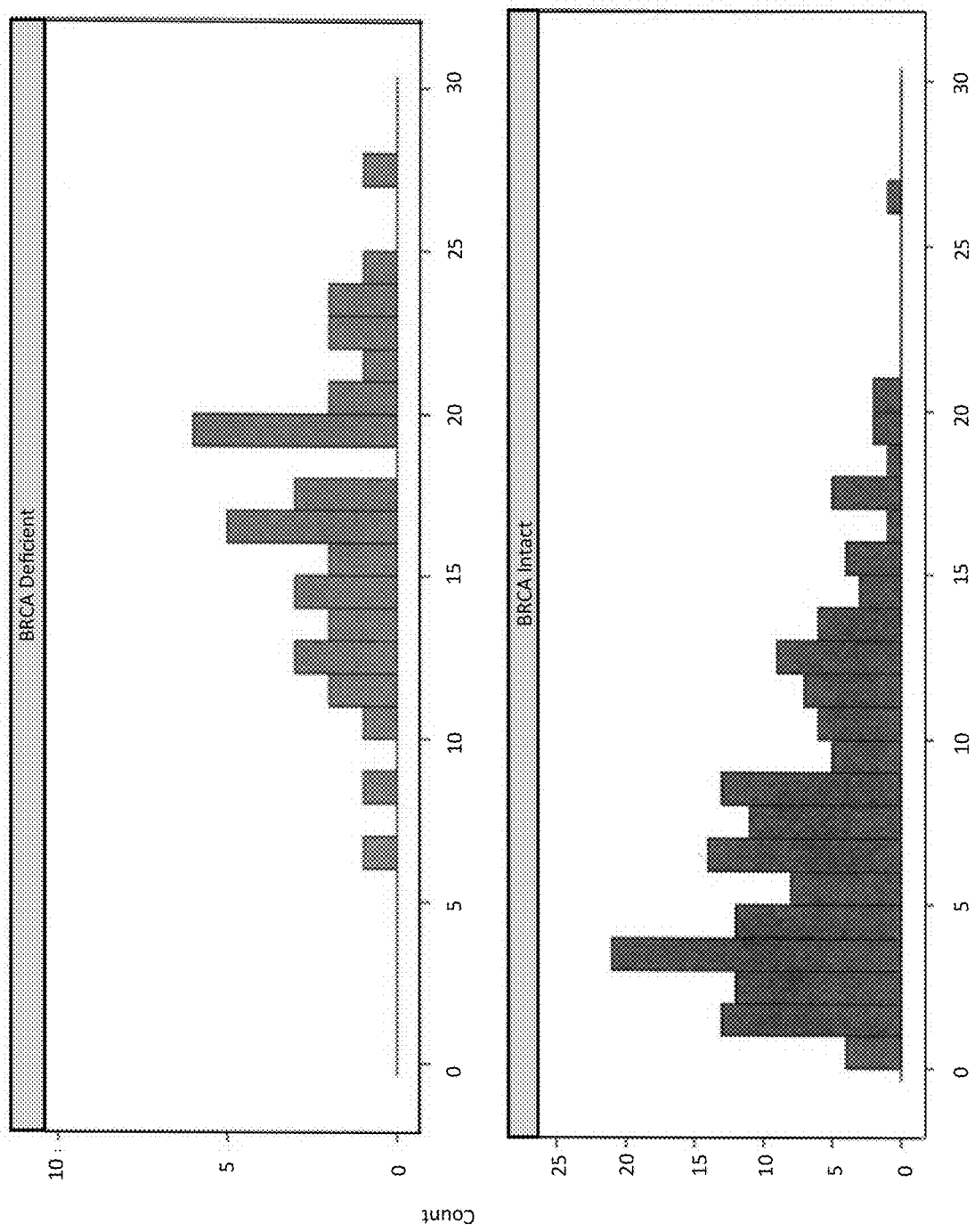
FIG. 9A illustrates HRD-LOH scores in BRCA 1/2 deficient (mutated or methylated) samples (top panel) and intact samples (bottom panel) in an all-comers breast cohort.
Figure 9B:
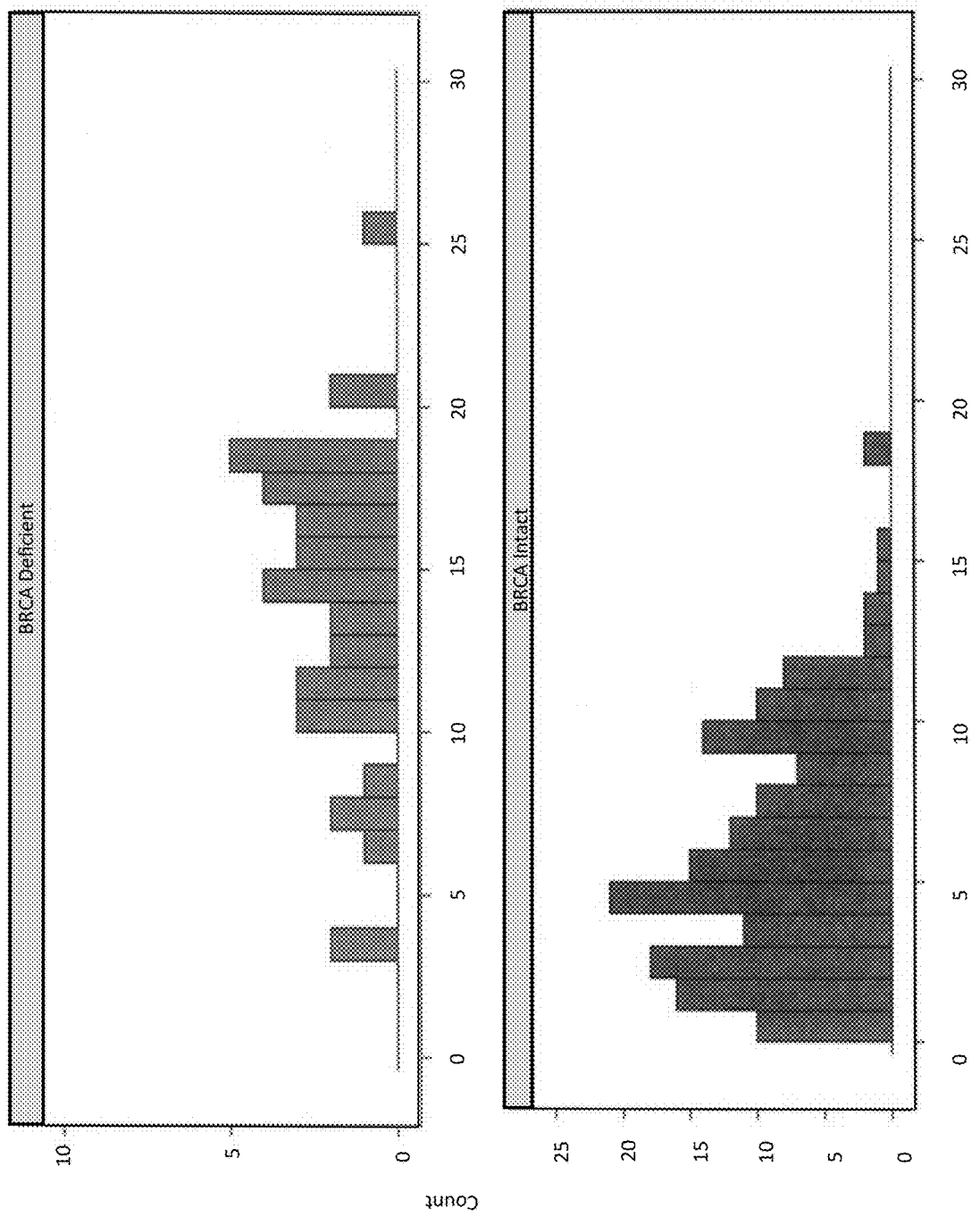
FIG. 9B illustrates HRD-TAI scores in BRCA1/2 deficient (mutated or methylated) samples (top panel) and intact samples (bottom panel) in an all-comers breast cohort.
Figure 9C:
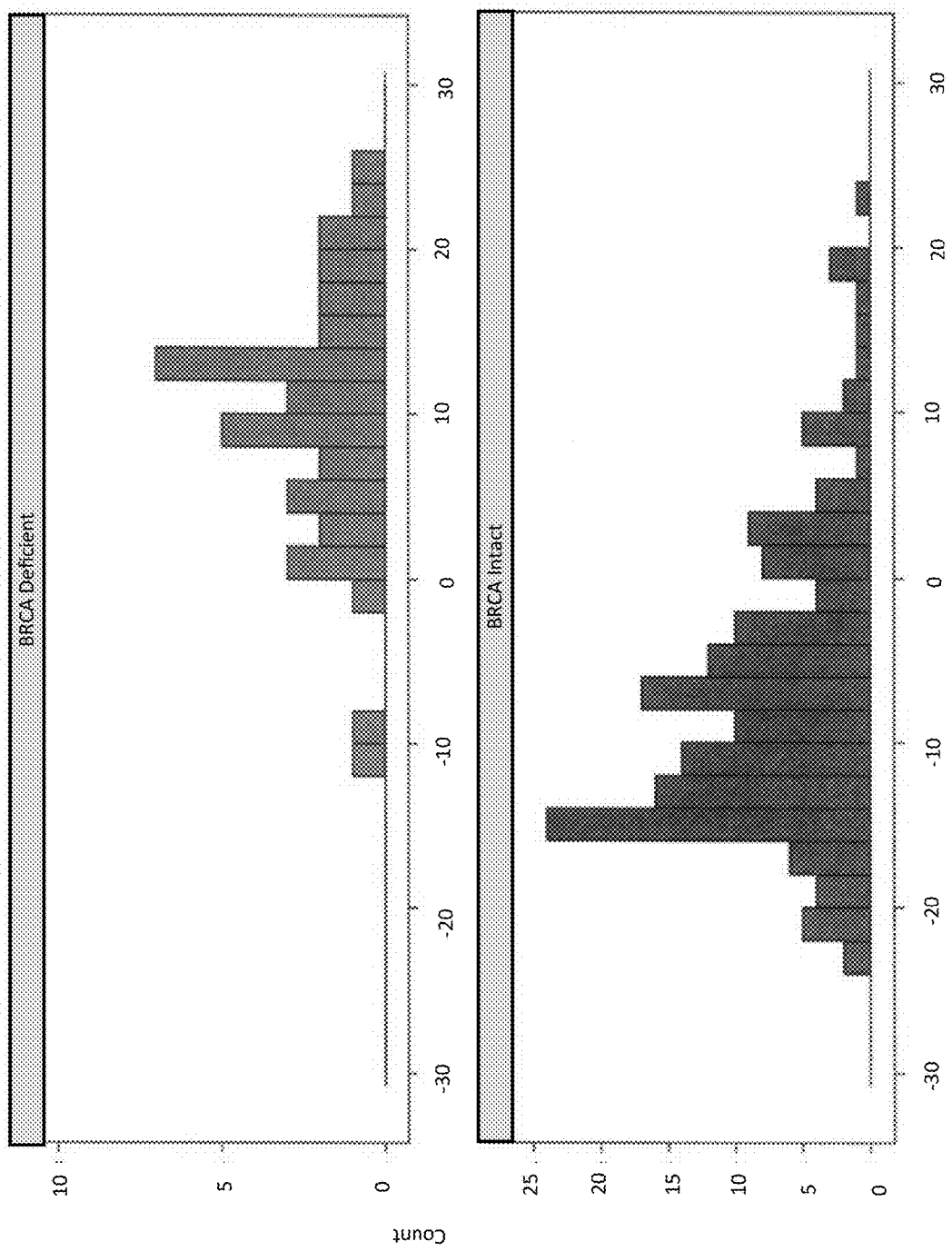
FIG. 9C illustrates HRD-LST scores in BRCA1/2 deficient (mutated or methylated) samples (top panel) and intact samples (bottom panel) in an all-comers breast cohort.
Figure 10:
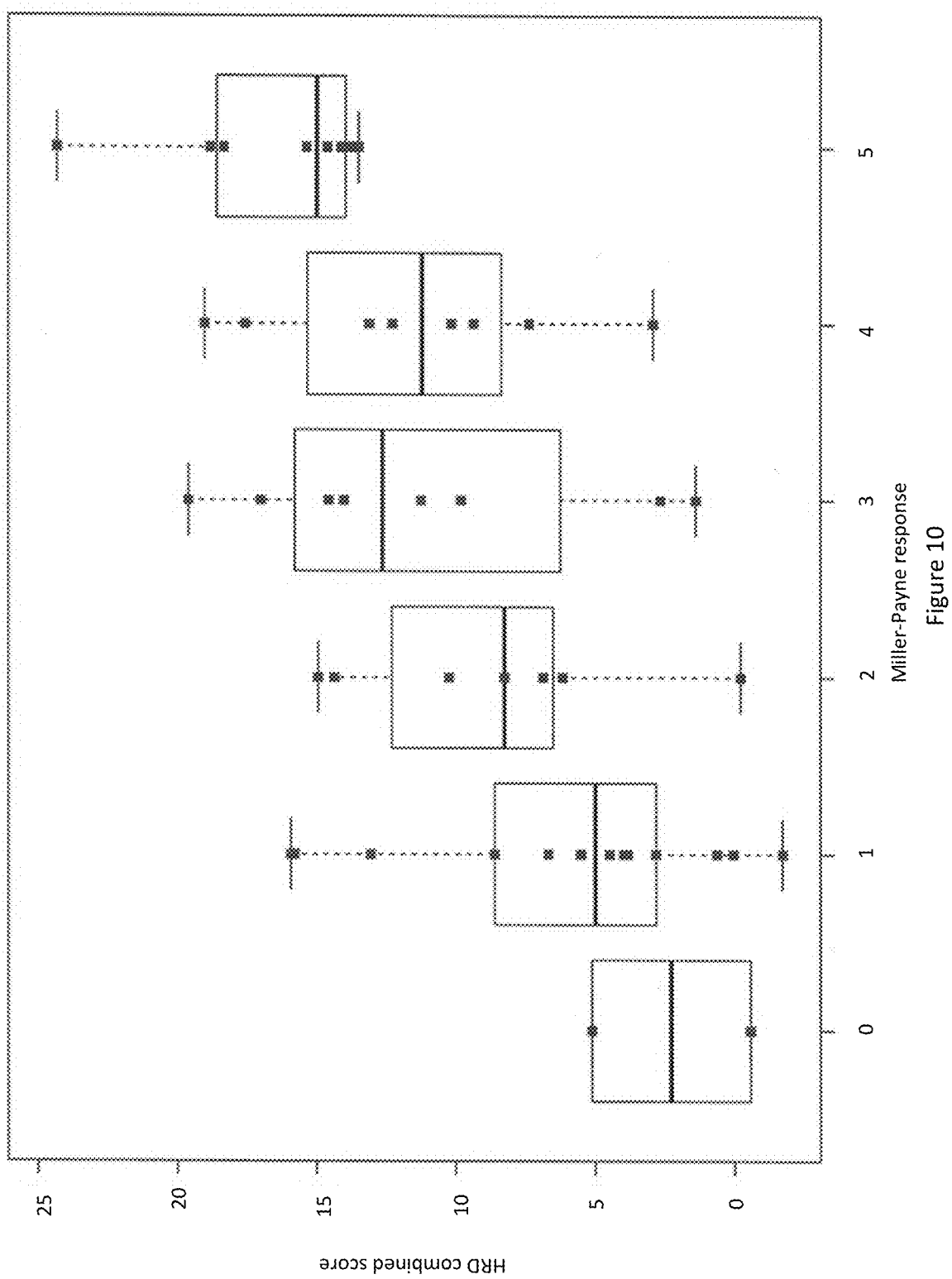
FIG. 10 illustrates an average (e.g., arithmetic mean) HRD-combined score (Y-axis) stratified by the Miller-Payne score (horizontal axis) in combined Cisplatin-1 and Cisplatin-2 cohorts.
Figure 11:
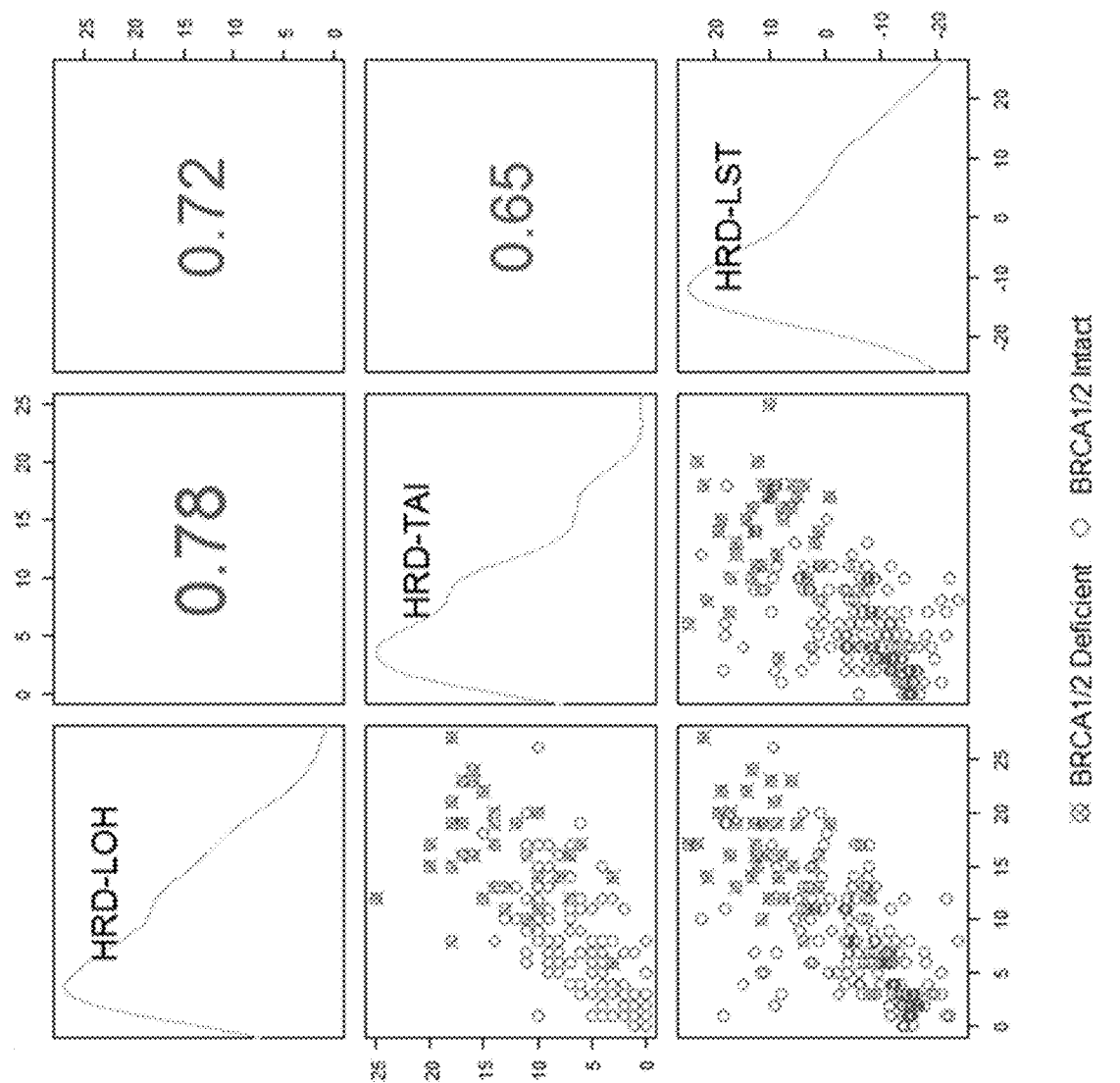
FIG. 11 illustrates a spearman correlation of 3 different measures of HR deficiency. Panels above the diagonal show correlation. Diagonal panels show density plots.

Table 6 shows BRCA1/2 mutation and BRCA1 promoter methylation frequency across four breast cancer subtypes. BRCA1/2 variant analysis was successful on 100% of samples, while large rearrangement analysis was less robust with 198/214 samples producing data that passed QC metrics. Deleterious mutations were observed in 24/214 individuals (one had a somatic mutation in BRCA1 and a germline mutation in BRCA2). Matched normal DNA was available for 23/24 mutants, and was used to determine whether the identified mutation was germline or somatic. BRCA1 promoter methylation analysis was successful on 100% of samples. FIG. 9 illustrates HRD scores in BRCA1/2 deficient samples.

TABLE 6

| Subtype | n | BRCA1 Mutations | BRCA2 Mutations | Total Mutants (%) | Germline Mutations (%) | BRCA1 Promoter Methylation (%) |
|---|---|---|---|---|---|---|
| TNBC | 63 | 10 | 3 | 10 (15.9) | 69 | 13 (20.6) |
| ER+/HER2− | 50 | 2 | 2 | 4 (8.0) | 100 | 1 (2.0) |
| ER−/HER2+ | 38 | 3† | 1 | 4† (10.5) | 50 | 0 |
| ER+/HER2+ | 63 | 8* | 1 | 7* (11.1) | 57 | 1 (1.6) |

*Includes one individual who still retains intact functional copies of BRCA1.

†Includes one individual whose functional status for BRCA1 could not be determined.

Table 7 shows the association between the three HRD scores and BRCA 1/2 deficiency in the all-corners breast cohort. The combined score was the arithmetic mean of the three HRD scores.

TABLE 7

| | Breast Cancer Subtype | All | TNBC | ER+/HER− | ER−/HER2+ | ER+/HER2+ |
|---|---|---|---|---|---|---|
| | Number of Individuals | 197 | 52 | 50 | 35 | 60 |
| | Number of BRCA1/2 Deficient (%) | 38 (100) | 23 (61) | 5 (13) | 3 (8) | 7 (18) |
| HRD-LOH mean | BRCA1/2 Intact | 7.2 | 8.2 | 7.1 | 8.3 | 6.0 |
| | BRCA1/2 Deficient | 16.5 | 17.7 | 17.2 | 12.0 | 14.1 |
| | p value | $1.3 \times 10^{-17}$ | $1.5 \times 10^{-8}$ | 0.0025 | 0.18 | $2.1 \times 10^{-5}$ |
| HRD-TAI mean | BRCA1/2 Intact | 5.4 | 6.8 | 4.3 | 6.4 | 5.1 |
| | BRCA1/2 Deficient | 13.7 | 13.5 | 15.0 | 7.7 | 15.9 |
| | p value | $1.5 \times 10^{-19}$ | $2.2 \times 10^{-7}$ | $1.3 \times 10^{-5}$ | 0.58 | $1.4 \times 10^{-6}$ |
| HRD-LST mean | BRCA1/2 Intact | −7.0 | −5.1 | −6.7 | −6.7 | −8.3 |
| | BRCA1/2 Deficient | 10.2 | 12.0 | 11.7 | 2.7 | 6.1 |
| | p value | $3.5 \times 10^{-18}$ | $8.0 \times 10^{-11}$ | $3.2 \times 10^{-4}$ | 0.082 | 0.0024 |
| HRD combined mean | BRCA1/2 Intact | 1.9 | 3.3 | 1.6 | 2.7 | 0.9 |
| | BRCA1/2 Deficient | 13.4 | 14.4 | 14.6 | 7.5 | 12.0 |
| | p value | $1.1 \times 10^{-24}$ | $7.8 \times 10^{-13}$ | $2.3 \times 10^{-5}$ | 0.072 | $2.1 \times 10^{-5}$ |

Table 8 shows the association between HRD scores and pCR (Miller-Payne 5) in TNBC treated with cisplatin in a neoadjuvant setting. Data was available from samples from the Cisplatin-1 (Silver et al., *Efficacy of neoadjuvant Cisplatin in triple-negative breast cancer*. J. CLIN. ONCOL. 28:1145-53 (2010)) and Cisplatin-2 (Birkbak et al., (2012)) trials. pCR was defined as those patients with Miller-Payne 5 status following neoadjuvant treatment. HRD-combined was the arithmetic mean of the three HRD scores.

TABLE 8

| Score | pCR Mean | Non-pCR Mean | OR (95% CI) for $75^{th}$-$25^{th}$ percentiles | P value |
|---|---|---|---|---|
| HRD-LOH | 20.6 | 13.4 | 7.4 (1.5, 35.6) | 0.0035 |
| HRD-TAI | 15.8 | 10.7 | 6.5 (1.3, 32.6) | 0.0067 |
| HRD-LST | 13.4 | 1.4 | 14.7 (2.1, 102) | 0.00065 |
| HRD-combined | 16.6 | 8.5 | 22.4 (2.1, 239) | 0.00029 |

Conclusions

BRCA1/2 deficiency and elevated HRD scores were observed in all breast subtypes, and the HRD score detected BRCA1/2 deficiency. All three HRD scores predicted/detected response to cisplatin treatment in TNBC. The average of the three HRD scores (arithmetic mean) detected BRCA1/2 status in a breast all-comers cohort and cisplatin response in a second independent TNBC cohort. The arithmetic mean HRD-combined was a stronger predictor/detector of BRCA1/2 deficiency or therapy response than the individual HRD scores.

Example 4—Multivariate Analysis of BRCA1/2 Status and DNA-Based Assays for Homologous Recombination Deficiency The previous Examples described DNA-based scores measuring homologous recombination deficiency (HRD), which demonstrates that each score is significantly associated with BRCA1/2 deficiency, as is an HRD-combined score defined as an arithmetic mean of three different HRD scores. This Example extends the results of the previous examples by examining (1) associations between each of the three scores and the HRD-combined score, (2) associations of clinical variables with the HRD-combined score, and (3) associations of clinical variables and the HRD-combined score with BRCA1/2 deficiency.

Methods:

The analyses in this Example 4 include the same 197 patient samples described in previous Examples. Briefly, 215 breast tumor samples were purchased as fresh frozen specimens from 3 commercial vendors. Samples were selected to give approximately equal representation of breast cancer subtypes according to IHC analysis of ER, PR, and HER2. 198 samples produced reliable HRD scores according to a Kolmogorov-Smirnov quality metric. One patient with a passing HRD score was removed from analysis due to unusual breast cancer subtype (ER/PR+ HER2−). Patient tumor and clinical characteristics are detailed in Table 9.

Patient clinical data were provided for 91 variables, but data for most variables were too sparse to be included in analysis. Breast cancer subtype (TNBC, ER+/HER2−, ER−/HER2+, ER+/HER2+) was available for all patients. The other variables considered were age at diagnosis (provided for 196/197 patients), stage (provided for 191/197 patients), and grade (provided for 190/197 patients).

TABLE 9

| | | All Patients (%) | Triple negative (%) | ER+/ HER2− (%) | ER−/ HER2+ (%) | ER+/ HER2+ (%) | BRCA1/2 Mutant (%) | BRCA1/2 Deficient (%) |
|---|---|---|---|---|---|---|---|---|
| Total Patients | | 197 (100) | 52 (26.4) | 50 (25.4) | 35 (17.8) | 60 (30.5) | 24 (12.2) | 38 (19.2) |
| Age of Diagnosis | Range | 28-90 | 29-90 | 33-80 | 29-76 | 28-79 | 33-79 | 29-76 |
| | Median | 56 | 54 | 62 | 55 | 54.5 | 55.5 | 49 |
| | % < 60 | 57 | 61 | 46 | 60 | 62 | 62.5 | 70 |
| Stage | I | 13 (6.6) | 7 (13.5) | 2 (4) | 1 (2.9) | 3 (5) | 2 (8.3) | 3 (7.9) |
| | II | 121 (61.4) | 28 (53.8) | 31 (62) | 25 (71.4) | 37 (61.7) | 17 (70.8) | 23 (60.5) |
| | III | 54 (27.4) | 9 (17.3) | 17 (34) | 8 (22.9) | 20 (33.3) | 5 (20.8) | 9 (23.7) |
| | IV | 3 (1.5) | 3 (5.8) | 0 (0) | 0 (0) | 0 (0) | 0 (0) | 1 (2.6) |
| | unknown | 6 (3) | 5 (9.6) | 0 (0) | 1 (2.9) | 0 (0) | 0 (0) | 2 (5.3) |

TABLE 9-continued

|  |  | All Patients (%) | Triple negative (%) | ER+/ HER2− (%) | ER−/ HER2+ (%) | ER+/ HER2+ (%) | BRCA1/2 Mutant (%) | BRCA1/2 Deficient (%) |
|---|---|---|---|---|---|---|---|---|
| Grade | 1 | 17 (8.6) | 4 (7.7) | 8 (16) | 0 (0) | 5 (8.3) | 0 (0) | 0 (0) |
|  | 2 | 102 (51.8) | 17 (32.7) | 30 (60) | 13 (37.1) | 42 (70) | 10 (41.7) | 14 (36.8) |
|  | 3 | 71 (36) | 26 (50) | 10 (20) | 22 (62.9) | 13 (21.7) | 13 (54.2) | 21 (55.3) |
|  | unknown | 7 (3.6) | 5 (9.6) | 2 (4) | 0 (0) | 0 (0) | 1 (4.2) | 3 (7.9) |

BRCA1/2 mutation screening and genome wide SNP profiles were generated using a custom Agilent SureSelect XT capture followed by sequencing on Illumina HiSeq2500. Methylation of the BRCA-1 promoter region was determined by qPCR. Samples with greater than 10% methylation were classified as methylated.

HRD scores were calculated from whole genome tumor loss of heterozygosity (LOH) profiles (HRD-LOH), telomeric allelic imbalance (HRD-TAI), and large-scale state transitions (HRD-LST), the three HRD scores combined in the "HRD-combined score" discussed in this Example 4.

BRCA1/2 deficiency was defined as loss of function resulting from a BRCA-1 or BRCA-2 mutation, or methylation of the BRCA-1 promoter region, together with loss of heterozygosity (LOH) in the affected gene.

All statistical analyses were conducted using R version 3.0.2. All reported p-values are two-sided. The statistical tools employed included Spearman rank-sum correlation, Kruskal-Wallis one-way analysis of variance, and logistic regression.

For logistic regression modeling, HRD scores and age at diagnosis were coded as numeric variable. Breast cancer stage and subtype were coded as categorical variables. Grade was analyzed as both a numeric and categorical variable, but was categorical unless otherwise noted. Coding grade as numerical is not appropriate unless the increased odds of BRCA1/2 deficiency is the same when comparing grade 2 to grade 1 patients, as when comparing grade 3 to grade 2 patients.

P-values reported for univariate logistic regression models are based on the partial likelihood ratio. Multivariate p-values are based on the partial likelihood ratio for change in deviance from a full model (which includes all relevant predictor) versus a reduced model (which includes all predictors except for the predictor being evaluated, and any interaction terms involving the predictor being evaluated). Odds ratios for HRD scores are reported per interquartile range.

Results:

Pairwise correlations of the HRD-LOH, HRD-TAI, and HRD-LST scores were examined graphically (FIG. 1), and quantified with Spearman rank-sum correlation. Spearman rank-sum correlation was preferred to the more commonly used Pearson product-moment correlation, because right skew and outliers were observed in the HRD score distributions. All pairwise comparisons of scores showed positive correlation significantly different from zero ($p<10^{-16}$).

The extent of independent BRCA1/2 deficiency information captured by each of the HRD-LOH, HRD-TAI, and HRD-LST scores was measured by examining a multivariate logistic regression model with all three scores included as predictors of BRCA1/2 deficiency status (Table 10). The HRD-TAI score captured significant BRCA1/2 deficiency information independent of that provided by the other two scores (p=0.00016), as did the HRD-LST score (p=0.00014).

At the 5% significance level, the HRD-LOH score did not add significant independent BRCA1/2 deficiency information (p=0.069).

TABLE 10

|  | P-Value | OR (95% CI) for $75^{th}$-$25^{th}$ percentiles |
|---|---|---|
| HRD-LOH | 0.069 | 3.0 (0.89, 9.8) |
| HRD-TAI | 0.00016 | 5.8 (2.1, 16) |
| HRD-LST | 0.00014 | 7.4 (2.4, 23) |

Table 10 illustrates results from a 3-term multivariate logistic regression model with HRD-LOH, HRD-TAI, and HRD-LST as predictors of BRCA1/2 deficiency.

To assess whether the HRD-combined score adequately captured the BRCA1/2 deficiency information of its three components, we tested three bivariate logistic regression models. Each model included the HRD-combined score, and one of the HRD-LOH, HRD-TAI, or HRD-LST scores. None of the component scores added significantly to the HRD-combined score at the 5% significance level (HRD-LOH p=0.89, HRD-TAI p=0.090, HRD-LST p=0.28). This suggests that the HRD-combined score adequately captures the BRCA1/2 deficiency information of the HRD-LOH, HRD TAI, and HRD-LST scores.

The HRD-combined score was finally compared to a model-based combined score which was optimized to predict BRCA1/2 deficiency in this patient set. While the HRD-combined score weights each of the HRD-LOH, HRD-TAI, and HRD-LST scores equally, the model-based score assigns the HRD-TAI score approximately twice the weight of the HRD-LOH or HRD-LST scores. The formula for the model-based score is given by $$HRD\text{-}Model = 0.11 \times (HRD\text{-}LOH) + 0.25 \times (HRD\text{-}TAI) + 0.12 \times (HRD\text{-}LST).$$

Results from univariate analysis (Table 11), show that the HRD-Model score outperforms the HRD-combined score by approximately one order of magnitude (HRD Model $p=2.5 \times 10^{-25}$, HRD-Combined $p=1.1 \times 10^{-24}$).

TABLE 11

|  |  | P-Value | OR (95% CI) |
|---|---|---|---|
| HRD-LOH |  | $1.30 \times 10^{-17}$ | 22 (8.4, 58) |
| HRD-TAI |  | $1.50 \times 10^{-19}$ | 17 (7.2, 41) |
| HRD-LST |  | $3.50 \times 10^{-18}$ | 19 (7.7, 46) |
| HRD-Combined |  | $1.10 \times 10^{-24}$ | 90 (22, 360) |
| HRD-Model |  | $2.50 \times 10^{-25}$ | 76 (19, 290) |
| Age at Diagnosis |  | 0.0071 | 0.96 (0.94, 0.99) |
| Stage |  | 0.88 |  |
|  | I |  | 1 |
|  | II |  | 0.78 (0.20, 3.1) |
|  | III |  | 0.67 (0.15, 2.9) |
|  | IV |  | 1.7 (0.11, 25) |

TABLE 11-continued

| | P-Value | OR (95% CI) |
|---|---|---|
| Cancer Subtype | $1.20 \times 10^{-05}$ | |
| ER−/HER2+ | | 1 |
| ER+/HER2− | | 1.2 (0.34, 5.8) |
| ER+/HER2+ | | 8.5 (2.3, 31) |
| TNBC | | 8.5 (2.3, 31) |
| Grade (Categorical) | 0.0011 | NA |
| Grade (Numerical) | 0.00053 | 3.1 (1.6, 6.3) |

Table 11 shows results from univariate logistic regression. Odds ratios for HRD scores are reported per IQR of the score. The odds ratio for age is reported per year. The odds ratio for grade (numerical) is per unit.

In a bivariate logistic regression model, the HRD-Model score did not add significant independent BRCA1/2 deficiency information to the HRD-combined score (p=0.089). This further suggests that the HRD-combined score adequately capture the BRCA1/2 deficiency information of the HRD-LOH, HRD-TAI, and HRD-LST scores.

Figure 12:
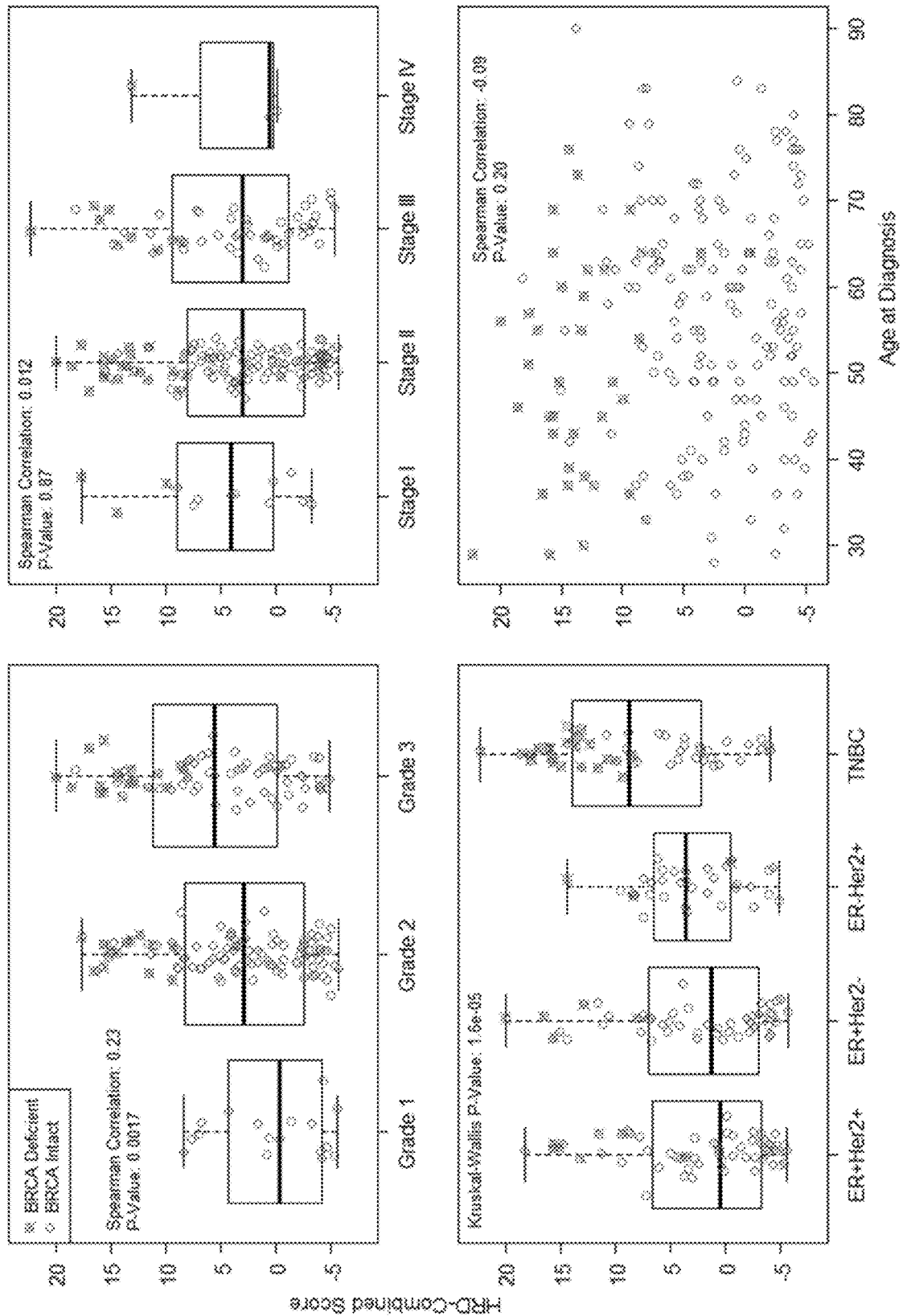
FIG. 12 illustrates associations of clinical variables with HRD-combined score.

Associations of clinical variables with the HRD-combined score are shown in FIG. 12. The HRD-combined score was significantly correlated with tumor grade (Spearman correlation 0.23, p=0.0017). Correlations with breast cancer stage and age at diagnosis were not significantly different from zero at the 5% level. Mean HRD combined scores differed significantly among breast cancer subtypes (p=1.6× $10^{-5}$) according to a Kruskal-Wallis one-way analysis of variance test.

Heterogeneity of the HRD-combined score among clinical sub-populations was tested by examining the significance of interaction terms in multivariate logistic regression models. For each clinical variable, we added a term for interaction with the HRD-combined score to a model including all clinical variable, and the HRD-combined score. None of the interaction terms reached significance at the 5% significance level. Thus, there is no evidence to suggest that the probability of BRCA1/2 deficiency conferred by the HRD-combined score varies among clinical sub-populations.

Analogous tests for each of the HRD-LOH, HRD-TAI, and HRD-LST scores indicated significant interaction of the HRD-TAI score with age (p=0.0072) and grade (p=0.015), and significant interaction of the HRD-LST score with breast cancer subtype (p=0.021). Adjusted for multiple comparisons, only the interaction of the HRD-TAI score with age maintained significance at the 5% level (p=0.029). Significance of this interaction suggests that the increased probability of BRCA1/2 deficiency per unit increase of the HRD-TAI score diminishes as age increases.

Figure 13:
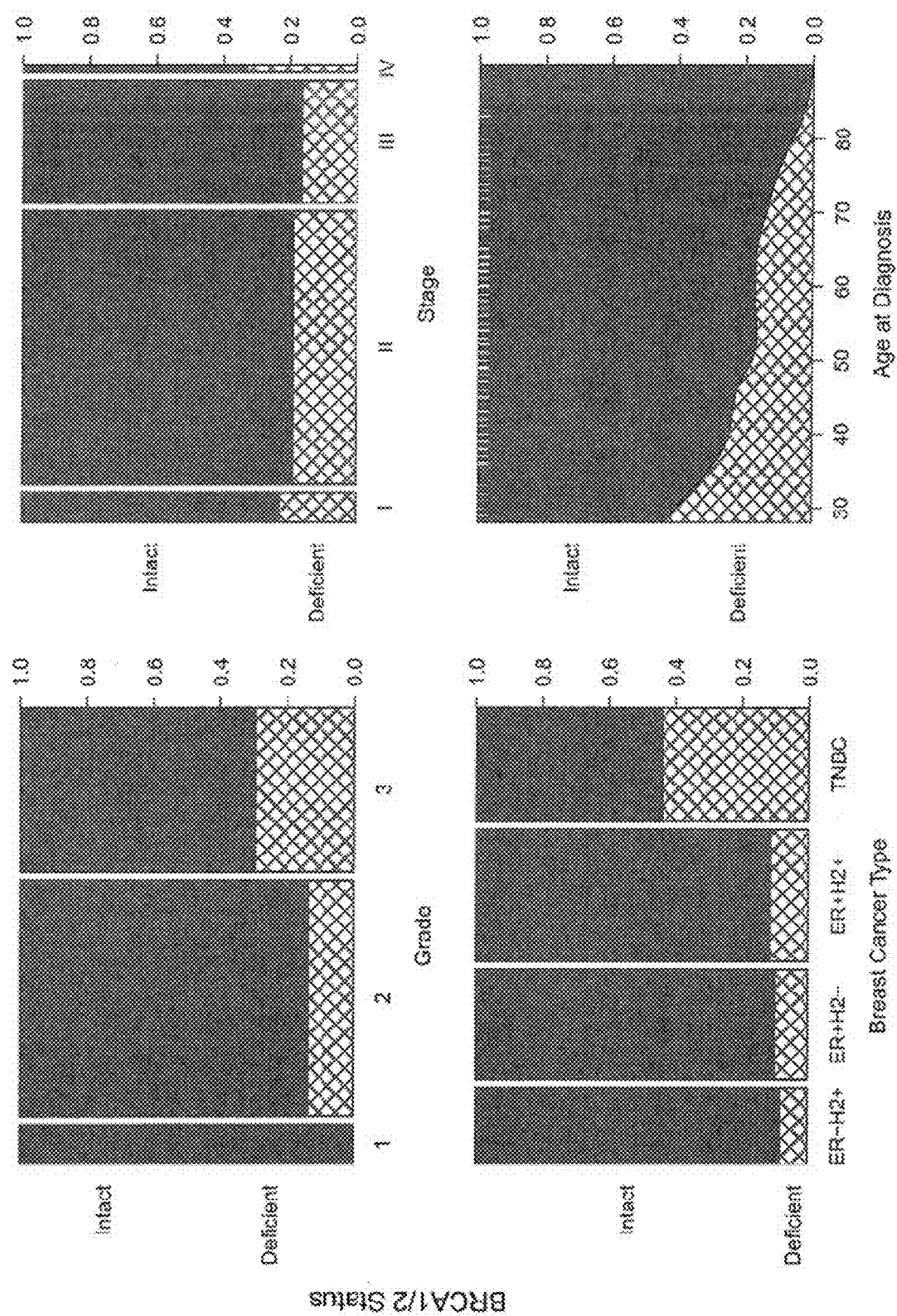
FIG. 13 illustrates associations of clinical variables with BRCA1/2 deficiency. The top panels, and the bottom left panel, show the proportion of BRCA1/2 deficient patients within each category of grade, stage, and breast cancer type. The width of each bar is proportional to the number of patients in each category. The bottom right panel shows a conditional density estimate of BRCA1/2 deficiency give age.

Associations of clinical variables with BRCA1/2 deficiency are displayed in FIG. 13. Clinical variables and the HRD-Combined score were evaluated with univariate (Table 11) and multivariate (Table 12) logistic regression models. Odds ratios for HRD scores are reported per IQR. Odds ratios for age at diagnosis are reported per annum.

TABLE 12

| | P-Value | OR (95% CI) |
|---|---|---|
| HRD-Combined | $1.2 \times 10^{-16}$ | 87 (17, 450) |
| Age at Diagnosis | 0.027 | 0.95 (0.91, 1.0) |
| Stage | 0.63 | |
| I | | 1 |
| II | | 2.4 (0.22, 27) |
| III | | 0.99 (0.073, 13) |
| IV | | 3.1 (0.0011, 9100) |

TABLE 12-continued

| | P-Value | OR (95% CI) |
|---|---|---|
| Grade | 0.40 | NA |
| Type | 0.087 | |
| ER−/HER2+ | | 1 |
| ER+/Her2− | | 0.39 (0.039, 3.8) |
| ER+/Her2+ | | 1.3 (0.16, 10) |
| TNBC | | 3.9 (0.62, 24) |

Table 12 shows results from multivariate logistic regression. Odds ratios for HRD scores are reported per IQR of the score. The odds ratio for age is reported per year.

In univariate analysis, each of the HRD scores (HRD-LOH, HRD-TAI, HRD-LST, HRD-Combined, and HRD-Model) was significantly associated with BRCA1/2 deficiency. Higher scores indicated greater likelihood of deficiency. Increased age at diagnosis was significantly associated with decreased risk of BRCA1/2 deficiency (p=0.0071). Univariate results for breast cancer subtype, and tumor grade (both categorical and numeric), were also statistically significant. Cancer stage was not associated with BRCA1/2 status.

In multivariate analyses, a model based on the HRD-combined score, and all available clinical variables, was examined. The HRD-combined score captured significant BRCA1/2 deficiency information that was not captured by clinical variables (p=$1.2 \times 10^{-16}$). Of the available clinical variables, only age at diagnosis maintained significance in the multivariate setting (p=0.027). Grade was coded as a categorical variable, and was not statistically significant (p=0.40). Grade was also not significant when coded as a numerical variable (p=0.28). Quadratic and cubic effects for the HRD-combined score were tested in multivariate models including all clinical variables, but were not statistically significant.

Discussion.

In this Example 4 the frequency of BRCA1/2 defects ranged from ~9 to ~16% across 4 subtypes of breast cancer as defined by IHC subtyping. Sequencing of matched tumor and normal DNA samples suggests that approximately 75% of the observed mutations were germline in origin. The primary method for loss of the second allele in breast cancer is via LOH, however ~24% of tumors also carried subsequent somatic deleterious mutations in the second allele. In addition, an apparently sporadic breast tumor was seen in one individual carrying a BRCA2 somatic deleterious mutation.

All 3 HRD scores showed strong correlation with BRCA1/2 deficiency regardless of subtype, and the frequency of elevated scores suggests that a significant proportion of all breast tumor subtypes carry defects in the homologous recombination DNA repair pathway. These findings, especially when combined with those of Example 3 above, show that agents which target or exploit DNA damage repair (e.g., platinum agents) may prove effective across a subset of tumors (those with homologous recombination deficiency as detected according to the present disclosure) from all subtypes of breast cancer.

Implementation of these HRD scores, either singly or in combination, in the clinical setting is best using an assay that is compatible with core needle biopsies that have been formalin fixed and paraffin embedded ("FFPE"). Samples of this type yield very low quantity and low quality DNA. DNA extracted from these FFPE treated samples often does not perform well in SNP microarray analysis.

Liquid hybridization based target enrichment technologies have been developed for production of libraries for next generation sequencing. These methodologies enable targeted sequencing of regions of interest after reduction in genomic complexity, resulting in decreased sequencing costs. Preliminary tests indicated that the available assays are compatible with DNA derived from FFPE DNA. In this Example 4 we report the development of a capture panel which targets ~54,000 SNPs distributed across the genome. Allele counts from the sequencing information that this panel provides can be used for copy number and LOH reconstruction, and the calculation of all 3 of the HRD scores. In addition, BRCA1 and BRCA2 capture probes may be included on the panel, as in this Example 4, which enable high quality mutation screening for deleterious variants in these genes in the same assay.

All 3 scores were significantly correlated with one another, suggesting that they all measure the same core genomic phenomenon. However, logistic regression analysis indicates that the scores could be combined resulting in stronger association with BRCA1/2 deficiency in this dataset.

The combination of a robust score capable of identifying tumors with defects in homologous recombination DNA repair and an assay compatible with formalin fixed paraffin embedded clinical pathological specimens facilitates the diagnostic identification and classification of patients with a high likelihood of response to agents targeting double strand DNA damage repair. In addition, such agents may have utility across all subtypes of breast cancer in which HRD is detected according to the present disclosure.

Example 5—High HRD Threshold Value (e.g., One Example of an HRD Signature)

This example demonstrates determination of high HRD. A threshold reference value was selected to have a high sensitivity for detecting HRD in breast and ovarian tumors that was nonspecific to treatment response or outcome. The total number of LOH, TAI, and LST Regions were determined. To calculate HRD scores, SNP data was analyzed using an algorithm that determines the most likely allele specific copy number at each SNP location. HRD-LOH was calculated by counting the number of LOH regions >15 Mb in length, but shorter than the length of a complete chromosome. HRD-TAI score was calculated by counting the number of regions >11 Mb in length with allelic imbalance that extend to one of the subtelomeres, but do not cross the centromere. HRD-LST score was the number of break points between regions longer than 10 Mb after filtering out regions shorter than 3 Mb. The combined score (HRD score) was the summation of the LOH/TAI/LST scores.

Figure 14:
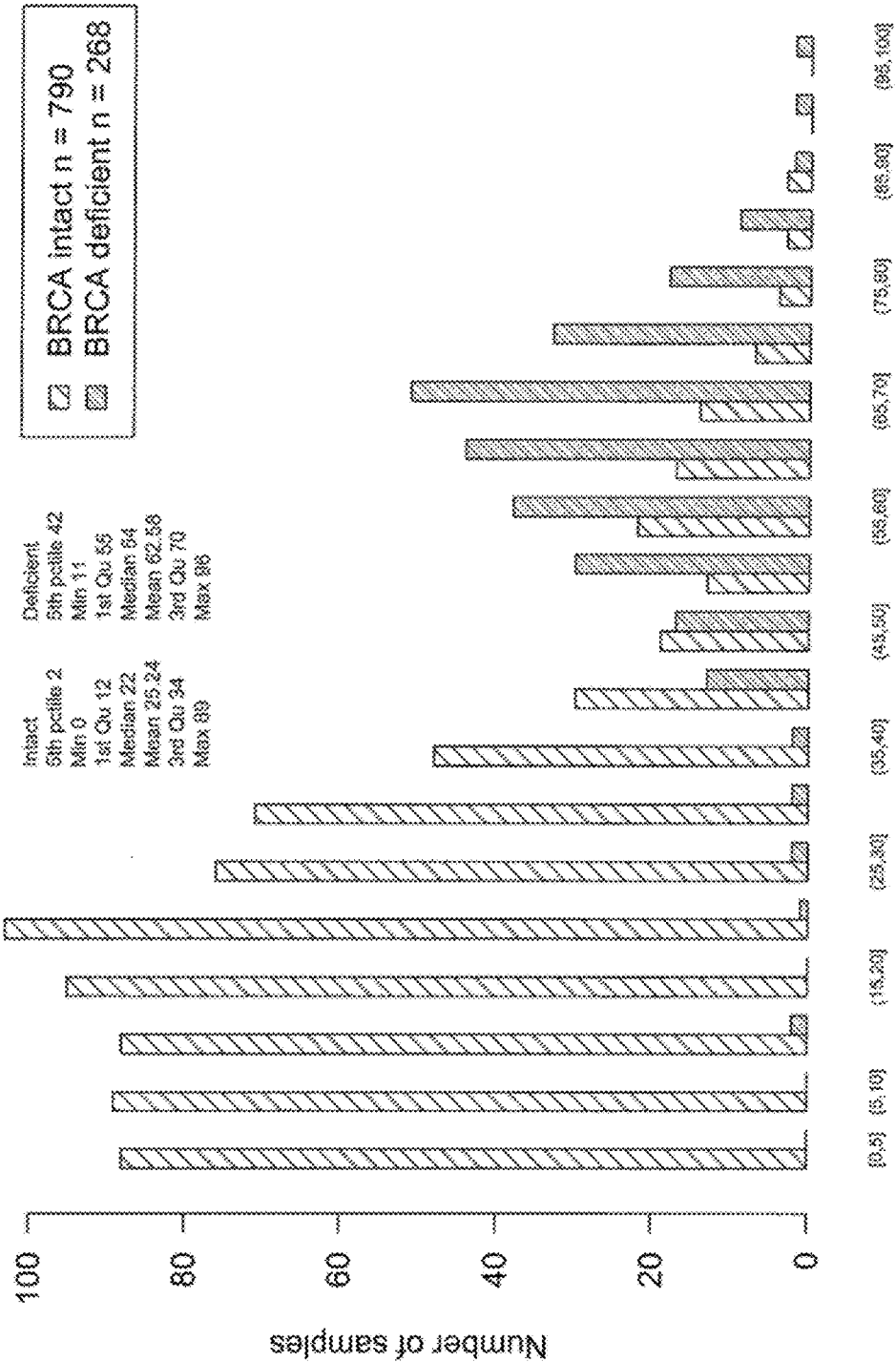
FIG. 14 illustrates determination of high HRD having a reference score 42.

The training set was assembled from 4 different cohorts (497 breast and 561 ovarian cases). The set consisted of 78 breast and 190 ovarian tumors that were lacking a functional copy of BRCA1 or BRCA2, because the distribution of HRD scores in BRCA-deficient samples represents the distribution of scores in HRD samples in general. The threshold was set at the $5^{th}$ percentile of the HRD scores in the training set, and gives >95% sensitivity to detect HR deficiency. High HRD (or an HRD signature) was defined as having a reference score ≥42 (FIG. 14).

Example 6—HRD Predicts Cisplatin Response in Triple Negative Breast Cancer

This example demonstrates how HRD scores as described herein can predict the efficacy of agents targeting HR deficiency in triple negative breast cancer (TNBC) samples. Analysis of a neoadjuvant TNBC cohort treated with cisplatin was examined relative to the relationship between all three HRD scores and response. All p values were from logistic regression models with response to cisplatin as the dependent variable.

Figure 15:
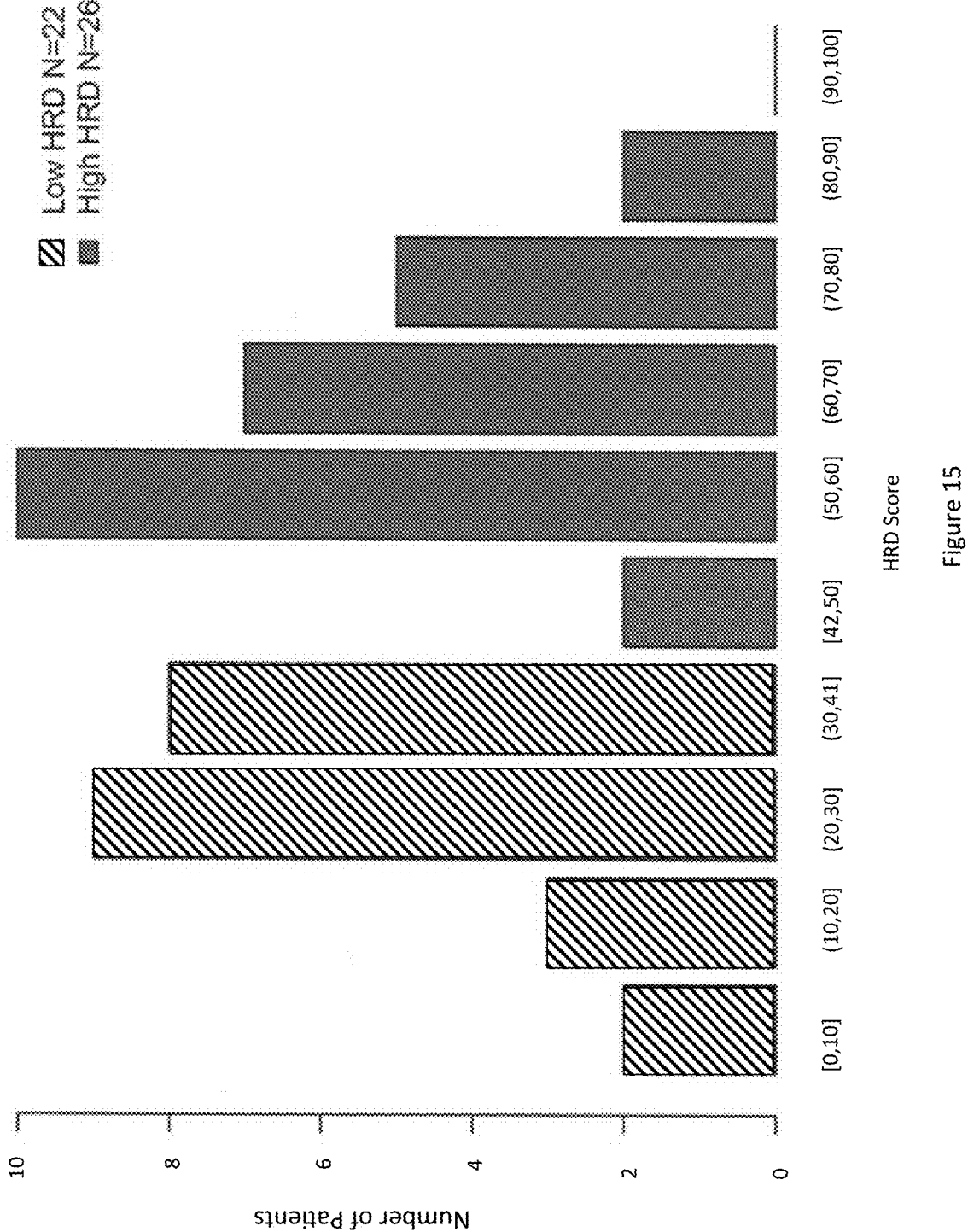
FIG. 15 illustrates a histogram showing the distribution of HRD scores in a cisplatin cohort. The four columns on the left represent low HRD, and the five columns on the right, with reference scores >42, represent high HRD.

HR Deficiency status was determined for 62 of the 70 samples (70 individual patients) received from a cisplatin cohort (8 had insufficient tumors for analysis). Of these, 31 (50%) were HR deficient, 22 (35%) were non-HR deficient, and 9 (15%) were undetermined. FIG. 15 provides a histogram showing the distribution of HRD scores in the cohort. Scores ≥42 were considered to have high HRD (see also, Example 5). The bimodality illustrated in FIG. 15 indicates that HRD scores effectively distinguished HR deficient and non-deficient states in the tumor. Pathologic complete response (pCR), which is associated with long-term survival, was defined as a residual cancer burden (RBC) of 0 and observed in 11/59 (19%) samples. Pathologic response (PR) was defined as an RBC of 0 or 1 and was observed in 22/59 (37%) samples. These overall response rates correlated with monotherapy expectations.

Statistical analyses followed a predefined Statistical Analysis Plan (SAP), which included primary, secondary, and BRCA wild-type subset analyses.

The primary analysis used HR Deficiency status to predict response in 50 samples. As shown in Table 13, HR deficient samples provided a better predictor of response for both PR and pCR. For example, 52% of HR deficient samples had a pathologic response as opposed to 9.5% of non-deficient samples having a pathologic response. Similarly, 28% of HR deficient samples had a pathologic complete response as opposed to 0% of non-deficient samples having a pathologic complete response.

TABLE 13

Primary analysis using HR Deficiency to predict response

| Responder | Deficient | Non-deficient | Logistic method | Odds ratio (95% CI) Reference: Non-deficient | Logistic p-value |
|---|---|---|---|---|---|
| PR = no | 14 | 19 | | | |
| PR = yes | 15 (52%) | 2 (9.5%) | Standard maximum likelihood | 10.18 (2.00, 51.89) | 0.0011 |
| pCR = no | 21 | 21 | | | |
| pCR = yes | 8 (28%) | 0 (0%) | Firth's penalized likelihood | 17.00 (1.91, 2249) | 0.0066 |

The secondary analysis used a quantitative HRD score as described in Example 5, to predict response in 48 samples. As shown in Table 14, HRD scores were significantly higher in samples from responders than non-responders, defined either as PR or pCR.

TABLE 14

Secondary analysis using quantitative HRD scores to predict response

| Responder | N | Mean (standard deviation) | Odds ratio per IQR (37.5) (95% CI) | Logistic p-value |
|---|---|---|---|---|
| PR = no | 33 | 39.8 (20.8) | | |
| PR = yes | 15 | 62.9 (16.1) | 10.5 (2.3, 48.6) | $3.1 \times 10^{-4}$ |
| pCR = no | 41 | 42.6 (20.3) | | |
| pCR = yes | 7 | 73.3 (11.4) | 117 (2.9, 4764) | $7.0 \times 10^{-5}$ |

Figure 16:
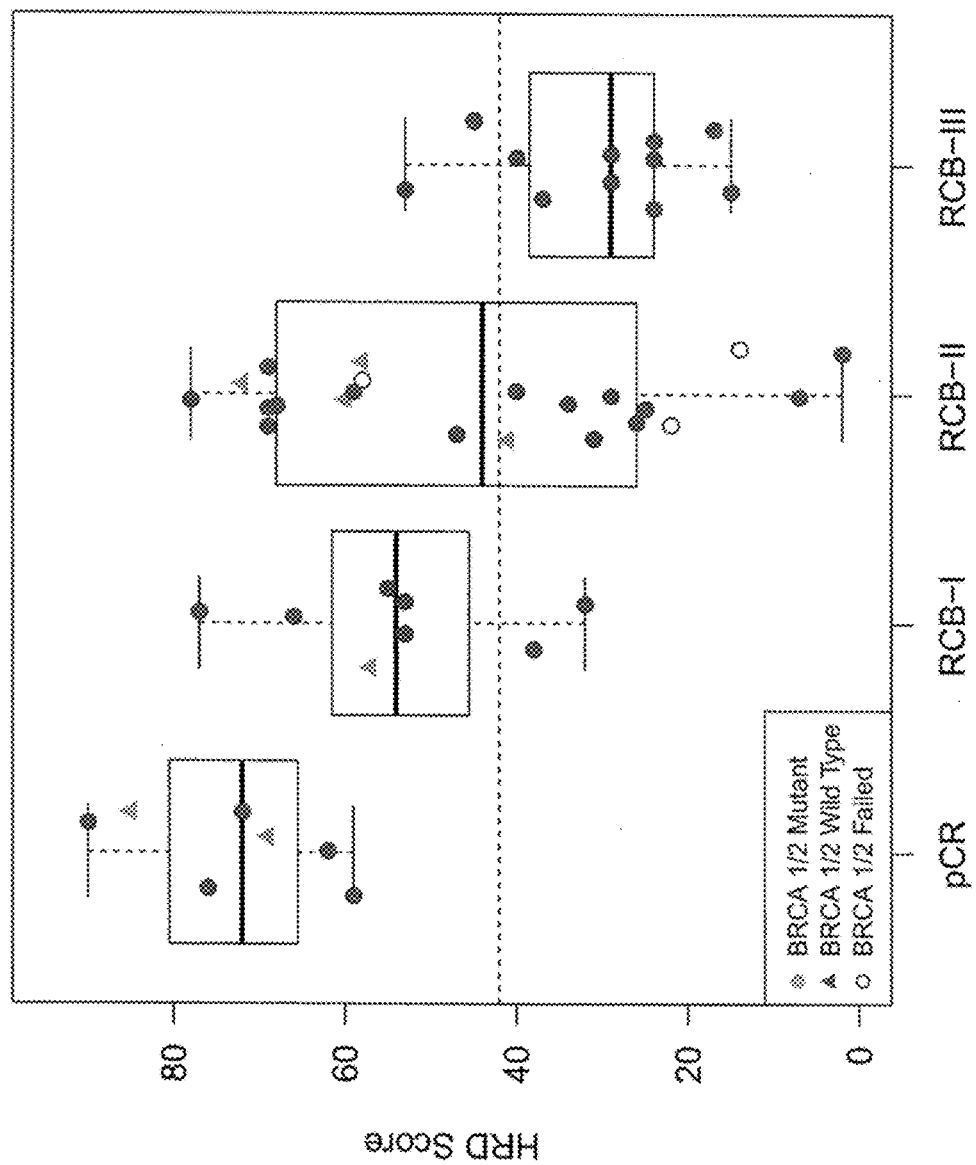
FIG. 16 illustrates the distribution of HRD scores within the pCR, RCB-I, RCB-II, and RCB-III classes of response. Boxes represent the interquartile range (IQR) of the scores with a horizontal line at the median. The dotted line at 42 represents the HRD threshold between low and high scores.
Figure 17:
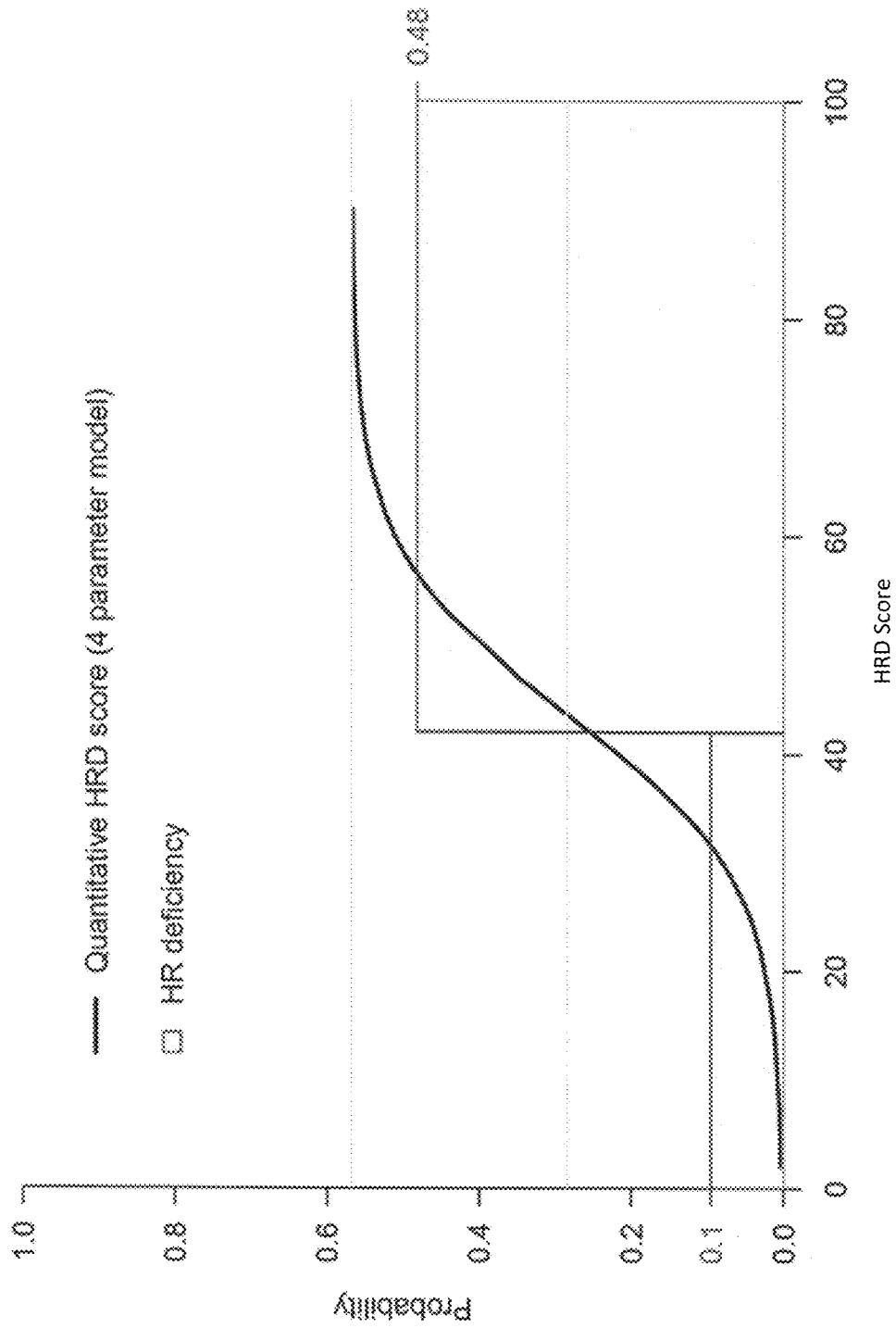
FIG. 17 illustrates a response curve for the quantitative HRD score. The curve is modeled by generalized logistic regression. The shaded boxes indicate the probability of response in HR Deficient vs Non-Deficient samples.

The distribution of HRD scores within each class of response for the secondary analysis as defined by BRCA mutation status is illustrated in FIG. 16, where the dotted line at 42 represents the HRD threshold between low and high scores. The response curve, or the probability of PR associated with each value of the quantitative HRD score for the secondary analysis is illustrated in FIG. 17. The curve shown in FIG. 17 was modeled by generalized logistic regression, which estimates 4 parameters: shape, scale, and the lower and upper limits of the curve. The shaded boxes indicate the probability of response in HR Deficient vs Non-Deficient samples. Table 15 shows that in the secondary analysis HR status remained significantly associated with pathologic response.

TABLE 15

Multivariable model of pathologic response

| Variable | Levels | Number of Patients (%) | Odds ratio (95% CI) | Logistic p-value |
|---|---|---|---|---|
| HR status | Non-deficient | 21 (42%) | Reference | 0.0017 |
|  | Deficient | 29 (58%) | 12.08 (1.96, 74.4) |  |
| Treatment | Cisplatin | 18 (36%) | Reference | 0.27 |
|  | Cisplatin + Bevacizumab | 32 (64%) | 2.23 (0.52, 9.64) |  |
| Tumor size* cm |  | Mean = 3.7, IQR = (2.7, 4.0) | 1.40 (0.84, 2.35) | 0.19 |
| Baseline nodal status | Negative | 27 (54%) | Reference | 0.24 |
|  | Positive | 23 (46%) | 2.29 (0.56, 9.33) |  |
| Age at diagnosis* (yrs) |  | Mean = 49.8, IQR = (43.0, 56.8) | 0.97 (0.90, 1.05) | 0.49 |

*Odds ratio per IQR

Figure 18:
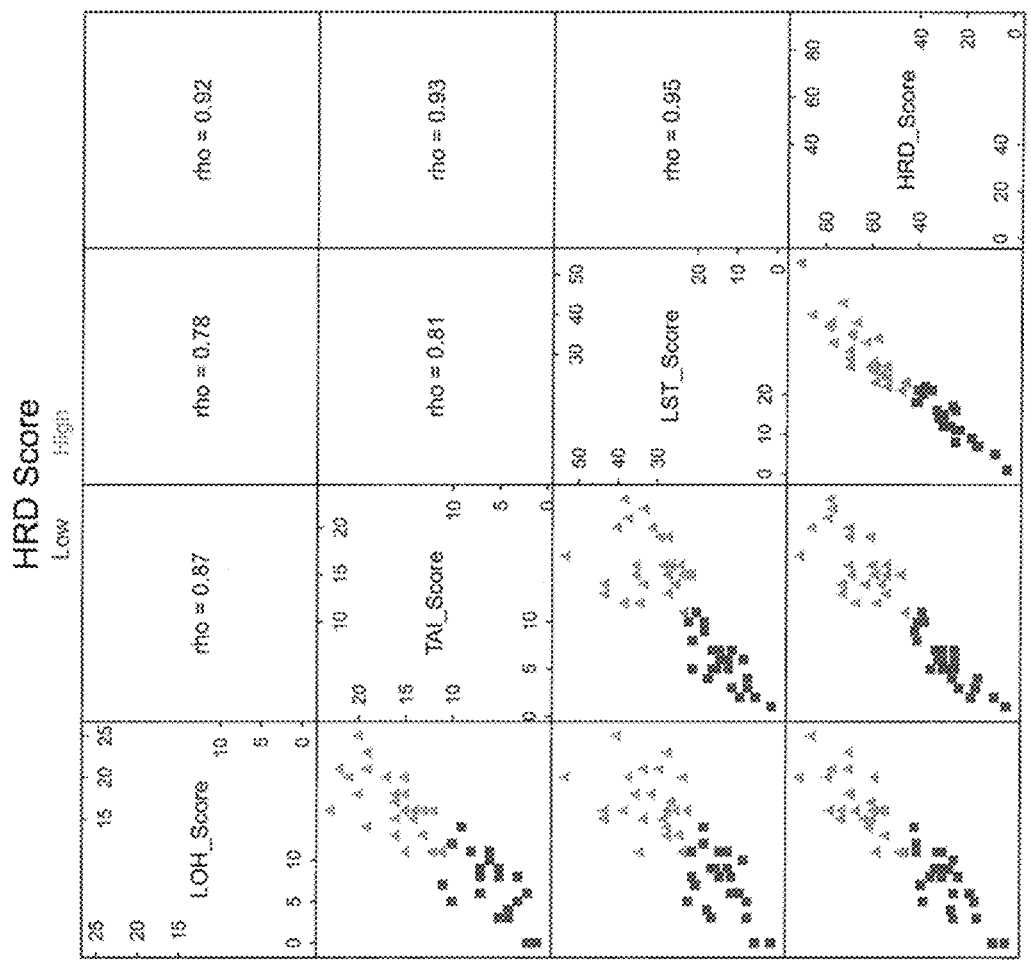
FIG. 18 illustrates HRD scores for individual HRD components (LOH, TAI, and LST).

Individual HRD components scores vs pathologic response are shown in Table 16 and illustrated in FIG. 18. Table 16 shows that each component score, i.e., LOH, TAI, and LST, was predictive of response, and their sum, i.e., the HRD score, was equally or more significant than any of the individual components (HRD p-value=3.1×10-4). FIG. 18 illustrates strong pairwise correlations between the component scores.

TABLE 16

Quantitative HRD component scores vs PR

| Responder PR | Component Score | Mean (Standard deviation) | Interquartile Range (IQR) | Odds ratio per IQR (95% CI) | Logistic p-value |
|---|---|---|---|---|---|
| No | LOH | 10.9 (6.0) | 8.0 |  |  |
| Yes |  | 15.7 (4.6) |  | 3.6 (1.3, 9.9) | 0.0072 |
| No | TAI | 9.7 (6.0) | 10.0 |  |  |
| Yes |  | 15.3 (4.2) |  | 6.2 (1.7, 23.0) | 0.0019 |
| No | LST | 19.3 (9.9) | 16.8 |  |  |
| Yes |  | 32.0 (9.9) |  | 8.5 (2.2, 33.2) | $1.4 \times 10^{-4}$ |

Further tested in the secondary analysis was association of BRCA1/2 mutation status with response. Table 17 confirmed that BRCA mutation status was associated with response; however, the association was not significant in this cohort (n=51) and BRCA mutation status was not as predictive as HR Deficiency.

TABLE 17

Secondary analysis using BRCA mutation status to predict response

| Responder | Mutant Number (% response) | Non-mutant Number (% response) | Odds ratio (95% CI) Reference: Non-deficient | Logistic p-value |
|---|---|---|---|---|
| PR = no | 4 | 29 |  |  |
| PR = yes | 5 (55.6%) | 13 (31.0%) | 2.79 (0.64, 12.11) | 0.17 |
| pCR = no | 6 | 37 |  |  |
| pCR = yes | 3 (33.3%) | 5 (11.9%) | 3.70 (0.70, 19.7) | 0.14 |

A subset analysis using HR Deficiency status in 38 BRCA wild-type samples was further conducted to demonstrate that HR Deficiency is predictive in samples with no BRCA1/2 mutations. As shown in Table 18, HR deficient samples provided a better predictor of response for both PR and pCR in BRCA wild-type samples. For example, 52.6% of HR deficient samples had a pathologic response as opposed to 10.5% of non-deficient samples having a pathologic response. Similarly, 26.3% of HR deficient samples had a pathologic complete response as opposed to 0% of non-deficient samples having a pathologic complete response.

TABLE 18

Subset analysis using HR Deficiency to predict response in BRCA wild-type samples

| Responder | Deficient Number (% response) | Non-deficient Number (% response) | Logistic method | Odds ratio (95% CI) Reference: Non-deficient | p-value |
|---|---|---|---|---|---|
| PR = no | 9 | 17 |  |  |  |
| PR = yes | 10 (52.6%) | 2 (10.5%) | Standard maximum likelihood | 9.44 (1.69, 52.7) | 0.0039 |
| pCR = no | 14 | 19 |  |  |  |
| pCR = yes | 5 (26.3%) | 0 (0%) | Firth's penalized likelihood | 14.79 (1.48, 2001) | 0.018 |

A subset analysis was further conducted using the quantitative HRD score in 38 BRCA wild-type samples. As shown in Table 19, samples having high HRD (with scores ≥42) provided a better predictor of response for both PR and pCR in BRCA wild-type samples.

TABLE 19

Subset analysis using quantitative HRD scores to predict response in BRCA wild-type samples

| Responder | N | Mean (Standard deviation) | Odds ratio per IQR (36.0) (9.5% CI) | Logistic p-value |
|---|---|---|---|---|
| PR = no | 26 | 38.1 (20.6) | | |
| PR = yes | 12 | 61.1 (16.5) | 8.74 (1.83, 41.7) | 0.0014 |
| pCR = no | 33 | 41.3 (20.4) | | |
| pCR = yes | 5 | 71.8 (12.3) | 45.5 (1.47, 1406) | 0.0012 |

In conclusion, this example demonstrates that the summation of all three HRD scores significantly predicted response to cisplatin treatment in TNBC.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method of detecting DNA from a patient responder to a cancer treatment regimen comprising a DNA damaging agent, anthracycline, topoisomerase I inhibitor, or PARP (poly ADP ribose polymerase) inhibitor, the method comprising:
   (i) extracting DNA from a sample comprising a cancer cell;
   (ii) contacting the DNA with at least 500 oligonucleotide probes corresponding to one or more single nucleotide polymorphism (SNPs);
   (iii) genotyping, using a computer, a plurality of SNP loci in the DNA that hybridizes to the oligonucleotide probes in (ii), wherein the SNP loci are spaced about 25 kb to about 100 kb apart on one or more chromosome pairs other than the human X/Y sex chromosome pair; and
   (iv) detecting, using a computer, DNA comprising a loss of heterozygosity (LOH) Region, DNA comprising a telomeric allelic imbalance (TAI) Region, and DNA comprising a large scale transition (LST) Region,
   wherein each LOH Region is characterized by loss of heterozygosity with a length of about 1.5 or more megabases but shorter than the length of the whole chromosome containing the LOH Region as determined by the presence or absence of SNP loci in corresponding regions on the one or more chromosome pairs; and
   wherein each TAI Region is characterized by allelic imbalance that extends to one of the subtelomeres, does not cross the centromere and is equal to or longer than a second length that is at least 1.5 megabases, and
   wherein each LST region is characterized by copy number transition along the length of the chromosome located between two regions, each longer than a third length that is at least 5 megabases, after filtering out copy number transitions along the length of the chromosome located between two regions, each shorter than a fourth length that is at most 4 megabases.

2. The method of claim 1, wherein the LOH, TAI, and LST Regions are determined in at least two pairs of human chromosomes.

3. The method of claim 1, wherein the cancer cell is an ovarian cancer cell, a breast cancer cell, or esophageal cancer cell.

4. The method of claim 1,
   wherein LOH Regions are defined as LOH Regions at least 15 megabases in length but less than either a complete chromosome or a complete chromosome arm,
   wherein TAI Regions are defined as TAI Regions at least 11 megabases in length but not extending across a centromere, and
   wherein LST Regions are defined as LST Regions at least 10 megabases in length.

5. The method of claim 1, wherein the DNA damaging agent is cisplatin, carboplatin, oxalaplatin, or picoplatin, the anthracycline is epirubincin or doxorubicin, the topoisomerase I inhibitor is campothecin, topotecan, or irinotecan, or the PARP inhibitor is olaparib, or velapirib.

6. An in vitro method of detecting presence of DNA from a patient responder to a cancer treatment regimen comprising a platinum agent, the method comprising:
   (i) extracting DNA from a sample comprising a cancer cell; and
   (ii) contacting the DNA with at least 500 oligonucleotide probes comprising one or more single nucleotide polymorphism (SNPs);
   (iii) genotyping, using a computer, a plurality of SNP loci in the DNA that hybridizes to the oligonucleotide probes in (ii), wherein the SNP loci are spaced about 25 kb to about 100 kb apart on one or more chromosome pairs other than the human X/Y sex chromosome pair; and
   (iv) detecting, using a computer, DNA comprising a loss of heterozygosity (LOH) Region, DNA comprising a telomeric allelic imbalance (TAI) Region, and DNA comprising a large scale transition (LST) Region,
   wherein each LOH Region is characterized by loss of heterozygosity with a length of about 1.5 or more megabases but shorter than the length of the whole chromosome containing the LOH Region as determined by the presence or absence of SNP loci in corresponding regions on the one or more chromosome pairs, and
   wherein each TAI Region is characterized by allelic imbalance that extends to one of the subtelomeres, does not cross the centromere and is equal to or longer than a second length that is at least 1.5 megabases, and
   wherein each LST region is characterized by comprises the number of copy number transition along the length of the chromosome located between two regions, each longer than a third length that is at least 5 megabases, after filtering out copy number transitions along the length of the chromosome located between two regions, each shorter than a fourth length that is at most 4 megabases.

7. The method of claim 6, wherein the LOH, TAI, and LST Regions are determined in at least two pairs of human chromosomes.

8. The method of claim 6,
   wherein LOH Regions are defined as LOH Regions at least 15 megabases in length but less than either a complete chromosome or a complete chromosome arm, wherein TAI Regions are defined as TAI Regions at least 11 megabases in length but not extending across a centromere, and wherein LST Regions are defined as LST Regions at least 10 megabases in length.

9. The method of claim 6, wherein the sample is deficient in BRCA1 or BRCA2 if a deleterious mutation, loss of heterozygosity, or high methylation is detected in either BRCA1 or BRCA2 in the sample.

10. The method of claim 9, wherein high methylation is detected if methylation is detected in at least 5% of BRCA1 or BRCA2 promoter CpGs analyzed.

* * * * *